(12) United States Patent
Khandke et al.

(10) Patent No.: US 9,556,240 B2
(45) Date of Patent: Jan. 31, 2017

(54) **STABLE FORMULATIONS OF *NEISSERIA MENINGITIDIS* RLP2086 ANTIGENS**

(75) Inventors: Lakshmi Khandke, Nanuet, NY (US); Rasappa Arumugham, Lansdale, PA (US); Bounthon Loun, Dardenne Prairie, MO (US)

(73) Assignee: Wyeth LLC, New York, NY (US)

( * ) Notice: Subject to any disclaimer, the term of this patent is extended or adjusted under 35 U.S.C. 154(b) by 442 days.

(21) Appl. No.: 13/814,285

(22) PCT Filed: Aug. 22, 2011

(86) PCT No.: PCT/IB2011/053684
§ 371 (c)(1),
(2), (4) Date: Feb. 5, 2013

(87) PCT Pub. No.: WO2012/025873
PCT Pub. Date: Mar. 1, 2012

(65) Prior Publication Data
US 2013/0171194 A1 Jul. 4, 2013

Related U.S. Application Data

(60) Provisional application No. 61/376,160, filed on Aug. 23, 2010.

(51) Int. Cl.
| | | |
|---|---|---|
| *A61K 39/095* | (2006.01) | |
| *A61K 39/00* | (2006.01) | |
| *A61K 39/02* | (2006.01) | |
| *A61K 39/385* | (2006.01) | |
| *C07K 14/22* | (2006.01) | |
| *G01N 33/569* | (2006.01) | |
| *A61K 31/194* | (2006.01) | |
| *A61K 31/4172* | (2006.01) | |
| *A61K 38/16* | (2006.01) | |

(52) U.S. Cl.
CPC .......... *C07K 14/22* (2013.01); *A61K 31/194* (2013.01); *A61K 31/4172* (2013.01); *A61K 38/164* (2013.01); *A61K 39/095* (2013.01); *G01N 33/56911* (2013.01); *A61K 2039/55505* (2013.01); *A61K 2039/55555* (2013.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 4,554,101 A | 11/1985 | Hopp |
| 4,650,764 A | 3/1987 | Temin et al. |
| 4,666,829 A | 5/1987 | Glenner et al. |
| 4,708,871 A | 11/1987 | Geyson |
| 4,797,368 A | 1/1989 | Carter et al. |
| 4,861,719 A | 8/1989 | Miller |
| 4,912,094 A | 3/1990 | Myers et al. |
| 4,925,792 A | 5/1990 | Rappuoli |
| 4,980,289 A | 12/1990 | Temin et al. |
| 5,057,540 A | 10/1991 | Kensil et al. |
| 5,078,996 A | 1/1992 | Conlon, III et al. |
| 5,124,263 A | 6/1992 | Temin et al. |
| 5,139,941 A | 8/1992 | Muzyczka et al. |
| 5,254,339 A | 10/1993 | Morein |
| 5,399,346 A | 3/1995 | Anderson et al. |
| 5,459,127 A | 10/1995 | Felgner et al. |
| 5,514,581 A | 5/1996 | Ferrari et al. |
| 5,550,213 A | 8/1996 | Anderson et al. |
| 5,565,204 A | 10/1996 | Kuo et al. |
| 5,580,859 A | 12/1996 | Felgner et al. |
| 5,583,038 A | 12/1996 | Stover |
| 5,589,466 A | 12/1996 | Felgner et al. |
| 5,597,572 A | 1/1997 | Huergo et al. |
| 5,614,382 A | 3/1997 | Metcalf |
| 5,668,004 A | 9/1997 | O'Donnell |
| 5,723,127 A | 3/1998 | Scott et al. |
| 5,739,118 A | 4/1998 | Carrano et al. |
| 5,955,580 A | 9/1999 | Green et al. |
| 6,113,918 A | 9/2000 | Johnson et al. |
| 6,130,085 A | 10/2000 | Hamers et al. |
| 6,149,919 A | 11/2000 | Domenighini |
| 6,165,995 A | 12/2000 | Hilgers |
| 6,207,646 B1 | 3/2001 | Krieg et al. |
| 6,245,892 B1 | 6/2001 | Oaks et al. |
| 6,270,775 B1 | 8/2001 | Cleary |

(Continued)

FOREIGN PATENT DOCUMENTS

| | | |
|---|---|---|
| AU | 2002339217 | 3/2003 |
| AU | 2006318155 | 5/2007 |

(Continued)

OTHER PUBLICATIONS

Andersen, et al, "Immune Responses to Meningococcal Outer Membrane Vesicles After Intranasal Immunisation", Twelfth International Pathogenic Neisseria Conference, Nov. 12-17, 2000, Galveston, Texas (Abstract #057).
Fredriksen et al, "Production, Characterization and Control of MenB-Vaccine <<Folkehelsa>>: An Outer Membrane Vesicle Vaccine Against Group B Meningococcal Disease", NIPH Annals 14(2):67-80 (1991).
Koeberling at el, "Bactericidal Antibody Responses Elicited by a Meningococcal Outer Membrane Vesicle Vaccine with Overexpressed Factor H-binding Protein and Genetically Attenuated Endotoxin", The Journal of Infectious Diseases 198:262-270 (2008).
NCBI GenBank: ACB38141.1, factor H-binding protein [Neisseria meningitidis] (Jun. 4, 2010).
NCBI GenBank: FJ184233.1, "Neisseria meningitidis factor H binding protein variant B09_004 (fhbp) gene, partial cds" (Aug. 4, 2009).
Prosecution history of U.S. Appl. No. 13/455,326, dated Apr. 26, 2013.

(Continued)

*Primary Examiner* — S. Devi
(74) *Attorney, Agent, or Firm* — Anna C. Chau

(57) ABSTRACT

The present invention relates to stable formulations of *Neisseria meningitis* rLP2086 Subfamily B Antigens in immunogenic compositions. The present invention also relates to methods of preserving the conformation of *Neisseria meningitis* rLP2086 Antigens and methods for determining the potency of *Neisseria meningitis* rLP2086 antigens.

4 Claims, 25 Drawing Sheets

(56) References Cited

U.S. PATENT DOCUMENTS

| | | |
|---|---|---|
| 6,281,337 B1 | 8/2001 | Cannon-Carlson et al. |
| 6,299,884 B1 | 10/2001 | Van Nest et al. |
| 6,355,253 B1 | 3/2002 | Zlotnick |
| 6,355,255 B1 | 3/2002 | Cleary et al. |
| 6,610,310 B2 | 8/2003 | Hilgers |
| 6,951,653 B2 | 10/2005 | Cleary et al. |
| 7,115,730 B1 | 10/2006 | Pizza et al. |
| 7,118,757 B1 | 10/2006 | Seid et al. |
| 7,285,281 B2 | 10/2007 | Green et al. |
| 7,291,588 B2 | 11/2007 | Pizza et al. |
| 7,332,174 B2 | 2/2008 | Green et al. |
| 7,361,355 B2 | 4/2008 | Green et al. |
| 7,384,640 B1 | 6/2008 | Holmes et al. |
| 7,576,176 B1 | 8/2009 | Fraser et al. |
| 7,608,278 B2 | 10/2009 | Hoiseth et al. |
| 7,785,608 B2 | 8/2010 | Zlotnick et al. |
| 7,803,387 B2 | 9/2010 | Arico et al. |
| 7,820,789 B2 | 10/2010 | Kirkham et al. |
| 8,039,007 B2 | 10/2011 | Rappuoli et al. |
| 8,101,194 B2 | 1/2012 | Zlotnick et al. |
| 8,273,360 B2 | 9/2012 | Pizza et al. |
| 8,398,988 B2 | 3/2013 | Contorni et al. |
| 8,563,006 B2 | 10/2013 | Zlotnick et al. |
| 8,563,007 B1 | 10/2013 | Zlotnick et al. |
| 8,574,597 B2 | 11/2013 | Zlotnick |
| 8,632,995 B2 | 1/2014 | Sun et al. |
| 8,834,888 B2 * | 9/2014 | Contorni ............ A61K 39/095 424/184.1 |
| 8,986,710 B2 | 3/2015 | Andersonon et al. |
| 9,107,873 B2 | 8/2015 | Zlotnick et al. |
| 9,132,182 B2 | 9/2015 | Zlotnick et al. |
| 2004/0110670 A1 | 6/2004 | Arico et al. |
| 2004/0167068 A1 | 8/2004 | Zlotnick et al. |
| 2004/0249125 A1 | 12/2004 | Pizza et al. |
| 2006/0251670 A1 | 11/2006 | Comanducci et al. |
| 2006/0257413 A1 | 11/2006 | Zlotnick et al. |
| 2007/0020622 A1 | 1/2007 | Lee et al. |
| 2007/0082007 A1 | 4/2007 | Zlotnick et al. |
| 2007/0148729 A1 | 6/2007 | Farley et al. |
| 2007/0253964 A1 | 11/2007 | Zlotnick et al. |
| 2009/0035328 A1 | 2/2009 | Granoff |
| 2009/0202593 A1 | 8/2009 | Zlotnick et al. |
| 2011/0076299 A1 | 3/2011 | Zlotnick et al. |
| 2011/0189187 A1 | 8/2011 | Zlotnick |
| 2011/0312510 A1 | 12/2011 | Mak et al. |
| 2012/0034261 A1 | 2/2012 | Zlotnick et al. |
| 2012/0070457 A1 | 3/2012 | Daugherty et al. |
| 2012/0093852 A1 | 4/2012 | Anderson et al. |
| 2012/0107339 A1 | 5/2012 | Granoff et al. |
| 2012/0301496 A1 | 11/2012 | Zlotnick et al. |
| 2013/0171194 A1 | 7/2013 | Khandke et al. |
| 2014/0113329 A1 | 4/2014 | Sun et al. |
| 2015/0071959 A1 | 3/2015 | Anderson et al. |
| 2015/0216960 A1 | 8/2015 | Zlotnick et al. |

FOREIGN PATENT DOCUMENTS

| | | |
|---|---|---|
| AU | 2007263531 | 1/2008 |
| CA | 2012311 C | 9/1990 |
| EP | 0125023 B1 | 11/1984 |
| EP | 0171496 B1 | 2/1986 |
| EP | 0173494 A2 | 3/1986 |
| EP | 0184187 A2 | 6/1986 |
| EP | 0185573 B1 | 6/1986 |
| EP | 0467714 A1 | 7/1991 |
| EP | 0178220 B1 | 1/1992 |
| EP | 0488528 B1 | 11/1995 |
| EP | 0453242 B1 | 8/1996 |
| EP | 1442047 | 8/2003 |
| EP | 1296713 B1 | 9/2003 |
| EP | 1326634 B1 | 4/2006 |
| EP | 2351767 A2 | 8/2011 |
| GB | 0121591.2 | 11/1918 |
| JP | 1144977 A | 6/1989 |
| WO | WO 86/01533 A1 | 3/1986 |
| WO | WO 87/01130 A1 | 2/1987 |
| WO | WO 87/02671 A1 | 5/1987 |
| WO | WO 89/07150 A1 | 8/1989 |
| WO | WO 90/02806 A1 | 3/1990 |
| WO | WO 90/10458 A1 | 9/1990 |
| WO | WO 91/18088 A1 | 11/1991 |
| WO | WO 92/05263 A1 | 4/1992 |
| WO | WO 92/19265 A1 | 11/1992 |
| WO | WO 93/09239 A1 | 5/1993 |
| WO | WO 94/12649 A2 | 6/1994 |
| WO | WO 94/21807 A2 | 9/1994 |
| WO | WO 94/26914 A1 | 11/1994 |
| WO | WO 94/28152 A1 | 12/1994 |
| WO | WO 94/28938 A1 | 12/1994 |
| WO | WO 95/02697 A1 | 1/1995 |
| WO | WO 95/07358 A1 | 3/1995 |
| WO | WO 95/18863 A1 | 7/1995 |
| WO | WO 95/21931 A1 | 8/1995 |
| WO | WO 95/22617 A1 | 8/1995 |
| WO | WO 95/26411 A2 | 10/1995 |
| WO | WO 95/28494 A1 | 10/1995 |
| WO | WO 96/10038 A1 | 4/1996 |
| WO | WO 96/14086 A1 | 5/1996 |
| WO | WO 96/17823 A1 | 6/1996 |
| WO | WO 96/22378 A1 | 7/1996 |
| WO | WO 96/25508 A1 | 8/1996 |
| WO | WO 96/29412 A1 | 9/1996 |
| WO | WO 96/39036 A1 | 12/1996 |
| WO | WO 96/40718 A1 | 12/1996 |
| WO | WO 97/19182 A1 | 5/1997 |
| WO | WO 98/08543 A1 | 3/1998 |
| WO | WO 98/08874 A1 | 3/1998 |
| WO | WO 98/17805 A2 | 4/1998 |
| WO | WO 99/01157 A1 | 1/1999 |
| WO | WO 99/01158 A1 | 1/1999 |
| WO | WO 99/01175 A1 | 1/1999 |
| WO | WO 99/10372 A1 | 3/1999 |
| WO | WO 99/24578 A2 | 5/1999 |
| WO | WO 99/27944 A1 | 6/1999 |
| WO | WO 99/36544 A2 | 7/1999 |
| WO | WO 99/40200 A1 | 8/1999 |
| WO | WO 99/48525 A1 | 9/1999 |
| WO | WO 99/55730 A2 | 11/1999 |
| WO | WO 99/55872 A1 | 11/1999 |
| WO | WO 99/57280 A2 | 11/1999 |
| WO | WO 99/61053 A1 | 12/1999 |
| WO | WO 00/18434 A1 | 4/2000 |
| WO | WO 00/22430 A2 | 4/2000 |
| WO | WO 00/42192 A1 | 7/2000 |
| WO | WO 00/43518 A1 | 7/2000 |
| WO | WO 00/44890 A1 | 8/2000 |
| WO | WO 00/45841 A2 | 8/2000 |
| WO | WO 00/50075 A2 | 8/2000 |
| WO | WO 00/57906 A1 | 10/2000 |
| WO | WO 00/66741 A2 | 11/2000 |
| WO | WO 00/66791 A1 | 11/2000 |
| WO | WO 00/71574 A2 | 11/2000 |
| WO | WO 00/71725 A2 | 11/2000 |
| WO | WO 01/04316 A2 | 1/2001 |
| WO | WO 01/31019 A2 | 5/2001 |
| WO | WO 01/37863 A2 | 5/2001 |
| WO | WO 01/38350 A2 | 5/2001 |
| WO | WO 01/41800 A3 | 6/2001 |
| WO | WO 01/52885 A1 | 7/2001 |
| WO | WO 01/64920 A2 | 9/2001 |
| WO | WO 01/64922 A2 | 9/2001 |
| WO | WO 02/058737 A2 | 8/2002 |
| WO | WO 02/079243 A2 | 10/2002 |
| WO | WO 02/079246 A2 | 10/2002 |
| WO | WO 02/083710 A2 | 10/2002 |
| WO | WO 02/083711 A2 | 10/2002 |
| WO | WO 02/098368 A2 | 12/2002 |
| WO | WO 02/098369 A2 | 12/2002 |
| WO | WO 03/007985 A2 | 1/2003 |
| WO | WO 03/009869 A1 | 2/2003 |
| WO | WO 03/020756 A2 | 3/2003 |
| WO | 03047619 | 6/2003 |
| WO | WO 03/063766 A2 | 8/2003 |

(56) References Cited

FOREIGN PATENT DOCUMENTS

| | | |
|---|---|---|
| WO | 03080678 A1 | 10/2003 |
| WO | 03094834 A2 | 11/2003 |
| WO | 03094960 A2 | 11/2003 |
| WO | 2004019977 A2 | 3/2004 |
| WO | 2004019992 A1 | 3/2004 |
| WO | WO 2004/032958 A1 | 4/2004 |
| WO | 2004046177 A2 | 6/2004 |
| WO | WO 2004/048404 A2 | 6/2004 |
| WO | 2004/065603 A2 | 8/2004 |
| WO | 2004067033 A1 | 8/2004 |
| WO | WO 2004/067030 A2 | 8/2004 |
| WO | WO 2004/083251 A2 | 9/2004 |
| WO | WO 2004/094596 A2 | 11/2004 |
| WO | 2005000345 A2 | 1/2005 |
| WO | 2005004908 A1 | 1/2005 |
| WO | 2005020964 A1 | 3/2005 |
| WO | 2005032583 A2 | 4/2005 |
| WO | 2005033148 A1 | 4/2005 |
| WO | 2005065708 A2 | 7/2005 |
| WO | 2005090985 A1 | 9/2005 |
| WO | 2005090986 A2 | 9/2005 |
| WO | 2005102384 A2 | 11/2005 |
| WO | 2005103230 A2 | 11/2005 |
| WO | 2005105140 A2 | 11/2005 |
| WO | 2005105141 A2 | 11/2005 |
| WO | WO 2005/108580 A1 | 11/2005 |
| WO | 2005113607 A2 | 12/2005 |
| WO | 2006000920 A2 | 1/2006 |
| WO | 2006011060 A2 | 2/2006 |
| WO | 2006027685 A2 | 3/2006 |
| WO | WO 2006/024954 A2 | 3/2006 |
| WO | 2006046143 A2 | 5/2006 |
| WO | 2006067632 A2 | 6/2006 |
| WO | 2006075170 A1 | 7/2006 |
| WO | WO 2006/081259 A2 | 8/2006 |
| WO | 2006096701 A2 | 9/2006 |
| WO | 2006120576 A2 | 11/2006 |
| WO | 2007000314 A2 | 1/2007 |
| WO | 2007000341 A2 | 1/2007 |
| WO | 2007000342 A2 | 1/2007 |
| WO | 2007000343 A2 | 1/2007 |
| WO | 2007026249 A2 | 3/2007 |
| WO | 2007028408 A1 | 3/2007 |
| WO | WO 2007/060548 A2 | 5/2007 |
| WO | 2007071786 A1 | 6/2007 |
| WO | 2007111940 A2 | 10/2007 |
| WO | 2007/127665 A2 | 11/2007 |
| WO | 2007127668 A2 | 11/2007 |
| WO | 2007144316 A2 | 12/2007 |
| WO | 2007144317 A2 | 12/2007 |
| WO | 2008001222 A2 | 1/2008 |
| WO | 2008013943 A2 | 1/2008 |
| WO | WO 2008/001224 A2 | 1/2008 |
| WO | 2008079372 A2 | 7/2008 |
| WO | 2008084411 A2 | 7/2008 |
| WO | 2008/149238 A2 | 12/2008 |
| WO | 2009010877 A2 | 1/2009 |
| WO | 2009016515 A2 | 2/2009 |
| WO | WO 2009/050586 A1 | 4/2009 |
| WO | WO 2009/104097 A2 | 8/2009 |
| WO | 2009109550 A1 | 9/2009 |
| WO | 2009114485 A2 | 9/2009 |
| WO | 2009143168 A2 | 11/2009 |
| WO | WO 2009/158142 A1 | 12/2009 |
| WO | 2010027872 A1 | 3/2010 |
| WO | 2010028096 A2 | 3/2010 |
| WO | 2010028859 A1 | 3/2010 |
| WO | 2010067202 A2 | 6/2010 |
| WO | 2010070453 A2 | 6/2010 |
| WO | 2010109324 A1 | 9/2010 |
| WO | WO 2010/109323 A1 | 9/2010 |
| WO | 2010127172 A2 | 11/2010 |
| WO | 2011024072 A2 | 3/2011 |
| WO | 2011039631 A2 | 4/2011 |
| WO | 2011042516 A2 | 4/2011 |
| WO | 2011051893 A1 | 5/2011 |
| WO | 2011080595 A2 | 7/2011 |
| WO | 2011110531 A2 | 9/2011 |
| WO | 2011110634 A2 | 9/2011 |
| WO | 2011110635 A1 | 9/2011 |
| WO | 2011126863 A1 | 10/2011 |
| WO | WO 2011/161653 A1 | 12/2011 |
| WO | 2012020326 A1 | 2/2012 |
| WO | 2012025873 A2 | 3/2012 |
| WO | 2012031271 A1 | 3/2012 |
| WO | 2012032169 A1 | 3/2012 |
| WO | 2012032489 A1 | 3/2012 |
| WO | 2012032498 A2 | 3/2012 |
| WO | 2012035519 A1 | 3/2012 |
| WO | 2013132452 A2 | 9/2013 |
| WO | 2014136064 A2 | 9/2014 |
| WO | 2015033251 A2 | 3/2015 |

OTHER PUBLICATIONS

Rosenstein et al, "Meningococcal Vaccines", Infectious Disease Clinics of North America 15(1):155-169 (2001).

Tondella et al, "Distribution of Neisseria meningitidis Serogroup B Serosubtypes and Serotypes Circulating in the United States", Journal of Clinical Microbiology 38(9):3323-3328 (2000).

U.S. Pat. No. 8,398,988 B2 Prosecution History (Feb. 23, 2012-Feb. 27, 2013).

Aasel et al., "Most antibodies to PorB and Rmp do not bind to viable meningococci, but bind strongly to ethanol-killed bacteria", Abstract from the 11th International Pathogenic Neisseria Conference (Nice France, Nov. 1-6, 1998), pp. 37-38 (http://neisseria.org/ipnc/history.shtml).

Abdillahi et al, "Whole-cell ELISA for typing Neisseria meningitidis with monoclonal antibodies", FEMS Microbiology Letters 48:367-371 (1987).

Abdillahi et al, "Neisseria meningitidis group B serosubtyping using monoclonal antibodies in whole-cell Elisa", Microbial Pathogenesis 4:27-32 (1988).

Achtman, "Epidemic spread and antigenic variability of Neisseria meningitidis", Trends in Microbiology 3(5):186-192 (1995).

Alm et al, "Genomic-sequence comparison of two unrelated isolates of the human gastric pathogen *Helicobacter pylori* ", Nature 397:176-180 (1999).

Altschul et al, "Basic Local Alignment Search Tool", J. Mol. Biol. 215:403-410 (1990).

Altschul et al, "Protein database searches for multiple alignments", Proc. Natl. Acad. Sci. 87:5509-5513 (1990).

Altschul et al, "Gapped BLAST and PSI-BLAST: a new generation of protein database search programs", Nucleic Acids Research 25(17): 3389-3402 (1997).

Ambrosch et al, "Immunogenicity and side-effects of a new tetravalent meningococcal polysaccharide vaccine", Bulletin of the World Health Organization 61(2):317-323 (1983).

Anderson, "Techniques for the preservation of three-dimensional structure in preparing specimens for the electron microscope", Transactions of the New York Academy of Sciences, 13:130-134 (1951).

Bantam Medical Dictionary, Third Edition, pp. 302-303 (2000).

Barbour et al, "New tricks of tick-borne pathogen", Nature 390:553 & 555 (1997).

Bateman et al, "The Pfam Protein Families Database", Nucleic Acids Research 28(1):263-266 (2000).

Beard et al, "Transcription Mapping of Mouse Adenovirus Type 1 Early Region 3", Virology 175:81-90 (1990).

Bender et al, "Evidence that the Packaging Signal of Moloney Murine Leukemia Virus Extends into the gag Region", Journal of Virology 61(5):1639-1646 (1987).

Benson, "Tandem repeats finder: a program to analyze DNA sequences", Nucleic Acids Research 27(2):573-580 (1999).

Bernfield et al., "Identification of a novel vaccine candidate for group B Neisseria meningitidis", Abstracts of the Thirteenth International Pathogenic Neisseria Conference, (Ed) Caugant et al. Oslo, Norway, p. 116, Sep. 1-6, 2002.

(56) References Cited

OTHER PUBLICATIONS

Bernstein et al, "Gene Transfer with Retrovirus Vectors", Genet. Eng. 7:235-261 (1985).
Better et al, *Escherichia coli* Secretion of an Active Chimeric Antibody Fragment, Science 240:1041-1043 (1988).
Beuvery et al, "Preparation and Immunochemical Characterization of Meningococcal Group C Polysaccharide-Tetanus Toxoid Conjugates as a New Generation of Vaccines", Infection and Immunity 40(1):39-45 (1983).
Beuvery et al, "Preparation and Physicochemical and Immunological Characterization of Polysaccharide-Outer Membrane Protein Complexes of Neisseria meningitidis", Infection and Immunity 40(1):369-380 (1983).
Biocomputing: Informatics and Genome Projects, Smith D.W., ed., Academic Press, New York (1994).
Bjune, et al., "Effect of Outer Membrane Vesicle Vaccine Against Group B Meningococcal Disease in Norway", The Lancet, 338(8775):1093-1096 (1991).
Boslego et al, "Chapter 17: Gonorrhea Vaccines", Vaccines and Immunotherapy, SJ Cryz Jr. ed., Pergamon Press, pp. 211-223 (1991).
Boulianne et al, "Production of functional chimaeric mouse/human antibody", Nature 312:643-646 (1984).
Brown, "Hybridization Analysis of DNA Blots", Current Protocols in Molecular Biology, Supp. 21, 2.10.1-2.10.16 (1993).
Cabilly et al, "Generation of antibody activity from immunoglobulin polypeptide chains produced in *Escherichia coli* ", Proc. Natl. Acad. Sci. 81:3273-3277 (1984).
Cannon, "Conserved Lipoproteins of Pathogenic Neisseria Species Bearing the H.8 Epitope: Lipid-Modified Azurin and H.8 Outer Membrane Protein", Clinical Microbiology Reviews 2(Suppl):S1-S4 (1989).
Cantini et al, "Solution Structure of the Immunodominant Domain of Protective Antigen GNA1870 of Neisseria meningitidis", The Journal of Biological Chemistry 281(11):7220-7227 (2006).
Carillo et al, "The Multiple Sequence Alignment Problem in Biology", SIAM J. Appl. Math. 48(5):1073-1082 (1988).
Chao et al, "Endocarditis due to Neisseria sicca: Report of One Case", Acta Paed Sin 38(3):229-231 (1997).
Chen et al, "Cloning and Expression of the Streptococcal C5a Peptidase Gene in *Escherichia coli* : Linkage to the Type 12 M Protein Gene", Infection and Immunity 57(6):1740-1745 (1989).
Chen et al., "Determination of the Optimal Aligned Spacing Between the Shine-Dalgarno Sequence and the Translation Initiation Codon of *Escherichia coli* mRNAs", Nucleic Acids Research 22(23):4953-4957 (1994).
Chmouryguina et al, "Conservation of the C5a Peptidase Genes in Group A and B Streptococci", Infection and Immunity 64(7):2387-2390 (1996).
Cockerill et al, "Molecular, Serological, and Clinical Features of 16 Consecutive Cases of Invasive Streptococcal Disease", Clinical Infectious Diseases 26:1448-1458 (1998).
Computational Molecular Biology: Sources and Methods for Sequence Analysis, Lesk A.M. et., Oxford University Press, New York, 1988.
Courtney et al, "Cloning, Sequencing, and Expression of a Fibronectin/Fibrinogen-Binding Protein from Group A Streptococci", Infection and Immunity 62(9):3937-3946 (1994).
Cserzo et al, "Prediction of transmembrane alpha-helices in prokaryotic membrane proteins: the dense alignment surface method", Protein Engineering 10(6):673-676 (1997).
Cunningham et al, "Immunological Crossreactivity Between the Class I Epitope of Streptococcal M Protein and Myosin", Adv Exp Med Biol 418:887-892 (1997).
Curiel et al, "High-Efficiency Gene Transfer Mediated by Adenovirus Coupled to DNA-Polylysine Complexes", Human Gene Therapy 3:147-154 (1992).
Curriculum Vitae of Professor Paul M. Dunman, Ph.D., submitted in Opposition Proceedings against Novartis EP 1 645 631 on Sep. 14, 2011.

Curriculum Vitae of Lakshmi Khandke, Ph.D., submitted in Opposition Proceedings against Novartis EP1409013 on Nov. 18, 2011.
Dale et al, "Passive Protection of Mice Against Group A Streptococcal Pharyngeal Infection by Lipoteichoic Acid", The Journal of Infectious Diseases 169:319-323 (1994).
Dale et al, "Hyaluronate Capsule and Surface M Protein in Resistance to Opsonization of Group A Streptococci", Infection and Immunity 64(5):1495-1501 (1996).
Dale et al, "Recombinant, octavalent group A streptococcal M protein vaccine", Vaccine 14(10):944-948 (1996).
Database EMBL [Online] Ebi, Kohara, Y., "Caenorhabditis elegans cDNA clone yk26f2: 5' end, single read," Database accession No. D35881 (Aug. 13, 1994).
Database Geneseq 'Online', "Neisseria meningitidis ORF 741 protein sequence SEQ ID No. 2536", XP002320506, Mar. 21, 2000.
Database Geneseq 'Online', "N. gonorrhoeae amino acid sequence SEQ ID 1586", XP002320505, Mar. 7, 2003.
Database Geneseq Online, "Neisseria meningitides ORF2086 protein-encoding gene SedID61" AAY75530, Jan. 29, 2004.
Database Geneseq Online, "Neisseria meningitides ORF2086 protein-encoding gene SedID61" AAZ54292-NT, Jan. 29, 2004.
Datasheet for MENCEVAX™, International Data Sheet version 2.1 (Dec. 5, 2000).
Declaration of Emilio A. Emini, Ph.D., submitted in Opposition Proceedings against Novartis EP1645631 on Nov. 3, 2011.
Declaration of Lakshmi Khandke, Ph.D., submitted in Opposition Proceedings against Novartis EP1409013 on Dec. 21, 2011.
Definition of "epitope" from Henderson's Dictionary of Biological Terms, 11th edition, Eleanor Lawrence ed., pp. 37, 184 and cover pages. (1997).
Devereux et al, "A comprehensive set of sequence analysis programs for the VAX", Nucleic Acids Research 12 (1):387-395 (1984).
Erdile et al, "Role of Attached Lipid in Immunogenicity of Borrelia burgdorferi OspA", Infection and Immunity 61 (1):81-90 (1993).
Fletcher et al, "Vaccine Potential of the Neisseria meningitidis 2086 Lipoprotein", Infection and Immunity 72 (4):2088-2100 (2004).
Fogg et al,"Constitutive Expression of Fibronectin Binding in *Streptococcus* pyogenes as a Result of Anaerobic Activation of rofA", Journal of Bacteriology 179(19):6172-6180 (1997).
Fontana et al, "A genomic approach to identify vaccine candidates against gonococcus", Abstract from the 13th International Pathogenic Neisseria Conference, Oslo Norway, Sep. 1-6 2002, p. 248 (http://neisseria.org/ipnc/history.shtml).
GenBank No. EF108319.1, O'Leary, M. M. et al., Neisseria meningitidis strain NM452 FHBP/GNA1870 variant (GNA1870) gene, complete cds, Nov. 8, 2006, accessed Sep. 5, 2012.
Gomez et al, "The Bacillus subtilis lipoprotein LpIA causes cell lysis when expressed in *Escherichia coli*", Microbiology 140:1839-1845 (1994).
Gupta, "Aluminum compounds as vaccine adjuvants", Advanced Drug Delivery Reviews 32(3):155-172 (1998).
Guzman et al, "Tight Regulation, Modulation, and High-Level Expression by Vectors Containing the Arabinose PBAD Promoter", Journal of Bacteriology 177(14):4121-4130 (1995).
Hacker et al, "Pathogenicity islands of virulent bacteria: structure, function and impact on microbial evolution", Molecular Microbiology 23(6):1089-1097 (1997).
Hanski et al, "Expression of protein F, the fibronectin-binding protein of *Streptococcus pyogenes* JRS4, in heterologous streptococcal and enterococcal strains promotes their adherence to respiratory epithelial cells", Infection and Immunity 60(12):5119-5125 (1992).
Hanski et al, "Protein F, a fibronectin-binding protein, is an adhesin of the group A streptococcus *Streptococcus pyogenes* ", Proc. Natl. Acad. Sci. 89:6172-6176 (1992).
Hansson et al, "Expression of Truncated and Full-Length Forms of the Lyme Disease Borrelia Outer Surface Protein A in *Escherichia coli* ", Protein Expression and Purification 6:15-24 (1995).
Hayashi et al, "Lipoproteins in Bacteria", Journal of Bioenergetics and Biomembranes 22(3):451-471 (1990).

(56) References Cited

OTHER PUBLICATIONS

Hem et al, "Chapter 9: Structure and Properties of Aluminum-Containing Adjuvants", Vaccine Design: The Subunit and Adjuvant Approach, Plenum Press, New York, pp. 249-276 (1995).
Hernandez-Sanchez et al, "lambda bar minigene-mediated inhibition of protein synthesis involves accumulation of peptidyl-tRNA and starvation for tRNA", The EMBO Journal 17(13):3758-3765 (1998).
Hornyik et al, "Cerebrospinal Fluid Shunt Infection by Neisseria sicca", Pediatr Neurosurg 21:189-191 (1994).
Houghten, "General Method for the rapid solid-phase synthesis of large numbers of peptides: Specificity of antigen-antibody interaction at the level of individual amino acids", Proceedings of the National Academy of Sciences of USA 82:5131-5135 (1985).
Huang et al, "The streptokinase gene of group A streptococci: cloning, expression in *Escherichia coli*, and sequence analysis", Molecular Microbiology 3(2):197-205 (1989).
Hung, "The Neisseria meningitidis Macrophage Infectivity Potentiator Protein Induces Cross-Strain Serum Bactericidal Activity and is a Potential Serogroup B Vaccine Candidate", Infection and Immunity, 79(9):3784-3791 (2011).
Hynes et al, "Analysis of a Second Bacteriophage Hyaluronidase Gene from *Streptococcus pyogenes* : Evidence for a Third Hyaluronidase Involved in Extracellular Enzymatic Activity", Infection and Immunity 63(8):3015-3020 (1995).
Hynes et al, "The extracellular hyaluronidase gene (hylA) of *Streptococcus pyogenes*", FEMS Microbiology Letters 184:109-112 (2000).
Interlocutory Decision of the Opposition Division in Opposition against Novartis EP 1 645 631 dated May 21, 2012.
Isberg et al, "Binding and internalization of microorganisms by integrin receptors", Trends in Microbiology 2(1):10-14 (1994).
Jackson et al, U.S. Appl. No. 60/098,685, filed Sep. 1, 1998.
Jiang et al, "Broad vaccine coverage predicted for a bivalent recombinant factor H binding protein based vaccine to prevent serogroup B meningococcal disease", Vaccine 28:6086-6093 (2010).
Johnson et al., "Analysis of the Human Ig Isotype Response to Lactoferrin Binding Protein A from Neisseria meningitidis", FEMS Immunology and Medical Microbiology 25(4):349-354 (1999).
Jones et al, "The Importance of the Location of Antibody Binding on the M6 Protein for Opsonization and Phagocytosis of Group A M6 Streptococci", J. Exp. Med. 167:1114-1123 (1988).
JVCI-CMR website showing Z2491 Sanger sequence (http://cmr.jvci.org/tigr-scripts/CMR/shared/Genomes.cgi and links) printed on Jul. 1, 2010.
Kafri et al, "A Packaging Cell Line for Lentivirus Vectors", Journal of Virology 73(1):576-584 (1999).
Kaplitt et al, "Expression of a Functional Foreign Gene in Adult Mammalian Brain following in Vivo Transfer via a Herpes Simplex Virus Type 1 Defective Viral Vector", Molecular and Cellular Neurosciences 2:320-330 (1991).
Kihlberg et al, "Protein H, an Antiphagocytic Surface Protein in *Streptococcus pyogenes* ", Infection and Immunity 67 (4):1708-1714 (1999).
Klein et al, "Distinctive properties of signal sequences from bacterial lipoproteins", Protein Engineering 2(1):15-20 (1988).
Koebnik, "Proposal for a peptidoglycan-associating alpha-helical motif in the C-terminal regions of some bacterial cell-surface proteins", Molecular Microbiology 16(6):1269-1270 (1995).
Kohler et al, "Continuous cultures of fused cells secreting antibody of predefined specificity", Nature 256:495-497 (1975).
Kuipers et al, "Improved site-directed mutagenesis method using PCR", Nucleic Acids Research 19(16):4558 (1991).
Kuo et al, "Efficient Gene Transfer into Primary Murine Lymphocytes Obviating the Need for Drug Selection", Blood 82(3):845-852 (1993).
Kyte et al, "A Simple Method for Displaying the Hydropathic Character of a Protein", J. Mol. Biol. 157:105-132 (1982).
Landt et al, "A general method for rapid site-directed mutagenesis using the polymerase chain reaction", Gene 96:125-128 (1990).
Lasalle et al, "An Adenovirus Vector for Gene Transfer into Neurons and Glia in the Brain", Science 259:988-990 (1993).
Lebkowski et al, "Adeno-Associated Virus: a Vector System for Efficient Introduction and Integration of DNA into a Variety of Mammalian Cell Types", Molecular and Cellular Biology 8(10):3988-3996 (1988).
Levrero et al, "Defective and nondefective adenovirus vectors for expressing foreign genes in vitro and in vivo", Gene 101:195-202 (1991).
Liu et al, "Chimeric mouse-human IgG1 antibody that can mediate lysis o f cancer cells", Proc. Natl. Acad. Sci. 84:3439-3443 (1987).
Loessner et al, "Evidence for a Holin-Like Protein Gene Fully Embedded Out of Frame in the Endolysin Gene of *Staphylococcus aureus* Bacteriophage 187", Journal of Bacteriology 181(15):4452-4460 (1999).
Lukashin et al, "GeneMark.hmm: new solutions for gene finding", Nucleic Acids Research 26(4):1107-1115 (1998).
Lukomski et al, "Extracellular Cysteine Protease Produced by *Streptococcus pyogenes* Participates in the Pathogenesis of Invasive Skin Infection and Dissemination in Mice", Infection and Immunity 67(4):1779-1788 (1999).
Lunn et al, "Effects of Prolipoprotein Signal Peptide Mutations on Secretion of Hybrid Prolipo-beta-lactamase in *Escherichia coli* ", The Journal of Biological Chemistry 262(17):8318-8324 (1987).
Machy et al, "Gene transfer from targeted liposomes to specific lymphoid cells by electroporation", Proc. Natl. Acad. Sci. 85:8027-8031 (1988).
Madore, "Characterization of immune response as an indicator of Haemophilus influenzae type b vaccine efficacy", The Pediatric Infectious Disease Journal 17(9):Supplement:S207-S210 (1998).
Mann, et al, "Construction of a Retrovirus Packaging Mutant and Its Use to Produce Helper-Free Defective Retrovirus", Cell 33:153-159 (1983).
Markowitz et al, "A Safe Packaging Line for Gene Transfer: Separating Viral Genes on Two Different Plasmids", Journal of Virology 62(4):1120-1124 (1988).
Martin et al, "Highly Conserved Neisseria meningitidis Surface Protein Confers Protection against Experimental Infection", J. Exp. Med. 185(7):1173-1183 (1997).
Masignani et al, "Vaccination against Neisseria meningitidis Using Three Variants of the Lipoprotein GNA1870", The Journal of Experimental Medicine 197(6):789-799 (2003).
Matsuka et al, "Fibrinogen Cleavage by the *Streptococcus pyogenes* Extracellular Cysteine Protease and Generation of Antibodies That Inhibit Enzyme Proteolytic Activity", Infection and Immunity 67(9):4326-4333 (1999).
Mazmanian et al, "*Staphylococcus aureus* Sortase, an Enzyme that Anchors Surface Proteins to the Cell Wall", Science 285:760-763 (1999).
McAtee et al, "Characterization of a Helicobacter pylori vaccine candidate by proteome techniques", Journal of Chromatography B, Biomedical Sciences and Applications 714:325-333 (1998).
McAtee et al, "Identification of Potential Diagnostic and Vaccine Candidates of Helicobacter pylori by "Proteome" Technologies", Helicobacter 3(3):163-169 (1998).
McAtee et al, "Identification of Potential Diagnostic and Vaccine Candidates of Helicobacter pylori by Two-Dimensional Gel Electrophoresis, Sequence Analysis, and Serum Profiling", Clinical and Diagnostic Laboratory Immunology 5(4):537-542 (1998).
McCormick, "Human Gene Therapy: The First Round", BioTechnology 3(8):689-693 (1985).
McGuinness et al, "Class 1 outer membrane protein of Neisseria meningitidis: epitope analysis of the antigenic diversity between strains, implications for subtype definition and molecular epidemiology", Molecular Microbiology 7 (4):505-514 (1993).
Mejlhede et al, "Ribosomal-1 Frameshifting during Decoding of Bacillus subtilis cdd Occurs at the Sequence CGA AAG", Journal of Bacteriology 181(9):2930-2937 (1999).
Milagres et al., "Specificity of Bactericidal Antibody Response to Serogroup B Miningococcal Strains in Brazilian Children after

(56) References Cited

OTHER PUBLICATIONS

Immunization with an Outer Membrane Vaccine", Infection and Immunity 66(10):4755-4761 (1998).
Miller et al, "Improved Retroviral Vectors for Gene Transfer and Expression", BioTechniques 7(9):980-990 (1992).
Minutes of Oral Proceedings in Opposition against Novartis EP 1 645 631 dated Mar. 5, 2012.
Mir et al, "Long-term, high level in vivo gene expression after electric pulse-mediated gene transfer into skeletal muscle", Academie des sciences 321:893-899 (1998).
Molinari et al, "The Fibronectin-Binding Protein of *Streptococcus pyogenes*, Sfbl, Is Involved in the Internalization of Group A Streptococci by Epithelial Cells", Infection and Immunity 65(4):1357-1363 (1997).
Morbidity and Mortality Weekly Report (MMWR), Recommendations and Reports, Case Definitions for Infectious Conditions Under Public Health Surveillance, May 2, 1997, vol. 46, No. RR-10.
Moreno et al, "Immunity and Protection of Mice Against Neisseria meningitidis Group B by Vaccination, Using Polysaccharide Complexed with Outer Membrane Proteins: A Comparison with Purified B Polysaccharide", Infection and Immunity 47(2):527-533 (1985).
Morley et al, "Vaccine prevention of meningococcal disease, coming soon?", Vaccine 20:666-687 (2002).
Morrison et al, "Chimeric human antibody molecules: Mouse antigen-binding domains with human constant region domains", Proc. Natl. Acad. Sci. 81:6851-6855 (1984).
Mountzouros et al, "Detection of Complement-Mediated Antibody-Dependent Bactericidal Activity in a Fluorescence-Based Serum Bactericidal Assay for Group B Neisseria meningitidis", Journal of Clinical Microbiology 38 (8):2878-2884 (2000).
Moxon, "Applications of molecular microbiology to vaccinology," Lancet 350(9086):1240-1244 (1997).
Munkley et al., "Blocking of Bactericidal Killing of Neisseria meningitidis by Antibodies Directed Against Class 4 Outer Membrane Protein", Microbial Pathogenesis 11:447-452 (1991).
Murphy et al, "Sequence Diversity of the Factor H Binding Protein Vaccine Candidate in Epidemiologically Relevant Strains of Serogroup B Neisseria meningitidis" The Journal of Infectious Diseases 200:379-389 (2009).
Nakai et al, "Expert System for Predicting Protein Localization Sites in Gram-Negative Bacteria", Proteins: Structure, Function, and Genetics 11:95-110 (1991).
Naldini et al, "Lentiviruses as gene transfer agents for delivery to non-dividing cells", Current Opinion in Biotechnology 9:457-463 (1998).
Nassif, "A Furtive Pathogen Revealed", Science 287:1767-1768 (2000).
Navarre et al, "Surface Proteins of Gram-Positive Bacteria and Mechanisms of Their Targeting to the Cell Wall Envelope", Microbiology and Molecular Biology Reviews 63(1):174-229 (1999).
Neisseria gonorrhoeae FA 1090 chromosome Entire clone gono strain FA1090, complete sequence. GenBank Accession gono AE004969, 2153894 bp, Sep. 26, 2000.
Nielsen et al, "Identification of prokaryotic and eukaryotic signal peptides and prediction of their cleavage sites", Protein Engineering 10(1):1-6 (1997).
Nizet et al, "Genetic Locus for Streptolysin S Production by Group A *Streptococcus* ", Infection and Immunity 68 (7):4245-4254 (2000).
Nordstrand et al, "Allele Substitution of the Streptokinase Gene Reduces the Nephritogenic Capacity of Group A Streptococcal Strain NZ131", Infection and Immunity 68(3):1019-1025 (2000).
Notice of Opposition against Novartis EP 1 645 631 submitted Jul. 23, 2008.
Novartis submits Bexsero®, a multi-component meningococcal B vaccine, for regulatory review in Europe, Novartis Media Release (Dec. 23, 2010).
Olmsted et al, "High-Resolution Visualization by Field Emission Scanning Electron Microscopy of Enterococcus faecalis Surface Proteins Encoded by the Pheromone-Inducible Conjugative Plasmid pCF10", Journal of Bacteriology 175(19):6229-6237 (1993).
Opponent's Further Submission in Preparation of Oral Proceedings in Opposition against Novartis EP 1 645 631 submitted Nov. 3, 2011.
Oudega et al, "A lipoprotein signal peptide plus a cysteine residue at the amino-terminal end of the periplasmic proteins beta-lactamase is sufficient for its lipid modification, processing and membrane localization in *Escherichia coli*", FEMS Microbiology Letters 108:353-360 (1993).
Oudega et al, "*Escherichia coli* SecB, SecA, and SecY Proteins Are Required for Expression and Membrane Insertion of the Bacteriocin Release Protein, a Small Lipoprotein", Journal of Bacteriology 175(5):1543-1547 (1993).
Pannekoek et al, "Construction of recombinant neisserial Hsp60 proteins and mapping of antigenic domains", Molecular Microbiology 15(2):277-285 (1995).
Park et al, "DIVCLUS: an automatic method in the GEANFAMMER package that finds homologous domains in single- and multi-domain proteins", Bioinformatics 14(2):144-150 (1998).
Parkhill, "Campylobacter jejuni genome sequence at the Sanger Centre", (May 8, 1998), available at: http://www.bio.net/bionet/mm/bionews/1997-May/00442.html.
Parkhill et al, "Complete DNA sequence of a serogroup A strain of Neisseria meningitidis Z2491", Nature 404:502-506 (2000).
Patentees' Further Submission Under Rule 116 EPC in Opposition against Novartis EP 1 645 631 submitted Oct. 14, 2011.
Patentees' Response to Opposition against Novartis EP 1 645 631 submitted May 8, 2009.
Patentees' Submissions Under Rule 116 EPC in Opposition against Novartis EP 1 645 631 submitted Sep. 13, 2011.
PCT Annex to Form PCT/ISA/206 Communication Relating to the Results of the Partial International Search, PCT/US2007/026238.
PCT International Search Report for PCT/US2007/026238 issued Feb. 23, 2009.
Perrett et al, "Towards an improved serogroup B Neisseria meningitidis vaccine", Expert Opin. Biol. Ther. 5 (12):1611-1625 (2005).
Pettersson, et al., "The meningococcal lactoferrin receptor", IPNC Abstract (1998).
Pettersson et al., "Vaccine potential of the Neisseria meningitidis Lactoferrin-binding Proteins LbpA and LbpB", Vaccine, 24(17):3545-3557 (2006).
Phase II clinical results for Novartis vaccine, Novartis Media Release (Oct. 9, 2008).
Phillips, "The challenge of gene therapy and DNA delivery", Journal of Pharmacy and Pharmacology 53:1169-1174 (2001).
Pierschbacher et al, "Influence of Stereochemistry of the Sequence Arg-Gly-Asp-Xaa on Binding Specificity in Cell Adhesion", The Journal of Biological Chemistry 262(36):17294-17298 (1987).
Pizza et al, "Identification of Vaccine Candidates Against Serogroup B Meningococcus by Whole-Genome Sequencing", Science 287:1816-1820 (2000).
Pizza, Preparation of Meningococcal Antigens (2005), available at: http://cordis.europa.eu/search/index.cfm?fuseaction=result.document&RS LANG=EN&RS RCN=7461241&q=.
Podbielski et al, "The Group A Streptococcal virR49 Gene Controls Expression of Four Structural vir Regulon Genes", Infection and Immunity 63(1):9-20 (1995).
Pollitt et al, "Effect of Amino Acid Substitutions at the Signal Peptide Cleavage Site of the *Escherichia coli* Major Outer Membrane Lipoprotein", The Journal of Biological Chemistry 261(4):1835-1837 (1986).
Poolman et al, "Colony variants of Neisseria meningitidis strain 2996 (B-2b:P1.2): influence of class-5 outer membrane proteins and lipopolysaccharides", J Med Microbiol 19(2):203-209 (1985).
Poolman, "Development of a meningococcal vaccine," Infectious Agents and Disease 4(1):13-28 (1995).
Poolman, "Bacterial Outer Membrane Protein Vaccines: The Meningococcal Example", Advances in Experimental Medicine & Biology 397:73-77 (1996).
Preliminary Opinion of the Opposition Division in Opposition against Novartis EP 1 645 631 dated Jun. 24, 2011.

(56) References Cited

OTHER PUBLICATIONS

Proft et al, "Identification and Characterization of Novel Superantigens from *Streptococcus pyogenes* ", J. Exp. Med. 189(1):89-101 (1999).
Progress through the Sanger Institute FTP Server, submitted in Opposition Proceedings against Novartis EP1645631 on May 8, 2009.
PSORT analysis of 200 of the sequences disclosed in PCT/US99/09346, submitted in Opposition Proceedings against Novartis EP1645631 on May 25, 2010.
PSORT analysis of SEQ ID Nos. 4 and 6, and of 'Contig295' 300mer, submitted in Opposition Proceedings against Novartis EP1645631 on May 8, 2009.
PSORT prediction result for SEQ ID No. 2, submitted in Opposition Proceedings against Novartis EP1645631 on May 25, 2010.
Pugsley, "The Complete General Secretory Pathway in Gram-Negative Bacteria", Microbiological Reviews 57 (1):50-108 (1993).
Quinn et al, "Immunological Relationship between the Class I Epitope of Streptococcal M Protein and Myosin", Infection and Immunity 66(9):4418-4424 (1998).
Random House Dictionary, Random House, New York, p. 546 (1984).
Reda et al, "Phylogenetic Distribution of Streptococcal Superantigen SSA Allelic Variants Provides Evidence for Horizontal Transfer of ssa within *Streptococcus pyogenes* ", Infection and Immunity 64(4):1161-1165 (1996).
Rinaudo et al, "Vaccinology in the genome era", The Journal of Clinical Investigation, 119(9):2515-2525 (2009).
Romero et al, "Current Status of Meningococcal Group B Vaccine Candidates: Capsular or Noncapsular?" Clinical Microbiology Reviews 7(4):559-575 (1994).
Ross, et al., "Identification of Vaccine Candidate Antigens from a Genomic Analysis of Porphyromonas gingivalis", Vaccine 19:4135-4142 (2001).
Sahagan et al, "A Genetically Engineered Murine/Human Chimeric Antibody Retains Specificity for Human Tumor-Associated Antigen", The Journal of Immunology 137(3):1066-1074 (1986).
Salzberg et al, "Microbial gene identification using interpolated Markov models", Nucleic Acids Research 26 (2):544-548 (1998).
Sambrook et al, "Analysis and Cloning of Eukaryotic Genomic DNA", Molecular Cloning: A Laboratory Manual, Second Edition, Cold Spring Harbor Laboratory Press, Cold Spring Harbor, New York, Chapter 9, pp. 9.1-9.62 (1989).
Sambrook et al, "Synthetic Oligonucleotide Probes", Molecular Cloning: A Laboratory Manual, Second Edition, Cold Spring Harbor Laboratory Press, Cold Spring Harbor, New York, Chapter 11, pp. 11.1-11.61 (1989).
Sambrook et al, Molecular Cloning: A Laboratory Manual, Third Edition, Cold Spring Harbor Laboratory Press, Cold Spring Harbor, New York (2001).
Samulski et al, "A Recombinant Plasmid from Which an Infectious Adeno-Associated Virus Genome Can Be Excised In Vitro and Its Use to Study Viral Replication", Journal of Virology 61(10):3096-3101 (1987).
Samulski et al, "Helper-Free Stocks of Recombinant Adeno-Associated Viruses: Normal Integration Does Not Require Viral Gene Expression", Journal of Virology 63(9):3822-3828 (1989).
Sanger Centre FTP files [online] URL: ftp://ftp.sanger.ac.uk/pub/pathogens/nm/, dated Jul. 23, 2008.
Sanger Centre's "Projects" website as of Dec. 10, 1997 as retrievable via http://web.archive.org, accessed Mar. 15, 2010.
Sankaran et al, "Modification of Bacterial Lipoproteins", Methods in Enzymology 250:683-697 (1995).
Saukkonen et al, "Protective efficacy of monoclonal antibodies to class 1 and class 3 outer membrane proteins of Neisseria meningitidis B:15:P1.16 in infant rat infection model: new prospects for vaccine development", Microbial Pathogenesis 3:261-267 (1987).
Sedegah et al, "Protection against malaria by immunization with plasmid DNA encoding circumsporozoite protein", Proc. Natl. Acad. Sci. 91:9866-9870 (1994).
Sedegah et al, "Improving Protective Immunity Induced by DNA-Based Immunization: Priming with Antigen and GM-CSF-Encoding Plasmid DNA and Boosting witih Antigen-Expressing Recombinant Poxvirus", The Journal of Immunology 164:5905-5912 (2000).
Sepelyak et al, "Adsorption of Pepsin by Aluminum Hydroxide I: Adsorption Mechanism", Journal of Pharmaceutical Sciences 73(11):1514-1517 (1984).
Sequence Analysis Primer, Gribskov and Devereux, eds., M Stockton Press, New York 1991.
Sequence Analysis in Molecular Biology. Treasure Trove or Trivial Pursuit, Gunnar von Heijne, Academic Press (1987).
Sequence for "Putative Lipoprotein [Neisseria Meningitidis Z2491]", NCBI Reference Sequence:YP_002342062.1, dated May 6, 2009, accessed Aug. 4, 2009.
Serruto et al, "Genome-based approaches to develop vaccines against bacterial pathogens", Vaccine 27:3245-3250 (2009).
Smith et al., "Nucleotide sequence determination and genetic analysis of the bacteroides plasmid, pBI143," Plasmid 34(3):211-222 (1995).
Snapper et al, "Bacterial Lipoproteins May Substitute for Cytokines in the Humoral Immune Response to T Cell-Independent Type II Antigens", The Journal of Immunology 155:5582-5589 (1995).
Snapper et al, "IL-3 and Granulocyte-Macrophage Colony-Stimulating Factor Strongly Induce Ig secretion by Sort-Purified Murine B Cells Activated Through the Membrane Ig, but Not the CD40, Signaling Pathway", The Journal of Immunology 154:5842-5850 (1995).
Sonnenberg et al, "Definition of *Mycobacterium tuberculosis* Culture Filtrate Proteins by Two-Dimensional Polyacrylamide Gel Electrophoresis, N -Terminal Amino Acid Sequencing, and Electrospray Mass Spectrometry", Infection and Immunity 65(11):4515-4524 (1997).
Sonnhammer et al, "Pfam: A Comprehensive Database of Protein Domain Families Based on Seed Alignments", Proteins: Structure, Function, and Genetics 28:405-420 (1997).
Stedman's Medical Dictionary, Illustrated, 24th Edition, Williams & Wilkins, Baltimore, Maryland, p. 707 (1982).
Stevens, "Streptococcal Toxic-Shock Syndrome: Spectrum of Disease, Pathogenesis, and New Concepts in Treatment", Emerging Infectious Diseases 1(3):69-78 (1995).
Stockbauer et al, "A natural variant of the cysteine protease virulence factor of group A *Streptococcus* with an arginine-glycine-aspartic acid (RGD) motif preferentially binds human integrins alphavbeta3 and alphaIIbbeta3", Proc. Natl. Acad. Sci. 96:242-247 (1999).
Stratford-Perricaudet et al, "Widespread Long-term Gene Transfer to Mouse Skeletal Muscles and Heart", J. Clin. Invest. 90:626-630 (1992).
Strauss, "Using DNA Fragments as Probes", Current Protocols in Molecular Biology, Supp. 24, 6.3.1-6.3.6 (1993).
Sun et al, "Chimeric antibody with human constant regions and mouse variable regions directed against carcinoma-associated antigen 17-1A", Proc. Natl. Acad. Sci. 84:214-218 (1987).
Supplementary Declaration by Dr. Julian Parkhill submitted in Opposition Proceedings against Novartis EP1645631 on May 10, 2010.
Supplementary Submission in Opposition Proceedings against Novartis EP 1 645 631 submitted May 25, 2010.
Sutcliff et al, "Lipoproteins of Gram-Positive Bacteria", Journal of Bacteriology 177(5):1123-1128 (1995).
Sworn Statement from Dr. Rino Rappuoli submitted in Opposition Proceedings against Novartis EP1645631 on Oct. 14, 2011.
Sworn Statement from Dr. Giovanna Campanella submitted in Opposition Proceedings against Novartis EP1409013 on Nov. 10, 2011.
Tappero et al, "Immunogenicity of 2 Serogroup B Outer-Membrane Protein Meningococcal Vaccines", JAMA 281 (16):1520-1527 (1999).

(56) References Cited

OTHER PUBLICATIONS

Tarkka et al, "Antibody production to a meningococcal outer membrane protein cloned into live *Salmonella typhimurium* aroA vaccine strain", Micrb. Pathogen 6:327-335 (1989).
Telford et al., "Chapter 1: Genomics and Proteomics in Vaccine Design", New Bacterial Vaccines, Kleweur Academic/Plenum Publishers, USA, pp. 1-11 (2003).
Tettelin et al, "Complete Genome Sequence of Neisseria meningitidis Serogroup B Strain MC58", Science 287:1809-1815 (2000).
Ton-That et al, "Purification and characterization of sortase, the transpeptidase that cleaves surface proteins of *Staphylococcus aureus* at the LPXTG motif", Proc Natl Acad Sci 96(22):12424-12429 (1999).
Ulmer et al, "Heterologous Protection Against Influenza by Injection of DNA Encoding a Viral Protein", Science 259:1745-1748 (1993).
Van Der Ley et al., "Construction of Neisseria meningitidis Strains Carrying Multiple Chromosomal Copies of the porA gene for Use in the production of a Multivalent Outer Membrane Vesicle Vaccine", Vaccine 13(4):401-407 (1995).
Wahl et al, "Improved Radioimaging and Tumor Localization with Monoclonal F(ab')2", J Nucl Med 24:316-325 (1983).
Webster's II New Riverside University Dictionary, The Riverside Publishing Company, p. 933 (1984).
Weldingh et al, "Two-Dimensional Electrophoresis for Analysis of *Mycobacterium tuberculosis* Culture Filtrate and Purification and Characterization of Six Novel Proteins", Infection and Immunity 66(8):3492-3500 (1998).
Welsch et al, "Protective Activity of Monoclonal Antibodies to Genome-Derived Neisserial Antigen 1870, a Neisseria meningitidis Candidate Vaccine", The Journal of Immunology 172:5606-5615 (2004).
Williams et al, "Introduction of foreign genes into tissues of living mice by DNA-coated microprojectiles", Proc. Natl. Acad. Sci. 88:2726-2730 (1991).
Wilson et al, "Hepatocyte-directed Gene Transfer in Vivo Leads to Transient Improvement of Hypercholesterolemia in Low Density Lipoprotein Receptor-deficient Rabbits", The Journal of Biological Chemistry 267(2):963-967 (1992).
Wolff et al, "Direct Gene Transfer into Mouse Muscle in Vivo", Science 247:1465-1468 (1990).
Woods et al., "Resistance to Meningococcemia Apparently Conferred by Anti-H.8 Monoclonal Antibody is Due to Contaminating Endotoxin and Not to Specific Immunoprotection", Infection and Immunity 55(8):1927-1928 (1987).
Wu et al, "Receptor-mediated in Vitro Gene Transformation by a Soluble DNA Carrier System", The Journal of Biological Chemistry 262(10):4429-4432 (1987).
Wu et al, "Receptor-mediated Gene Delivery and Expression in Vivo", The Journal of Biological Chemistry 263 (29):14621-14624 (1988).
Yakushi et al, "Lethality of the Covalent Linkage between Mislocalized Major Outer Membrane Lipoprotein and the Peptidoglycan of *Escherichia coli*", Journal of Bacteriology 179(9):2857-2862 (1997).
Yakushi et al, "A new ABC transporter mediating the detachment of lipid-modified proteins from membranes", Nature Cell Biology 2:212-218 (2000).
Yutsudo et al, "The Gene Encoding a New Mitogenic Factor in a *Streptococcus pyogenes* Strain is Distributed Only in Group A Streptococci", Infection and Immunity 62(9):4000-4004 (1994).
Zagursky et al, "Bioinformatics: Use in Bacterial Vaccine Delivery", BioTechniques 31(3):636-659 (2001).
Zavascki et al, "First Case Report of Neisseria lactamica Causing Cavitary Lung Disease in an Adult Organ Transplant Recipient", Journal of Clinical Microbiology 44(7):2666-2668 (2006).
Zollinger, "New and Improved Vaccines Against Meningococcal Disease", New Generation Vaccines, 2nd Ed., Myron M. Levine, et al. eds., Marcel Dekker, Inc., New York, NY pp. 469-488 (1997).

Zufferey et al, "Self-Inactivating Lentivirus Vector for Safe and Efficient in Vivo Gene Delivery", Journal of Virology 72(12):9873-9880 (1998).
Beernink et al, "The modular architecture of meningococcal factor H-binding protein", Microbiology 155:2873-2883 (2009).
Van Der Ende, A., et al., "Deletion of porA by Recombination between Clusters of Repetitive Extragenic Palindromic Sequences in Neisseria meningitidis", Infection and Immunity, 67(6):2928-2934 (1999).
Adacel Prescribing information, http://www.fda.gov/downloads/biologicsbloodvaccines/vaccines/approvedproducts/ucm142764.pdf, "Revised: [XX/201X]", accessed Feb. 14, 2015.
Burdroni, S. et al., "Neisseria Meningitidis is Structured in Clades Associated with Restriction Modification Systems that Modulate Homologous Recombination", PNAS, Mar. 15, 2011,108 (11): 4494-4499 and supporting information pp. 1-17.
Cheetham, et al., "An HPLC Method for the Determination of Acetyl and Pyruvyl Groups in Polysaccharides, Carbohydrade Polymers", School of Chemistry, The University of New South Wales, Dec., 1985, 5 (6): 399-406.
Farley, J., et al. poster entitled "Characterization, Cloning and Expression of Different Subfamlies of the ORF 2086 gene Neisseria Meningitidis", presented at the Thirteenth International Pathogenic Neisseria Conference (the 'IPNC Oslo 2002'), hosted at the Norwegian Institute of Public Health, Oslo, Norway between Sep. 1, 2002 and Sep. 6, 2002, as evidenced by photographs and transcript thereof.
Fredriksen, J.H., et al, "Production, Characterization and Control of MenB-vaccine "Folkehelsa": an Outer Membrane Vesicle Vaccine Against Group B Meningococcal Disease", NIPH Annals, 1991, 14 (2): 67-79.
Gil, J., et al., Proteomic Study via a Non-Gel Based Approach of Meningococcal Outer Membrane Vesicle Vaccine Obtained from Strain CU385 Human Vaccines, 2009, 5 (5): 347-356.
Havrix prescribing information, https://www.gsksource.com/pharma/content/dam/GlaxoSmithKline/US/en/Prescribing_Information/Havrix/pdf/HAVRIX.PDF, revised Jul. 2014, accessed Feb. 18, 2015.
Hedari, et al., Meningococcal Serogroups A, C, W-135, and Y Tetanus Toxoid Conjugate Vaccine: A New Conjugate Vaccine Against Invasive Meningococcal Disease., Infect Drug Resist. Apr. 3, 2014;7:85-99.
Menactra prescribing information, http://www.fda.gov/downloads/BiologicsBloodVaccines/Vaccines/ApprovedProducts/UCM131170.pdf, revised Aug. 26, 2014, accessed Feb. 14, 2015.
Menactra, Australian Public Assessment Report for Groups A, C, Y and W-135 Meningococcal Polysaccharide Diphtheria Toxoid Conjugate Vaccine, https://www.tga.gov.au/file/1277/download , Aug. 31, 2011, accessed Feb. 13, 2015 (part 1 and 2).
Mencevax, New Zealand data sheet, http://www.medsafe.gov.nz/profs/datasheet/m/Mencevaxacwyinj.pdf, date of preparation Mar. 25, 2014, accessed Feb. 14, 2015.
Menveo Package insert, http://www.fda.gov/downloads/BiologicsBloodVaccines/Vaccines/ApprovedProducts/UCM201349.pdf, accessed Feb. 19, 2015, revised Aug. 2013.
Nimenrix product monograph, gsk.com/media/673251/nimenrix.pdf, accessed Feb. 19, 2015, date of revision Jan. 9, 2015.
Nimenrix product monograph, http://webprod5.hc-sc.gc.ca/dpd-bdpp/item-iteme.do?pm-mp=00033642, accessed Mar. 2016. Date of revision Nov. 9, 2015.
Opposition documents (part 1 of part 11) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 2) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 3) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.

(56) References Cited

OTHER PUBLICATIONS

Opposition documents (part 4) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 5) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 6) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 7) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 8) submitted to the European Patent Office in EP2343308 dated Nov. 13, 2015 to Dec. 23, 2015, https://register.epo.org/application?number=EP10183020&Ing=en&tab=doclist, accessed Mar. 30, 2016.
Opposition documents (part 9) submitted to the European Patent Office in EP2343308 dated Nov. 13, 2015 to Dec. 23, 2015, https://register.epo.org/application?number=EP101830208,Ing=en&tab=doclist, accessed Mar. 30, 2016.
Opposition documents (part 10) submitted to the European Patent Office in EP2343308 dated Nov. 13, 2015 to Dec. 23, 2015, https://register.epo.org/application?number=EP101830208,Ing=en&tab=doclist, accessed Mar. 30, 2016.
Opposition documents (part 11) submitted to the European Patent Office in EP2343308 dated Nov. 13, 2015 to Dec. 23, 2015, https://register.epo.org/application?number=EP101830208,Ing=en&tab=doclist, accessed Mar. 30, 2016.
Registration document for VA-MENGOC-BC® Vaccine Together with Translation Into English and Translation Certificate, No publication date.
Resinger, et al., "Safety, Tolerability, and Immunogenicity of Gardasil Given Concomitantly with Menactra and Adacel" Pediatrics, Jun. 2010; 125 (6):1142-1151.
Rodriguez, A.P., et al., "The Epidemiological Impact of Antimeningococcal B Vaccination in Cuba", Mem Inst Oswaldo Cruz, 1999, Jul.-Aug. 94 (4): 433-440.
Rosenqvist, E., et al., "Effect of Aluminium Hydroxide and Meningococcal Serogroup C Capsular Polysaccharide on the Immunogenicity and Reactogenicity of a Group B Neisseria Meningitides Outer Membrane Vesicle Vaccine", Dev Biol Stand, 1998, 92: 323-333.
Rosenqvist et al, "Human Antibody Responses to Meningococcal Outer Membrane Antigens after Three Doses of the Norwegian Group B Meningococcal Vaccine", Infection and Immunity, 1995, 63(12): 4642-4652.
Sierra, G.V.G., et al.,"Vaccine Against Group B Neisseria Meningitidis: Protection Trial and Mass Vaccination Results in Cuba" NIPH Annals, 1991, 14 (2): 195-210.
Witze et al., Mapping Protein Post-Translational Modifications with Mass Spectrometry, Nat Methods, Oct. 2007; 4 (10): 798-806.
Database Uniprot [Online] Jul. 4, 2004, "SubName: Full=Factor H binding protein variant A05_001";Flags: Fragment, retrieved from EBI; UNIPROT database accession No. Q6VS29; Database entry from Oct. 28, 2014, entry version 29, sequence version 1See strains Neisseria meningitidis M98-250732 & M98250771.
Database Uniprot [Online] Jul. 5, 2004, "Factor H binding protein variant A22_001"; Flags: Fragment, retrieved from EBI; UNIPROT database accession No. Q6VS35; Database entry from Oct. 28, 2014, entry version 28, sequence version 2 updated on Sep. 23, 2008 See strains Neisseria meningitidis: CDC-1034 and L4-891.
Okuda et al, Lipoprotein sortingin bacteria, Annu. Rev. Microbiol., 65:239-259 (2011).

Fukasawa et al, "Neisseria meningitidis serogroup C polysaccharide and serogroup B outer membrane vesicle conjugate as a bivalent meningococcus vaccine candidate", Vaccine 17:2951-2958 (1999).
Rosenqvist et al, "Human Antibody Responses to Meningococcal Outer Membrane Antigens after Three Doses of the Norwegian Group B Meningococcal Vaccine", Infection and Immunity 63(12):4642-4652 (1995).
Van Der Ende et al, "Multiple Mechanisms of Phase Variation of PorA in Neisseria meningitidis", Infection and Immunity 68(12):6685-6690 (2000).
*GlaxoSmithKline UK Ltd v Wyeth Holdings LLC* [2016] EWHC 1045 (Ch) (May 12, 2016); Case No. HP-2015-000002; 36 pages; accessed http://www.bailii.org/ew/cases/EWHC/Ch/2016/1045.html on Jul. 11, 2016.
Koeberling, et al., "Bactericidal Antibody Responses Elicited by a Meningococcal Outer Membrane Vesicle Vaccine with Overexpressed Factor H-Binding Protein and Genetically Attenuated Endotoxin", The Journal of Infectious Diseases, Jul. 2008, 198:262-70.
Moe, et al., "Sequential Immunization with Vesicles Prepared from Heterologous Neisseria meningitidis Strains Elicits Broadly Protective Serum Antibodies to Group B Strains", Infection and Immunity, Nov. 2002, 70:11, 6021-6031.
Opposition papers EP2343308 May 2-9, 2016; 274 pages; accessed https://register.epo.org/application? number=EP10183020&Ing=en&tab=doclist on May 16, 2016.
Opposition papers EP2343308 Apr. 6-13, 2016; 30 pages; accessed https://register.epo.org/application? number=EP10183020&Ing=en&tab=doclist on May 16, 2016.
Opposition notice EP2343308_(Nov. 13, 2015); 21 pages; accessed https://register.epo.org/application? number=EP10183020&Ing=en&tab=doclist on Apr. 21, 2016.
Sierra, et al., "Vaccine Against Group B Neisseria Meningitidis: Protection Trial and Mass Vaccination Results in Cuba", NIPH Annals, Dec. 1991, 14:2, 195-210.
Uli, et al., "Outer Membrane Vesicles of VA-MENGOC-BC Vaccine Against Serogroup B of Neisseria Meningitidis: Analysis of Protein Components by Two-Dimensional Gel Electrophoresis and Mass Spectrometry", Proteomics, 2006, 6, 3389-3399.
Anderson et al; "Potential Impact of the Bivalent rLP2086 Vaccine on Neisseria meningitidis Invasive Disease and Carriage Isolates in Two Adolescent Populations"; poster presented at the 30th Annual Meeting of the European Society for Paediatric Infectious Diseases; May 8-12, 2012; Thessaloniki, Greece; http://epostersonline.s3.amazonaws.com/espid2012/espid2012.02400cf.NORMAL.pdf, May 12, 2012.
Anderson, "Elicitation of Functional Antibodies by a Group B Neisseria meningitidis Bivalent rLP2086 Vaccine in Non-Human Primates", NHP IPNC Poster Presentation 2008.
Ausubel et al, Current Protocols in Molecular Biology, Sections 2.10, 6.3 & 6.4 (1995).
Bambini et al, "Distribution and genetic variability of three vaccine components in a panel of strains representative of the diversity of serogroup B meningococcus", Vaccine 27:2794-2803 (2009).
Beernink et al, "Prevalence of Factor H-Binding Protein Variants and NadA among Meningococcal Group B Isolates from the United States: Implications for the Development of a Multicomponent Group B Vaccine", The Journal of Infectious Diseases 195:1472-1479 (2007).
Bergmann et al, "An endogenously synthesized decamer peptide efficiently primes cytotoxic T cells specific for the HIV-1 envelope glycoprotein", Eur. J. Immunol., 23(11):2777-2781 (1993).
Bergmann et al, "Flanking Residues Alter Antigenicity and Immunogenicity of Multi-Unit CTL Epitopes", The Journal of Immunology, 157:3242-3249 (1996).
Borrow et al, "Meningococcal surrogates of protection-serum bactericidal antibody activity", Vaccine 23:2222-2227 (2005).
Callahan, P.M., et al., "The Importance of Surface Charge in the Optimization of Antigen-Adjuvant Interactions", Pharmaceutical Research, 8(7):851-858 (1991).
Coleman et al, "Virus Attenuation by Genome-Scale Changes in Codon Pair Bias", Science, 320:1784-1787 (2008).

(56) References Cited

OTHER PUBLICATIONS

Database Geneseq Online, "N. meningitidis NL096 fHBP protein fragment SEQ ID 76", XP002703350, Database accession No. AXQ90374, Nov. 26, 2009.
Database Geneseq Online, "Neisseria meningitidis modified fHBP fusion protein SEQ:140", XP002703351, Database accession No. AZG10689, Apr. 28, 2011.
Database Geneseq Online, "Neisseria meningitidis modified fHBP NL096 SEQ:76", XP002703352,Database accession No. AZG10625, Apr. 28, 2011.
Database UniProt Online, "Subname: Full=Factor H binding protein variant A62_001; Subname: Full=Factor H binding protein variant A62_002; Flags: Fragment", XP002703353, Database accession No. COJF81, May 5, 2009.
Findlow et al, "Multicenter, Open-Label, Randomized Phase II Controlled Trial of an Investigational Recombinant Meningococcal Serogroup B Vaccine With and Without Outer Membrane Vesicles, Administered in Infance", Clinical Infectious Diseases 51(10):1127-1137 (2010).
Frankel et al, "Characterization of diphtheria fusion proteins targeted to the human interleukin-3 receptor", Protein Engineering 13(8):579-591 (2000).
Geysen et al, "A Priori Delineation of a Peptide Which Mimics a Discontinuous Antigenic Determinant", Molecular Immunology, 23(7):709-715 (1986).
Geysen et al, "Use of peptide synthesis to probe viral antigens for epitopes to a resolution of a single amino acid", Proc. Natl. Acad. Sci. USA, 81(13):3998-4002 (1984).
Harris et al, "Preclinical evidence for the potential of a bivalent fHBP vaccine to prevent Neisseria meningitidis serogroup C disease", Human Vaccines 7(Supplement):68-74 (2011).
Liu et al, "High-throughput imaging of bacterial colonies grown on filter plates with application to serum bactericidal assays", Journal of Immunological Methods 292(1-2):187-193 (2004).
Marshall, H.S., et al., "A phase 2 open-label safety and immunogenicity study of a meningococcal B bivalent rLP2086 vaccine in healthy adults", Vaccine, 31(12):1569-1575 (2013).
Mascioni et al, "Structural Basis for the Immunogenic Properties of the Meningococcal Vaccine Candidate LP2086", Journal of Biological Chemistry 284(13):8738-8746 (2009).
McNeil et al, "Detection of LP2086 on the cell surface of Neisseria meningitidis and its accessibility in the presence of serogroup B capsular polysaccharide", Vaccine 27:3417-3421 (2009).
Murphy, E., "HM807466: Neisseria meningitidis strain M08452 factor H binding protein variant B153 (fhbp) gene, partial cds.", URL:http://getentry.ddbj.nig.ac.jp/getentry/na/HM807466/?filetype=html, Jul. 21, 2010.
NCBI GenBank No. AAF42204.1, Tettelin, H. et al., "Hypothetical protein [Neisseria meningitidis]", Feb. 25, 2000, accessed Jul. 12, 2012.
NCBI GenBank : ACI46791, "Factor H binding protein variant A04_001, partial [Neisseria meningitidis]". Aug. 4, 2009.
NCBI GenBank: ACI46789.1; "Factor H binding protein variant A62_001, partial [Neisseria meningitidis]", Aug. 4, 2009.
NCBI GenBank: AY330365.1; "Neisseria meningitidis strain CDC1492 factor H binding protein variant A22_001 (fhbp) gene, partial cds"; Mar. 12, 2009; accessed Jun. 3, 2014.
NCBI GenBank: AY330400.1; "Neisseria meningitidis strain M982 factor H binding variant B09_001 (fhbp) gene, partial cds"; Mar. 12, 2009; accessed Jun. 3, 2014.
NCBI GenBank: AY330401.1; "Neisseria meningitidis strain 880049 factor H binding protein variant B03_001 (fhbp) gene, partial cds"; Mar. 12, 2009; accessed Jun. 3, 2014.
NCBI GenBank: FJ184103.1; "Neisseria meningitidis factor H binding protein variant A12_001 (fhbp) gene, partial cds"; Aug. 4, 2009; accessed Jun. 3, 2014.
NCBI GenBank: FJ184126.1; "Neisseria meningitidis factor H binding protein variant B02_001 (fhbp) gene, partial cds"; Aug. 4, 2009; accessed Jun. 3, 2014.
NCBI GenBank: FJ184157.1; "Neisseria meningitidis factor H binding protein variant B44_001 (fhbp) gene, partial cds"; Aug. 4, 2009; accessed Jun. 3, 2014.
Pajon et al, "Frequency of factor H-binding protein modular groups and susceptibility to cross-reactive bactericidal activity in invasive meningococcal isolates", Vaccine 28:2122-2129 (2010).
Paoletti et al, "Potency of clinical group B streptococcal conjugate vaccines", Vaccine, 19(15-16):2118-2126 (2001).
Patel, M., "Outbreaks of Serogroup B Meningococcal Disease on University Campuses—2013", Medical Officer, Meningitis and Vaccine Preventable Diseases Branch, http://www.cdc.gov/vaccines/acip/meetings/downloads/slides-2014-02/04-Mening-Patel.pdf, 16 Pages, Apr. 3, 2014.
PCT International Search Report for PCT/IB2011/053934 issued Jan. 20, 2012.
PCT International Search Report for PCT/US02/32369 issued Nov. 14, 2003.
Pillai et al, "Outer membrane protein (OMP) based vaccine for Neisseria meningitidis serogroup B", Vaccine 23:2206-2209 (2005).
Pizza et al, "Factor H-binding protein, a unique meningococcal vaccine antigen", Vaccine 26(Supp8):I46-I48 (2008).
Prome et al, "Characterization of new amino-terminal blocking groups in the normal human adult hemoglobin Hb A1b", Eur. Mass Spectrom. 1(2):195-201 (1995).
Prome et al, "Structure of the Human Adult Hemoglobin Minor Fraction A1b bu Electrospray and Secondary Ion Mass Spectrometry. Pyruvic Acid as Amino-Terminal Blocking Group", The Journal of Biological Chemistry 266 (20):13050-13054 (1991).
Psort analysis of 200 of the sequences disclosed in PCT/US99/09346, submitted in Opposition Proceedings against Novartis EP1645631 on May 25, 2010 Part 2.
Richmond, et al, On Behalf of the 2001 Study Investigators, "Safety, immunogenicity, and tolerability of meningococcal serogroup B bivalent recombinant lipoprotein 2086 vaccine in healthy adolescents: a ranomised, single-blind, placebo-controlled, phase 2 trial", www.thelancet.com/infection, 13 pages, Published online May 7, 2012.
Rose et al, "Pyruvic Acid is Attached Through Its Central Carbon Atom to the Amino Terminus of the Recombinant DNA-derived DNA-binding Protein Ner of Bacteriophage Mu", The Journal of Biological Chemistry 267 (27)19101-19106 (1992).
Sankaran, K., et al., "Lipid Modification of Bacterial Prolipoprotein", The Journal of Biological Chemistry, 269 (31):19701-19706 (1994).
Sastalla et al, "Codon-Optimized Fluorescent Proteins Designed for Expression in Low-GC Gram-Positive Bacteria", Applied and Environmental Microbiology, 75(7):2099-2110 (2009).
Seib et al, "Characterization of Diverse Subvariants of the Meningococcal Factor H (fH) Binding Protein for Their Ability to Bind fH, to Mediate Serum Resistance, and to Induce Bactericidal Antibodies", Infection and Immunity 79 (2):970-981 (2011).
Snape et al, "Immunogenicity of Two Investigational Serogroup B Meningococcal Vaccines in the First Year of Life", The Pediatric Infectious Disease Journal 29(11):e71-e79 (2010).
Suhrbier, "Multi-epitope DNA vaccines", Immunology and Cell Biology, 75(4):402-408 (1997).
University of Oklahoma—Neisseria gonorrhoeae webpage to retrieve genome [online] URL: http://dna1.chem.ou.edu/gono.html, Apr. 5, 2004, accessed Aug. 3, 2012.
Welsch et al, Factor H and Neisserial pathogenesis, Vaccine 26(Supp8):I40-I45 (2008).
Wolf et al, "Conditions Affecting Direct Gene Transfer into Rodent Muscle in Vivo", Biotechniques, 11(4):474-485 (1991).
Wyeth Neisseria Meningitidis Serogroup B Vaccine, Vaccine and Related Biological Products Advisory Committee Pre-Meeting Background Document, URL:http://www.fda.gov/downloads/AdvisoryCommittees/CommitteesMeetingMaterials/BloodVaccinesandOtherBiologics/VaccinesandRelatedBiologicalProductsAdvisoryCommittee/UCM249479.pdf, Mar. 4, 2011.

(56) References Cited

OTHER PUBLICATIONS

York, "Pfizer's Investigational Vaccine, rLP2086, for Invasive Meningococcal Serogroup B Disease", Sabin Vaccine Institute, http://www.sabin.org/sites/sabin.org/files/Laura%20J%20York.pdf, accessed Aug. 1, 2014.
Zhu et al, "Evaluation of Recombinant Lipidated P2086 Protein as a Vaccine Candidate for Group B Neisseria meningitidis in a Murine Nasal Challenge Model", Infection and Immunity 73(10):6838-6845 (2005).
Database UniPro 'Online', "Hypothetical Protein NMB1870", XP002308111, Oct. 1, 2000.
Database UniProt 'Online', "Putative lipoprotein N meningitidis (Serotype A)", XP002320503, Oct. 1, 2000.
Datasheet for MENCEVAX™, International Data Sheet version 2.1 (May 15, 2000).
Datasheet for MENOMUNE™, product information as of Feb. 2001.
Datasheet for MeNZB® vaccine product prepared Jun. 23, 2009.
De et al, "Purification and characterization of Streptococcus pneumoniae palmitoylated pneumococcal surface adhesin A expressed in Escherichia coli", Vaccine 18:1811-1821 (2000).
Declaration by Dr. Julian Parkhill, submitted in Opposition Proceedings against Novartis EP1645631 on Jul. 23, 2008.
Declaration of Dr. Ellen Murphy, submitted in Opposition Proceedings against Novartis EP 1 645 631 on Sep. 14, 2011.
Declaration by Professor Paul Dunman, submitted in Opposition Proceedings against Novartis EP1645631 on Sep. 14, 2011.
Declaration of Emilio A. Emini, Ph.D., submitted in Opposition Proceedings against Novartis EP 1645631 on Nov. 3, 2011.
Declaration of Lakshmi Khandke, Ph.D., submitted in Opposition Proceedings against Novartis EP 1409013 on Dec. 21, 2011.
Definition of "epitope" from Henderson's Dictionary of Biological Terms, 11th edition, Eleanor Lawrence ed., pp. 37, 184 and cover pages (1997).
Delgado et al., "Lipoprotein NMB0928 from Neisseria meningitidis Serogroup B as a Novel Vaccine Candidate", Vaccine 25:8420-8431 (2007).
Dempsey et al., "The physical map of the chromosome of a serogroup A strain of Neisseria meningitidis shows complex rearrangements relative to the chromosomes of the two mapped strains of the closely related species N. gonorrhoeae," Journal of Bacteriology 177(22):6390-6400 (1995).
Devereux et al., "A comprehensive set of sequence analysis programs for the VAX", Nucleic Acids Research 12 (1):387-395 (1984).
Duby et al, "Using Synthetic Oligonucleotides as Probes", Current Protocols in Molecular Biology, Supp. 2, 6.4.1-6.4.10 (1993).
Eddy, "Hidden Markov models", Current Opinion in Structural Biology 6:361-365 (1996).
Ellen et al, "M Protein-Associated Adherence of Streptococcus pyogenes to Epithelial Surfaces: Prerequisite for Virulence", Infection and Immunity 5(5):826-830 (1972).
Ellis, "New Technologies for Making Vaccines", Vaccines, Plotkin et al. editors, W.B. Saunders Company, Philadelphia, Chapter 29, pp. 568-575 (1988).
Eng et al, "An Approach to Correlate Tandem Mass Spectral Data of Peptides with Amino Acid Sequences in a Protein Database", J Am Soc Mass Spectrom 5:976-989 (1994).
EP Application No. 07075161.5 Response to Communication submitted Oct. 28, 2009.
Erdile et al, "Role of Attached Lipid in Immunogenicity of Borrelia burgdorferi OspA", Infection and Immunity 61(1):81-90 (1993).
Farley et al., "Characterization, cloning and expression of different subfamilies of the ORF2086 gene from Neisseria meningitidis", Abstracts of the Thirteenth International Pathogenic Neisseria Conference, (Ed) Caugant et al., Oslo, Norway, p. 124, Sep. 1-6, 2002.
Feavers et al, "Meningococcal protein antigens and vaccines", Vaccine 275:B42-B50 (2009).

Felgner et al, "Lipofection: A highly efficient, lipid-mediated DNA-transfection procedure", Proc. Natl. Acad. Sci. 84:7413-7417 (1987).
Felgner et al, "Cationic liposome-mediated transfection", Nature 337:387-388 (1989).
Final Written Submission in Preparation of Oral Proceedings in Opposition against Novartis EP 1 645 631 submitted Sep. 14, 2011.
Fischetti et al, "Conservation of a hexapeptide sequence in the anchor region of surface proteins from Gram-positive cocci", Molecular Microbiology 4(9):1603-1605 (1990).
Fleischmann et al, "Whole-Genome Random Sequencing and Assembly of Haemophilus influenzae Rd", Science 269:496-501 (1995).
Fletcher et al, "Vaccine Potential of the Neisseria meningitidis 2086 Lipoprotein", Infection and Immunity 72(4):2088-2100 (2004).
Fogg et al, "Constitutive Expression of Fibronectin Binding in Streptococcus pyogenes as a Result of Anaerobic Activation of rofA", Journal of Bacteriology 179(19):6172-6180 (1997).
Fontana et al, "A genomic approach to identify vaccine candidates against gonococcus", Abstract from the 13th International Pathogenic Neisseria Conference, Oslo Norway, Sep. 1-6, 2002, p. 248 (http://neisseria.org/ipnc/history.shtml).
Foster et al, "Surface protein adhesins of Staphylococcus aureus", Trends in Microbiology 6(12):484-488 (1998).
Fraser et al, "Genomic sequence of a Lyme disease spirochaete, Borrelia burgdorferi", Nature 390:580-591 (1997).
GenBank No. EF108319.1, O'Leary, M. M. et al., Neisseria meningitidis strain NM452 FHBP/GNA1870 variant (GNA1870) gene, complete cds, Nov. 8, 2006, accessed Sep. 2012.
Gentz et al, "Bioassay for trans-activation using purified human immunodeficiency virus tat-encoded protein: Trans-activation requires mRNA synthesis", Proc. Natl. Acad. Sci. 86:821-824 (1989).
Giuliani et al, "The Region Comprising Amino Acids 100 to 255 of Neisseria meningitidis Lipoprotein GNA 1870 Elicits Bactericidal Antibodies", Infection and Immunity 73(2):1151-1160 (2005).
Giuliani et al, "A universal vaccine for serogroup B meningococcus" Proc Natl Acad Sci 103(29):10834-10839 (2006).
Gold et al., "Chapter 78. Translational Initiation", Escherichia coli and Salmonella typhimurium: Cellular and Molecular Biology, Ed. Neidhardt FC, vol. 2, pp. 1302-1307 (1987).
Goldschneider et al, "Human Immunity to the Meningococcus I. The Role of Humoral Antibodies", Journal of Experimental Medicine 129(6):1307-1326 (1969).
Goldschneider et al, "Human Immunity to the Meningococcus II. Development of Natural Immunity", Journal of Experimental Medicine 129(6):1327-1348 (1969).
Gomez et al, "The Bacillus subtilis lipoprotein LpIA causes cell lysis when expressed in Escherichia coli", Microbiology 140:1839-1845 (1994).
Gotschlich et al, "Human Immunity to the Meningococcus. IV. Immunogenicity of Group A and Group C Meningococcal Polysaccharides in Human Volunteers", Journal of Experimental Medicine 129(6):1367-1384 (1969).
Gotschlich et al, "Human Immunity to the Meningococcus. v. The Effect of Immunization with Meningococcal Group C Polysaccharide on the Carrier State", Journal of Experimental Medicine 129(6):1385-1395 (1969).
Graham et al, "Characteristics of a Human Cell Line Transformed by DNA from Human Adenovirus Type 5", J. Gen. Virology 36:59-72 (1977).
Graham, "Covalently closed circles of human adenovirus DNA are infectious", The EMBO Journal 3(12):2917-2922 (1984).
Grandi, "Reverse Vaccinology: A Critical Analysis", Encyclopedia of Genetics, Genomics, Proteomics and Bioinformatics, pp. 1320-1330 (2005).
Green et al, "The e (p4) Outer Membrane Protein of Haemophilus influenzae: Biologic Activity of Anti-e Serum and Cloning and Sequencing of the Structural Gene", Infection and Immunity 59(9):3191-3198 (1991).
Greenspan et al, "Defining epitopes: It's not as easy as it seems", Nature Biotechnology 17:936-937 (1999).

(56) References Cited

OTHER PUBLICATIONS

Griffin et al, "Computer Analysis of Sequence Data", Methods in Molecular Biology, vol. 24, Part 1, Chapter 1, Humana Press, New Jersey (1994).

* cited by examiner

FIG. 1

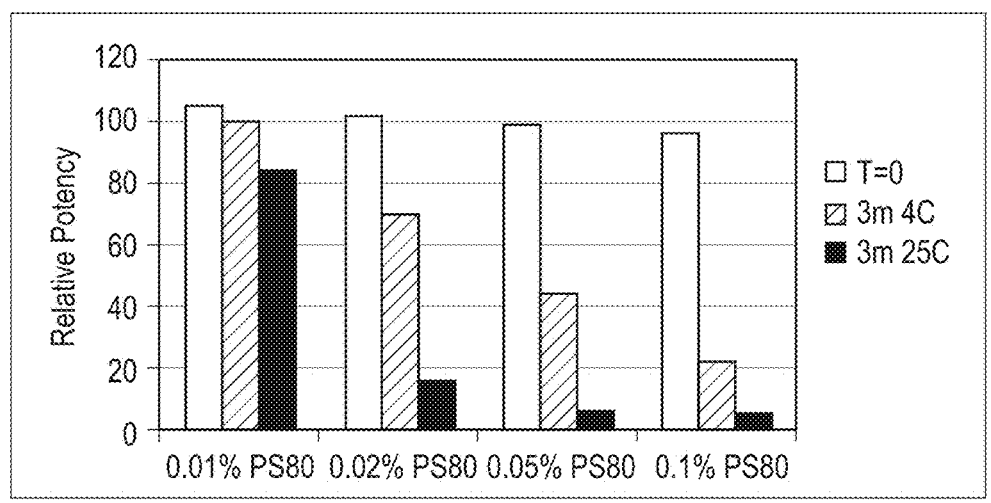

Stability of Subfamily B in Formulations with Various Polysorbate 80 Concentrations 200 µg/mL each of subfamily A and B were formulated in 10 mM Histidine buffer at pH 6.3 with 0.5 mg/mL Aluminum and variable Polysorbate 80 concentrations. Formulations were filled in BD syringes and subjected to storage at 2-8°C or 25°C. Potency values for subfamily B at initial and 3 months time point are shown.

FIG. 2

Accelerated Stability of Subfamily B with Various Polysorbate 80 Concentrations

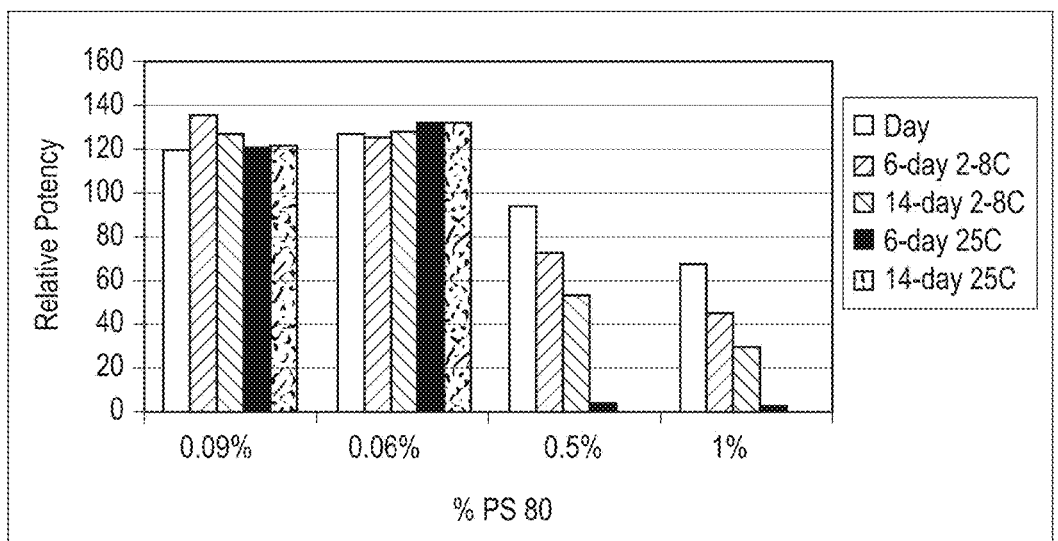

Drug Substance subfamily B formulated in 0.09% Polysorbate 80, 10 mM Histidine, pH 6.5 was spiked with variable Polysorbate 80 concentrations to monitor the effect of Polysorbate 80 on stability. Samples were subjected to storage at 2-8°C or 25°C, and potency was measured at initial, 6-day and 14-day time points.

FIG. 3

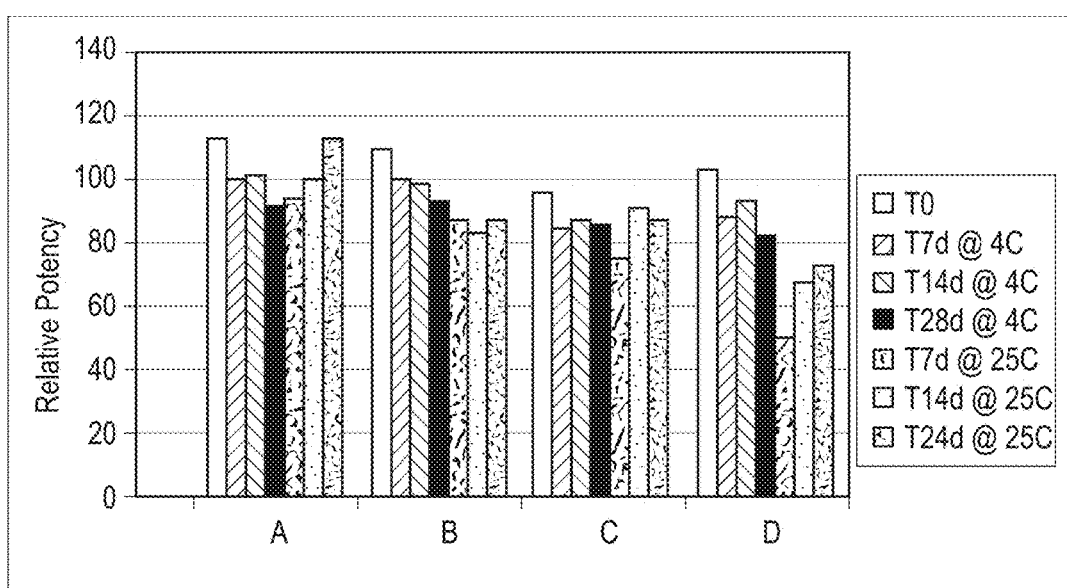

Potency of Subfamily B at 200 µg/mL for 28 days

MnB rLP2086 subfamily A + B formulated at 200 µg/mL dosage each with 0.5 mg/mL aluminum as aluminum phosphate in the presence of varying concentrations of Polysorbate 80 (A=0%, B=0.002% and C=0.0005% and D=0.01%) and stored at either 2-8°C or 25°C. The Polysorbate 80: protein molar ratios of A, B, C and D are 0, 1.1, 2.7 and 5.3, respectively. The potency of subfamily B protein was then tested at 0, 7, 14 and 28 days. At each time point, the samples were agitated as described for 24 hours prior to the testing.

FIG. 4

Potency of Subfamily B at 20 µg/mL for 28 days

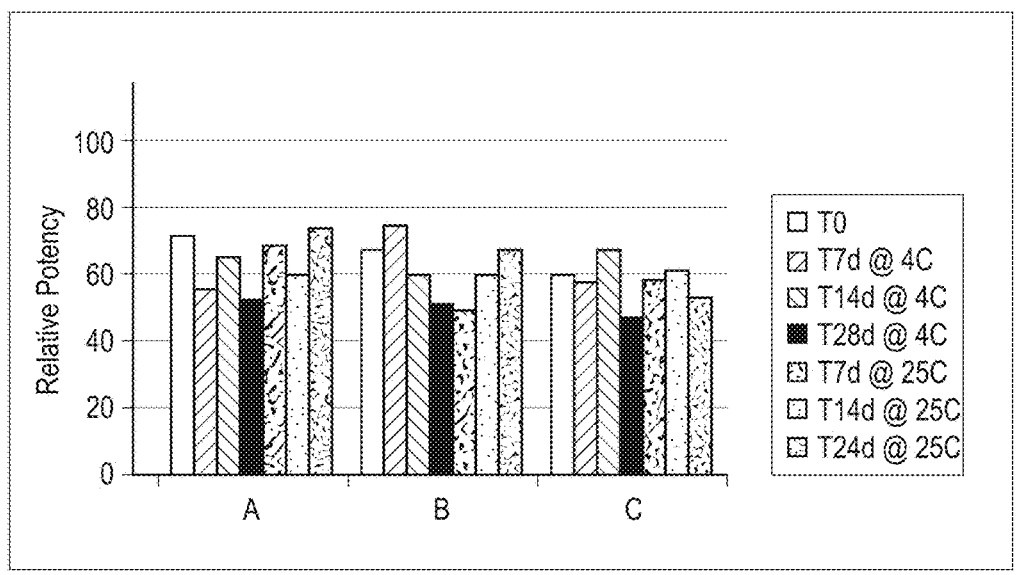

MnB rLP2086 subfamily A + B formulated at 20 µg/mL dosage each with 0.5 mg/mL aluminum as aluminum phosphate in the presence of varying concentrations of Polysorbate 80 (A=0%, B=0.0005% and C=0.001%) and stored at either 2-8°C or 25°C. The Polysorbate 80: protein molar ratios of A, B and C are 0, 2.7 and 5.3, respectively. The potency of subfamily B protein was then tested at 0, 7, 14 and 28 days. At each time point, the samples were agitated as described for 24 hours prior to the testing.

MnB rLP2086 subfamily A + B formulated at 200 µg/mL with Polysorbate80; Protein molar ratios 1.4, 2.3, 3.4, 3.9, 4.3, 4.7, 10.7 for lots 50A, 50B, 50C, 50D, 50E, 50F, 50G, respectively. T-0, T-10, and T-20 represent time zero, 10, and 20 days, respectively. Top graph is potency results for subfamily A and bottom graph is potency results for subfamily B protein. At each time point, the samples were agitated as described for 24 hours prior to the testing.

MnB rLP2086 subfamily A + B formulated at 20 µg/mL with Polysorbate80; protein molar ratios 1.4, 2.3, 3.4, 3.9, 4.3, 4.7, 10.7 for lots 53A, 53B, 53C, 53D, 53E, 53F, 53G, respectively. T-0, T-10, and T-20 represents time zero, 10, and 20 days, respectively. Top graph is potency results for subfamily A and bottom graph is potency results for subfamily B protein. At each time point, the samples were agitated as described for 24 hours prior to the testing.

Protein Binding to Aluminum Phosphate at pH 6.5

MnB rLP2086 subfamily A + B was formulated at 400µg/mL in 10mM Histidine buffer with 150 mM NaCl and POLYSORBATE 80 concentration at 0.02% at pH 6.5. The X-axis represents aluminum content in the formulation and Y-axis is the percent protein bound measured by IEX HPLC assay.

Binding to MnB rLP2086 Subfamily A and B as a Function of pH

MnB subfamily A + B formulations of subfamily A and B proteins at 200 μg/mL each were formulated with 0.5 mg/mL aluminum as aluminum phosphate in 10mM Histidine buffer with 150 mM NaCl varying pH. The multiple lots represent formulations prepared with different lots of DS as indicated in the figure.

FIG. 9

The Effect of pH, Buffer and Protein Concentration on Binding of rLP2086 Subfamily A and B

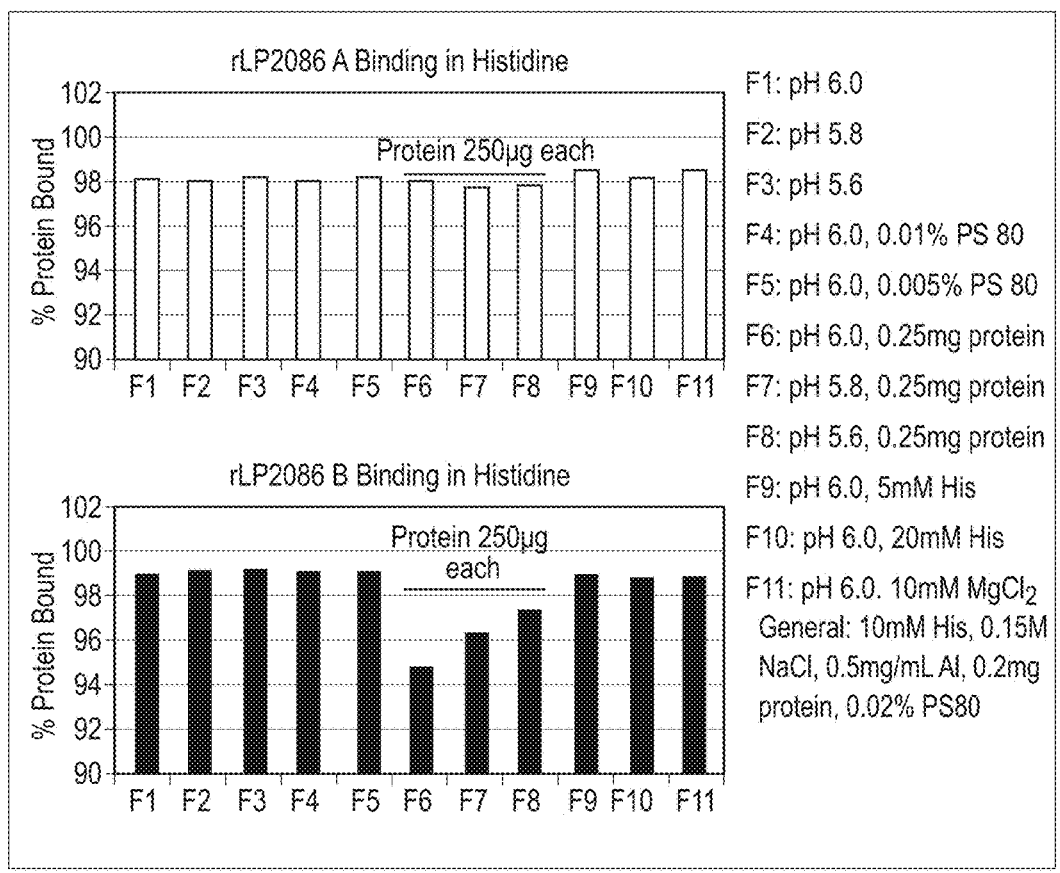

F1: pH 6.0
F2: pH 5.8
F3: pH 5.6
F4: pH 6.0, 0.01% PS 80
F5: pH 6.0, 0.005% PS 80
F6: pH 6.0, 0.25mg protein
F7: pH 5.8, 0.25mg protein
F8: pH 5.6, 0.25mg protein
F9: pH 6.0, 5mM His
F10: pH 6.0, 20mM His
F11: pH 6.0, 10mM $MgCl_2$
General: 10mM His, 0.15M NaCl, 0.5mg/mL Al, 0.2mg protein, 0.02% PS80

Eleven formulations of MnB subfamily A + B formulations with subfamily A + B proteins were formulated at 200µg/mL with 0.5 mg/mL aluminum as aluminum phosphate in 10mM Histidine buffer with 150 mM NaCl and 0.02% PS 80 varying pH (F1 through F3 with 200 µg/mL protein each and 0.02% Polysorbate 80); varying Polysorbate concentrations of Polysorbate 80 from 0.01% to 0.005% (F4-F5); varying protein concentration to 250µg/mL for each subfamily protein (F6-F8), varying Histidine buffer concentration 5mM and 20mM (F9 and F10); additional 10mM MgCl2 (F11).

FIG. 10

Visual Appearance of rLP2086 Formuations without Aluminum Phosphate

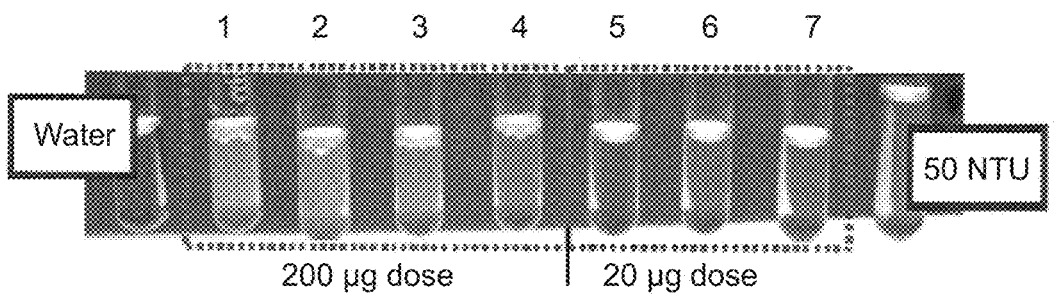

Photograph of two formulations of rLP2086 A + B proteins at 200 (left) and 20 (right) µg/mL without Aluminum Phosphate with various concentrations of Polysorbate-80, expressed as a percentage, indicated across the top (1 = 0%, 2 = 0.002%, 3 = 0.005%, 4 = 0.01%, 5 = 0%, 6 = 0.0005%, 7 = 0.001%). All tubes were incubated at 5°C for 14 days and agitated for 24 hours prior to the testing. Water and the 50 NTU (nephelometric turbidity units) turbidity standard were included for visual comparison on each end; water showing clarity and 50 NTU showing the appearance of a turbid solution. Note: similar results were also obtained after incubation for 1, 7 and 28 days.

Optical Density measurements of samples from formulations without aluminum phosphate, at λ=320 nm for rLP2086 200 µg/mL formulation, designation 15C (0.005% Polysorbate 80), over one month at 5°C. Agitated samples, red squares, and no-agitation samples are indicated in blue diamonds.

FIG. 12

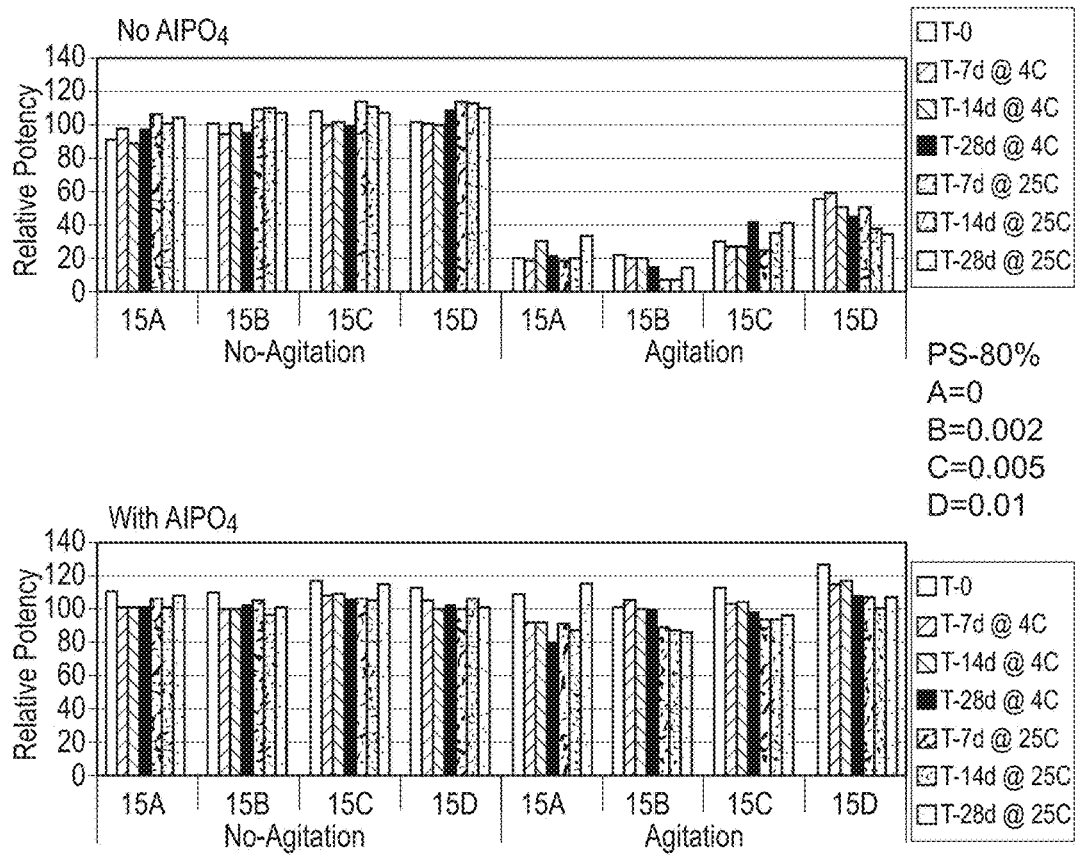

MnB rLP2086 subfamily A + B formulated at 200 μg/mL of each subfamily. Formulations were made in histidine buffered saline with and without AlPO4 and with varying levels of Polysorbate 80. Top graph represents formulation without AlPO4 and bottom graph represents formulations with 0.5 mg/mL aluminum as aluminum phosphate. Four groups on the left half of the graph represent no-agitation and the other four groups on the right represent the agitation as labeled on the X-axis at the bottom of each graph. The Y-axis represents the percent relative potency. The Polysorbate 80 concentrations in the final formulations are 0%, 0.0005%, 0.001%, and 0.01% for lot 15A or 13A, 15B or 13B, 15C or 13C, and 15D or 13D, respectively. The samples were stored at 2-8°C and 25°C. T0, T7d, T14d and T28d represent time zero, 7, 14 and 28 days. Each bar represents each time point data.

FIG. 13

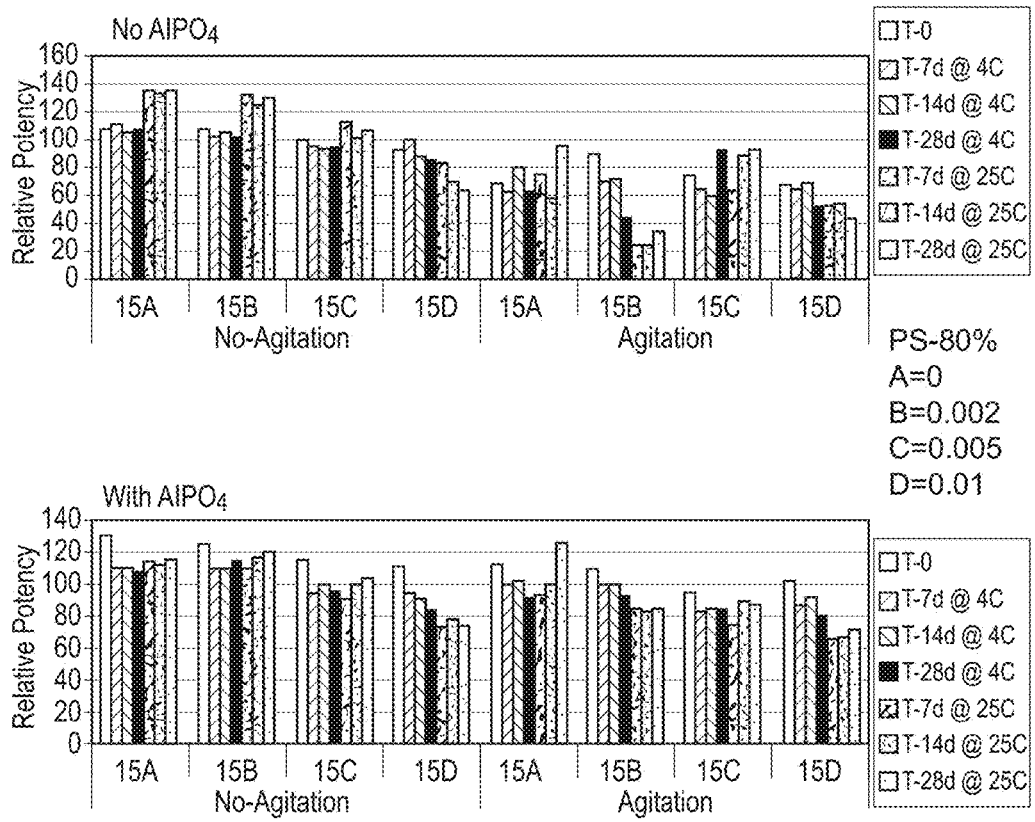

MnB rLP2086 subfamily A + B formulated at 200 µg/mL of each subfamily. Formulations were made in histidine buffered saline with and without AlPO4 and with varying levels of Polysorbate 80. Top graph represents formulation without AlPO4 and bottom graph represents formulations with 0.5 mg/mL aluminum as aluminum phosphate. Four groups on the left half of the graph represent no-agitation and the other four groups on the right represent the agitation as labeled on the X-axis at the bottom of each graph. The Y-axis represents the percent relative potency. The Polysorbate 80 concentrations in the final formulations are 0%, 0.0005%, 0.001%, and 0.01% for lot 15A or 13A, 15B or 13B, 15C or 13C, and 15D or 13D, respectively. The samples were stored at 2-8°C and 25°C. T0, T7d, T14d and T28d represent time zero, 7, 14 and 28 days. Each bar represents each time point data.

Correlation of Potency and Bound Molar Ratio for Subfamily B

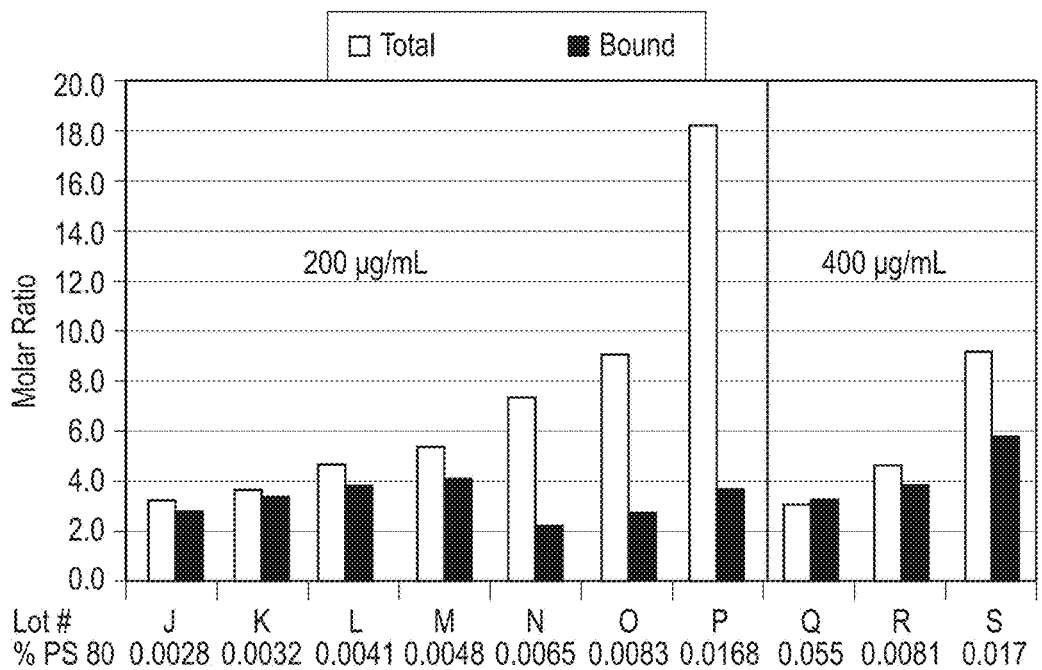
FIG. 19  Molar Ratio Results for Subfamily B
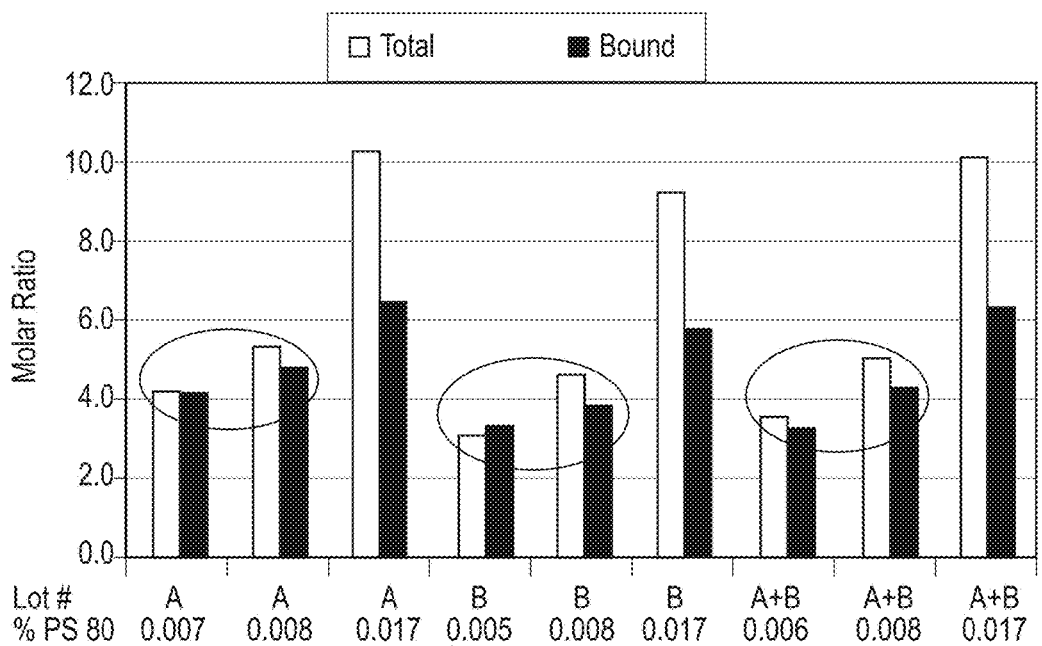
FIG. 20  Molar Ratio Results for rLP2086 Formulations @ 400μg/mL

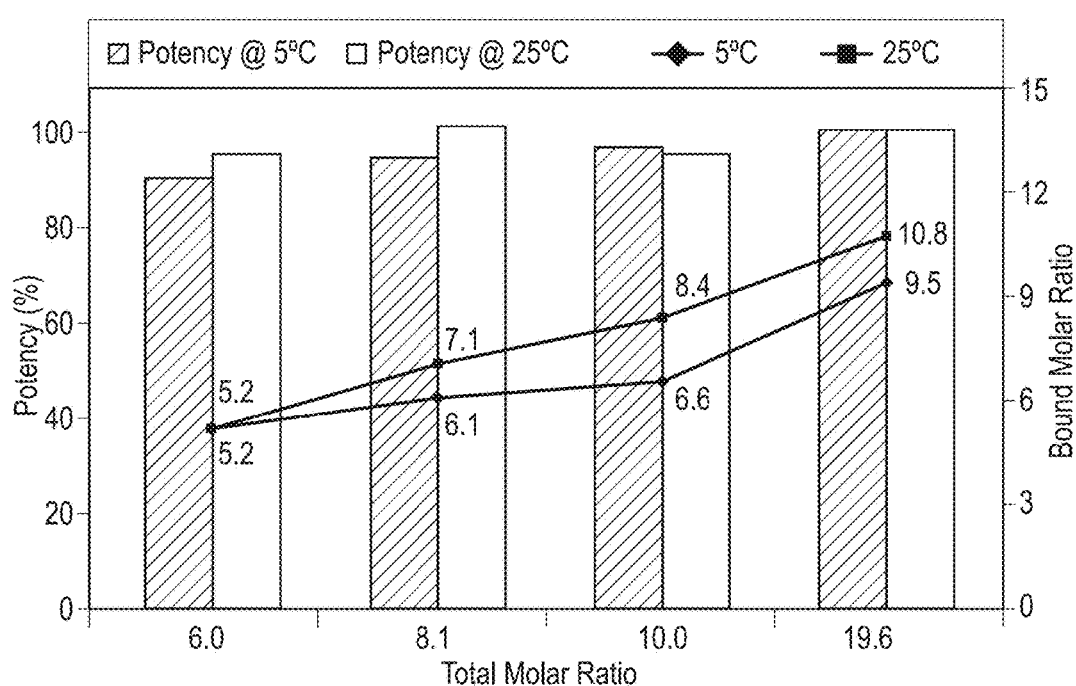
FIG. 23 Potency and Bound Molar Ratio Results for Subfamily A
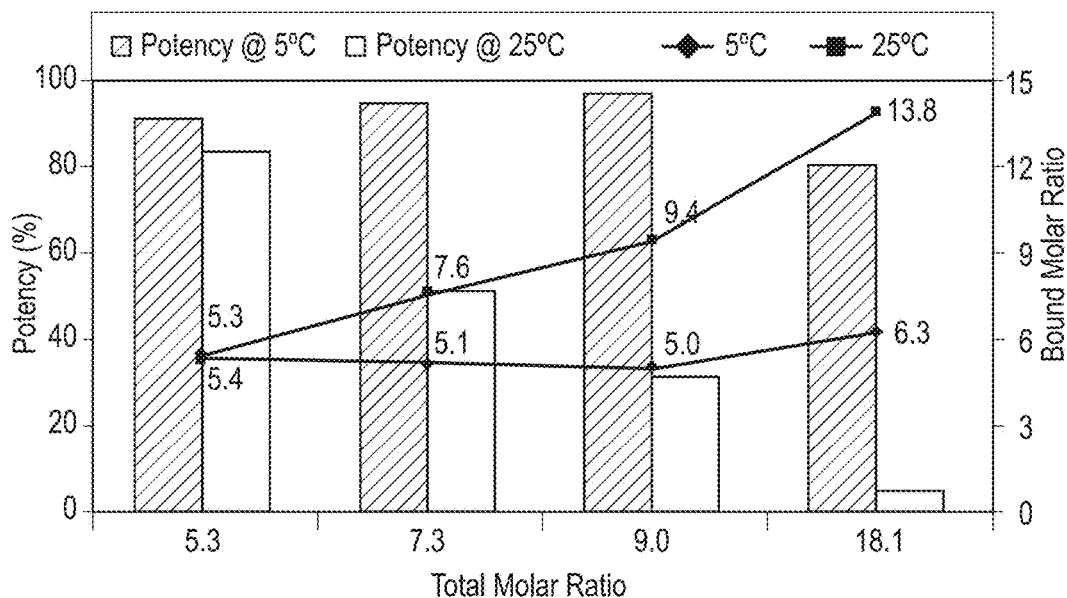
FIG. 24 Potency and Bound Molar Ratio Results for Subfamily B

FIG. 25

Binding of Subfamily A with AlPO$_4$ in Succinate and Histidine Buffers

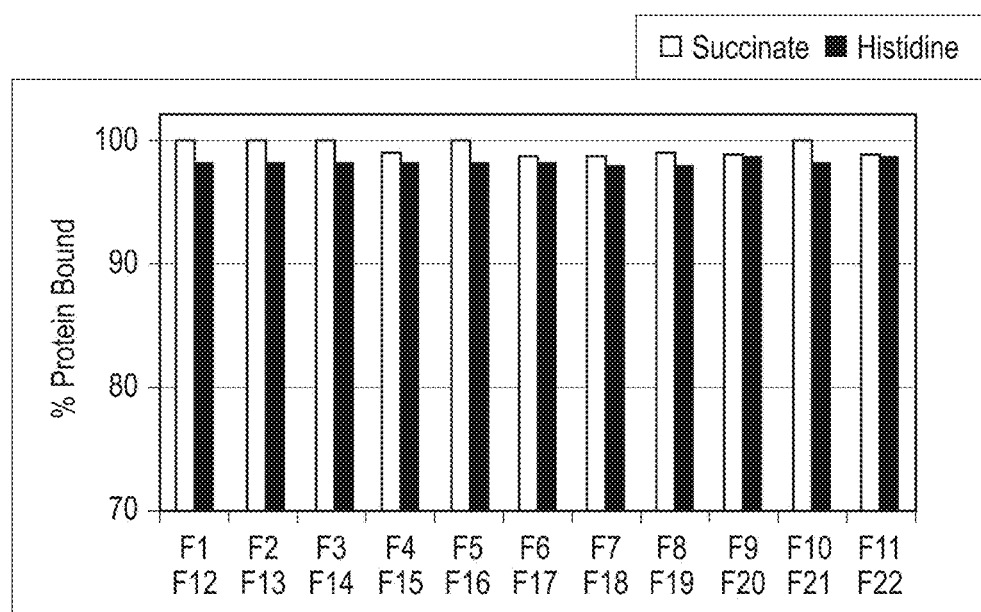

Binding of Subfamily A protein from formulations of bivalent MnB formulations formulated at 200µg/mL of each protein with 0.5 mg/mL aluminum as aluminum phosphate in 10mM Histidine buffer with 150 mM NaCl and 0.02% PS 80 varying pH (F1 through F3 with 200µg/mL protein each and 0.02% PS 80); varying polysorbate concentrations of PS-80 from 0.01, 0.05 (F4-F5); varying protein concentration to 250µg/mL (F6-F8), varying Histidine buffer concentration 5mM and 20mM (F9 and F10); additional 10mM MgCl$_2$ (F11).

FIG. 26

Binding of Subfamily B with AlPO$_4$ in Succinate and Histidine Buffers

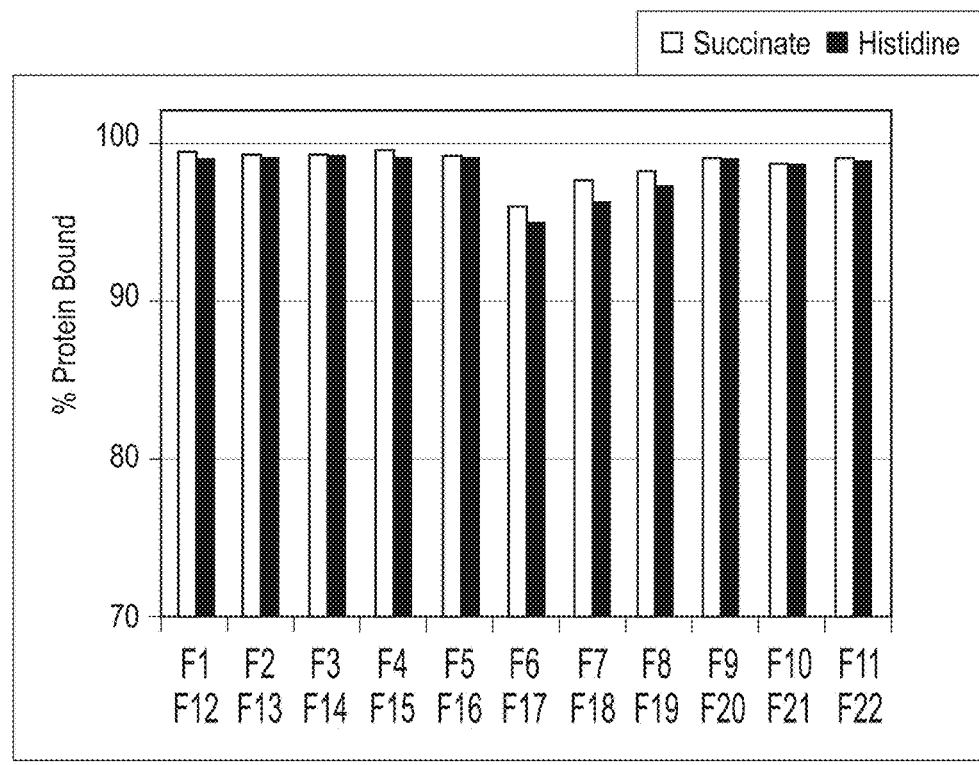

Binding of Subfamily B protein from formulations of bivalent MnB formulations formulated at 200µg/mL of each protein with 0.5 mg/mL aluminum as aluminum phosphate in 10mM Histidine buffer with 150 mM NaCl and 0.02% PS 80 varying pH (F1 through F3 with 200µg/mL protein each and 0.02% PS 80); varying polysorbate concentrations of PS-80 from 0.01, 0.05 (F4-F5); varying protein concentration to 250µg/mL (F6-F8), varying Histidine buffer concentration 5mM and 20mM (F9 and F10); additional 10mM MgCl$_2$ (F11).

Comparison of Binding in Succinate Histidine, and Phosphate Buffer

FIG. 28  pH Dependent Binding of Subfamily A with AlPO$_4$
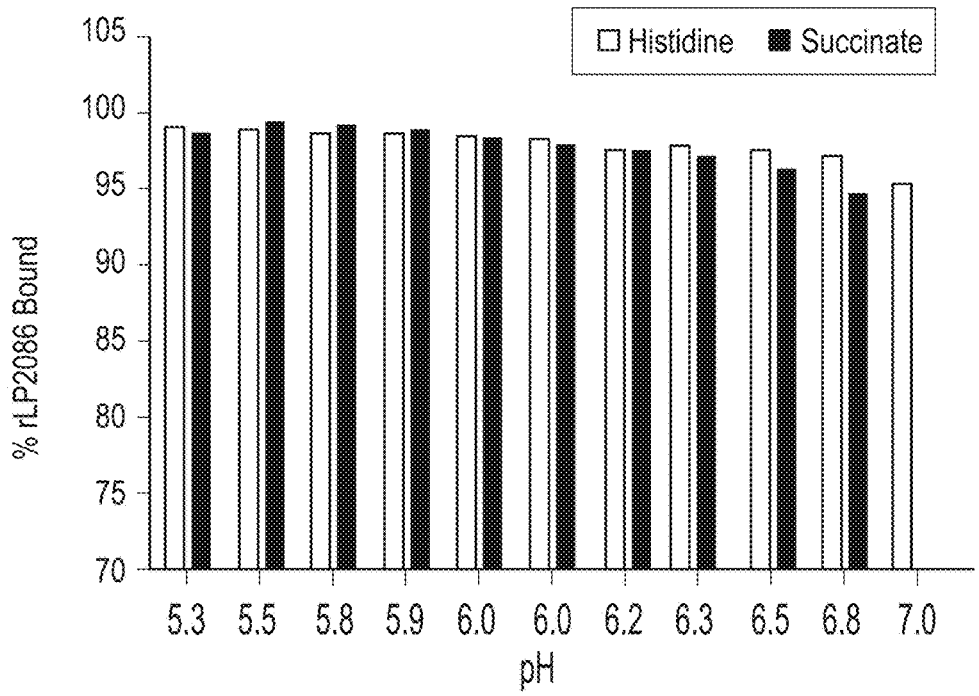
FIG. 29  pH Dependent Binding of Subfamily B with AlPO$_4$
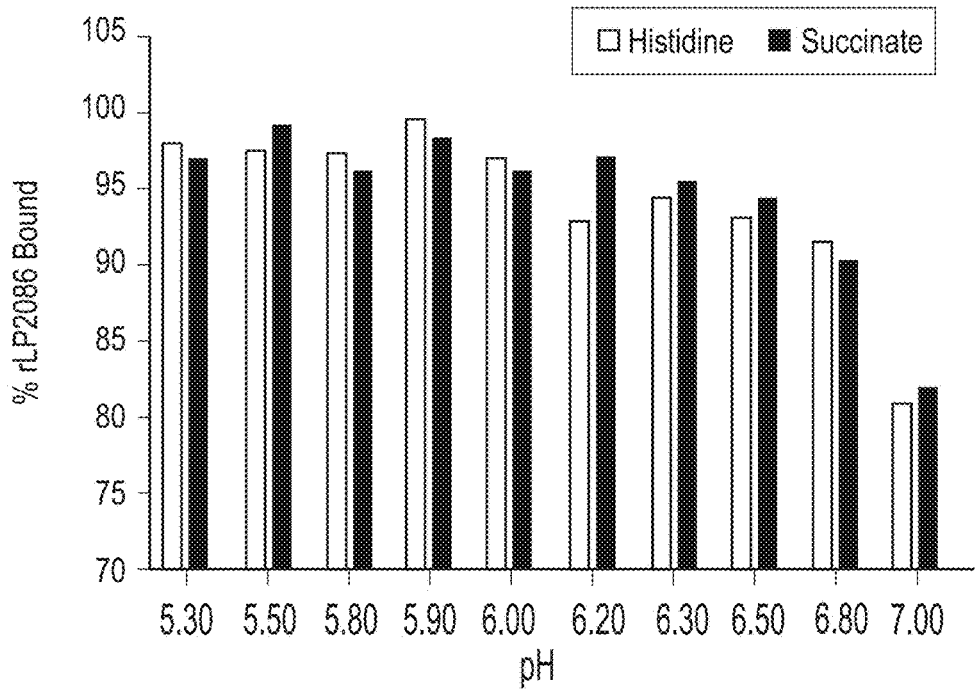

US 9,556,240 B2

STABLE FORMULATIONS OF *NEISSERIA MENINGITIDIS* RLP2086 ANTIGENS

FIELD OF THE INVENTION

The present invention relates to formulations of *Neisseria meningitidis* rLP2086 Subfamily B antigens in immunogenic compositions as described herein. The present invention also relates to methods of preserving the conformation of *Neisseria meningitidis* rLP2086 antigens and methods for determining the potency of *Neisseria meningitidis* rLP2086 antigens.

BACKGROUND OF THE INVENTION rLP2086 is a recombinant 28-kDa lipoprotein that induces cross-reactive bacterial antibodies against a number of *Neisseria meningitidis* strains. Based on deduced amino acid sequence homology, two different subfamilies of rLP2086 were identified, A and B. These two subfamilies were used in the formulation of the MnB-rLP2086 vaccine samples containing 20, 60, 120, and 200 μg/mL each in 10 mM Histidine (pH 6.0), 150 mM NaCl, and 0.5 mg/mL aluminum with varying levels of Polysorbate 80 (PS-80). Polysorbate 80, also known, as TWEEN 80, is a nonionic surfactant and emulsifier derived from sorbitol, and is frequently used in pharmaceutical formulations as an emulsifier, solubilizer and stabilizer. The presence of Polysorbate 80 in the MnB rLP2086 immunogenic composition is believed to prevent aggregation during formulation, processing, filtration, filling and shipping, reduce filter membrane absorption, and reduce tubing absorption.

SUMMARY OF THE INVENTION

In some embodiments, the present invention provides a stable immunogenic composition, wherein the potency of a LP2086 Subfamily B polypeptide is maintained for at least about 1-12 months, about 6-18 months, about 12-24 months, about 24-36 months, or about 36-48 months. In some embodiments, the immunogenic composition further comprises a LP2086 Subfamily A polypeptide.

In some embodiments, the immunogenic composition further comprises a detergent. In some embodiments, the molar ratio of the detergent to protein is between about 0.5:1 and about 10:1; between about 1:1 and about 5:1; or between about 1.4:1 and 4.2:1. In some embodiments, the molar ratio of the detergent to protein is about 2.8:1. In some embodiments the amount of detergent is sufficient to reduce polypeptide binding to silicon in a container, such as a syringe or a vial. In some embodiments, the detergent is a non-ionic detergent, such as a polysorbate detergent. In some embodiments, the detergent is Polysorbate-80.

In some embodiments, the immunogenic composition further comprises a multivalent cation. In some embodiments, the multivalent cation is calcium or aluminum. In some embodiments, the immunogenic composition comprises calcium phosphate. In some embodiments, the immunogenic composition comprises aluminum as aluminum phosphate, aluminum hydroxide, aluminum sulfate, or alum. In some embodiments, the concentration of aluminum is between about 0.1 mg/mL and 1.0 mg/mL. In some embodiments, the concentration of aluminum is about 0.5 mg/mL.

In some embodiments, the immunogenic composition further comprises histidine. In some embodiments, the concentration of histidine is between about 2 mM and about 20 mM or between about 5 mM and about 15 mM. In some embodiments, the concentration of histidine is about 10 mM. In some embodiments, the pH of the histidine is between about 5.0 and about 8.0 or between about 5.8 and about 6.0. In some embodiments, the concentration of histidine is 10 mM, pH 6.0.

In some embodiments, the immunogenic composition further comprises succinate. In some embodiments, the concentration of succinate is between about 2 mM and about 10 mM or between about 3 mM and about 7 mM. In some embodiments, the concentration of succinate is about 5 mM. In some embodiments, the pH of the succinate is between about 5.0 and about 8.0 or between about 5.8 and about 6.0. In some embodiments, the concentration of succinate is 5 mM, pH 6.0.

In some embodiments, the immunogenic composition is lyophilized. In some embodiments, the lyophilized composition is resuspended in a buffer comprising aluminum. In some embodiments, the aluminum is present as aluminum phosphate, aluminum hydroxide, aluminum sulfate, or alum.

In some embodiments, the immunogenic composition comprises about a 2.8:1 molar ratio of Polysorbate 80 to protein, 0.5 mg/mL aluminum as AlPO4, mM histidine pH 6.0, and 150 mM NaCl. In some embodiments, the immunogenic composition consists essentially of 200 ug/mL LP2086 (fHBP) Subfamily B polypeptide, about a 2.8:1 molar ratio of Polysorbate 80 to protein, 0.5 mg/mL aluminum as AlPO4, 10 mM histidine pH 6.0, and 150 mM NaCl. In some embodiments, the immunogenic composition consists essentially of 200 ug/mL rLP2086 (fHBP) Subfamily A polypeptide, 200 ug/mL LP2086 (fHBP) Subfamily B polypeptide, about a 2.8:1 molar ratio of Polysorbate 80 to protein, 0.5 mg/mL of aluminum as AlPO4, 10 mM histidine pH 6.0, and 150 mM NaCl.

In some embodiments, the immunogenic composition comprises about a 2.8:1 molar ratio of Polysorbate 80 to protein, 0.5 mg/mL aluminum as AlPO4, 5 mM succinate pH 6.0, and 150 mM NaCl. In some embodiments, the immunogenic composition consists essentially of 200 ug/mL LP2086 (fHBP) Subfamily B polypeptide, about a 2.8:1 molar ratio of Polysorbate 80 to protein, 0.5 mg/mL aluminum as AlPO4, 5 mM succinate pH 6.0, and 150 mM NaCl. In some embodiments, the immunogenic composition consists essentially of 200 ug/mL rLP2086 (fHBP) Subfamily A polypeptide, 200 ug/mL LP2086 (fHBP) Subfamily B polypeptide, about a 2.8:1 molar ratio of Polysorbate 80 to protein, 0.5 mg/mL of aluminum as AlPO4, 5 mM succinate pH 6.0, and 150 mM NaCl.

In another aspect, the invention provides for a method of stabilizing the potency of a LP2086 Subfamily B polypeptide in an immunogenic composition by storing the LP2086 Subfamily B polypeptide in a buffer with a molar ratio of detergent to protein between about 0.5:1 and 10:1; between about 1:1 and about 5:1; or between about 1.4:1 and about 4.2:1. In some embodiments, the molar ratio of detergent to protein is about 2.8:1. In some embodiments the amount of detergent is sufficient to reduce polypeptide binding to silicon in a container, such as a syringe or a vial. In some embodiments, the detergent is a non-ionic detergent, such as a polysorbate detergent. In some embodiments, the detergent is Polysorbate-80.

In some embodiments, the buffer further comprises a multivalent cation. In some embodiments, the multivalent cation is calcium or aluminum. In some embodiments, the buffer comprises calcium phosphate. In some embodiments, the buffer comprises aluminum as aluminum phosphate, aluminum hydroxide, aluminum sulfate, or alum. In some embodiments, the concentration of aluminum is between about 0.1 mg/mL and 1.0 mg/mL. In some embodiments, the concentration of aluminum is about 0.5 mg/mL.

In some embodiments, the buffer further comprises histidine. In some embodiments, the concentration of histidine is between about 2 mM and about 20 mM or between about 5 mM and about 15 mM. In some embodiments, the concentration of histidine is about 10 mM. In some embodiments, the pH of the histidine is between about 5.0 and about 8.0 or between about 5.8 and about 6.0. In some embodiments, the concentration of histidine is 10 mM, pH 6.0.

In some embodiments, the buffer further comprises succinate. In some embodiments, the concentration of succinate is between about 2 mM and about 10 mM or between about 3 mM and about 7 mM. In some embodiments, the concentration of succinate is about 5 mM. In some embodiments, the pH of the succinate is between about 5.0 and about 8.0 or between about 5.8 and about 6.0. In some embodiments, the concentration of succinate is 10 mM, pH 6.0.

In some embodiments, the immunogenic composition is lyophilized. In some embodiments, the lyophilized composition is resuspended in a buffer comprising aluminum. In some embodiments, the aluminum is present as aluminum phosphate, aluminum hydroxide, aluminum sulfate, or alum.

In some embodiments, the buffer consists essentially of about a 2.8:1 molar ratio of Polysorbate 80 to protein, 0.5 mg/mL aluminum as AlPO4, 10 mM histidine pH 6.0, and 150 mM NaCl. In some embodiments, the immunogenic composition consists essentially of 200 ug/mL LP2086 (fHBP) Subfamily B polypeptide, about a 2.8:1 molar ratio of Polysorbate 80 to protein, 0.5 mg/mL aluminum as AlPO4, 10 mM histidine pH 6.0, and 150 mM NaCl.

In some embodiments, the buffer consists essentially of about a 2.8:1 molar ratio of Polysorbate 80 to protein, 0.5 mg/mL aluminum as AlPO4, 5 mM succinate pH 6.0, and 150 mM NaCl. In some embodiments, the immunogenic composition consists essentially of 200 ug/mL LP2086 (fHBP) Subfamily B polypeptide, about a 2.8:1 molar ratio of Polysorbate 80 to protein, 0.5 mg/mL aluminum as AlPO4, 5 mM succinate pH 6.0, and 150 mM NaCl.

In another aspect, the invention provides for a method of stabilizing the potency of a LP2086 Subfamily A polypeptide and a LP2086 Subfamily B polypeptide in an immunogenic composition by storing the LP2086 Subfamily A polypeptide and the LP2086 Subfamily B polypeptide in a buffer with between about 0.1 mg/mL and about 10 mg/mL aluminum and a molar ratio of detergent to protein between about 0.5:1 and 10:1. In some embodiments, the molar ratio of detergent to protein is between about 1:1 and about 5:1; or between about 1.4:1 and about 4.2:1. In some embodiments, the molar ratio of detergent to protein is about 2.8:1. In some embodiments the amount of detergent is sufficient to reduce polypeptide binding to silicon in a container, such as a syringe or a vial. In some embodiments, the detergent is a non-ionic detergent, such as a polysorbate detergent. In some embodiments, the detergent is Polysorbate-80.

In some embodiments, the aluminum is present as aluminum phosphate, aluminum hydroxide, aluminum sulfate, or alum. In some embodiments, the concentration of aluminum is about 0.5 mg/mL.

In some embodiments, the buffer further comprises histidine. In some embodiments, the concentration of histidine is between about 2 mM and about 20 mM or between about 5 mM and about 15 mM. In some embodiments, the concentration of histidine is about 10 mM. In some embodiments, the pH of the histidine is between about 5.0 and about 8.0 or between about 5.8 and about 6.0. In some embodiments, the concentration of histidine is 10 mM, pH 6.0.

In some embodiments, the buffer further comprises succinate. In some embodiments, the concentration of succinate is between about 2 mM and about 10 mM or between about 3 mM and about 7 mM. In some embodiments, the concentration of succinate is about 5 mM. In some embodiments, the pH of the succinate is between about 5.0 and about 8.0 or between about 5.8 and about 6.0. In some embodiments, the concentration of succinate is 10 mM, pH 6.0.

In some embodiments, the immunogenic composition is lyophilized. In some embodiments, the lyophilized composition is resuspended in a buffer comprising aluminum. In some embodiments, the aluminum is present as aluminum phosphate, aluminum hydroxide, aluminum sulfate, or alum.

In some embodiments, the buffer consists essentially of about a 2.8:1 molar ratio of Polysorbate 80 to protein, 0.5 mg/mL aluminum as AlPO4, 10 mM histidine pH 6.0, and 150 mM NaCl. In some embodiments, the immunogenic composition consists essentially of 200 ug/mL LP2086 (fHBP) Subfamily A polypeptide, 200 ug/mL LP2086 (fHBP) Subfamily B polypeptide, about a 2.8:1 molar ratio of Polysorbate 80 to protein, 0.5 mg/mL aluminum as AlPO4, 10 mM histidine pH 6.0, and 150 mM NaCl.

In some embodiments, the buffer consists essentially of about a 2.8:1 molar ratio of Polysorbate 80 to protein, 0.5 mg/mL aluminum as AlPO4, 5 mM succinate pH 6.0, and 150 mM NaCl. In some embodiments, the immunogenic composition consists essentially of 200 ug/mL LP2086 (fHBP) Subfamily A polypeptide, 200 ug/mL LP2086 (fHBP) Subfamily B polypeptide, about a 2.8:1 molar ratio of Polysorbate 80 to protein, 0.5 mg/mL aluminum as AlPO4, 5 mM succinate pH 6.0, and 150 mM NaCl.

In another aspect, the invention provides a method for determining the potency of a rLP2086 Subfamily A polypeptide and/or a rLP2086 Subfamily B polypeptide comprising the steps of: (a) binding a first and a second functional monoclonal antibody recognizing conformational epitopes on each subfamily protein to the immunogenic composition and (b) quantitating the antibody binding to the polypeptides. In some embodiments, the quantitation is performed by electrochemiluminescence. In some embodiments, polypeptides exhibiting epitopes recognized by both antibodies are quantitated. In some embodiments, the first antibody is conjugated to a label, such as biotin. In some embodiments, the first antibody is isolated by a compound that binds the conjugated label, such as streptavidin beads or a streptavidin column. In some embodiments, the second antibody is bound by a quantitative label. In some embodiments, the potency of the immunogenic composition is compared to the potency of a reference material.

BRIEF DESCRIPTION OF THE DRAWINGS

FIG. 1: Stability of Subfamily B in Formulations with Various Polysorbate 80 Concentrations.

FIG. 2: Accelerated Stability of Subfamily B with Various Polysorbate 80 Concentrations FIG. 3: Potency of Subfamily B at 200 µg/mL for 28 days FIG. 4: Potency of Subfamily B at 20 µg/mL for 28 days

FIG. 9: The Effect of pH, Buffer and Protein Concentration on Binding of rLP2086 Subfamily A and B FIG. 10: Visual Appearance of rLP2086 Formulations without Aluminum Phosphate

FIG. 12: Potency Results for Subfamily A for Formulation with and without AlPO4

FIG. 13: Potency Results for Subfamily B for Formulation with and without AlPO4

FIG. 19: Molar Ratio Results for Subfamily B

FIG. 20: Molar Ratio Results for rLP2086 Formulations @ 400 µg/mL

FIG. 23: Potency and Bound Molar Ratio Results for Subfamily A FIG. 24: Potency and Bound Molar Ratio Results for Subfamily B FIG. 25: Binding of Subfamily A with AlPO4 in Succinate and Histidine Buffers FIG. 26: Binding of Subfamily B with AlPO4 in Succinate and Histidine Buffers FIG. 28: pH-Dependent Binding of Subfamily A with AlPO4

FIG. 29: pH-Dependent Binding of Subfamily B with AlPO4

DETAILED DESCRIPTION OF THE INVENTION

Figure 5:
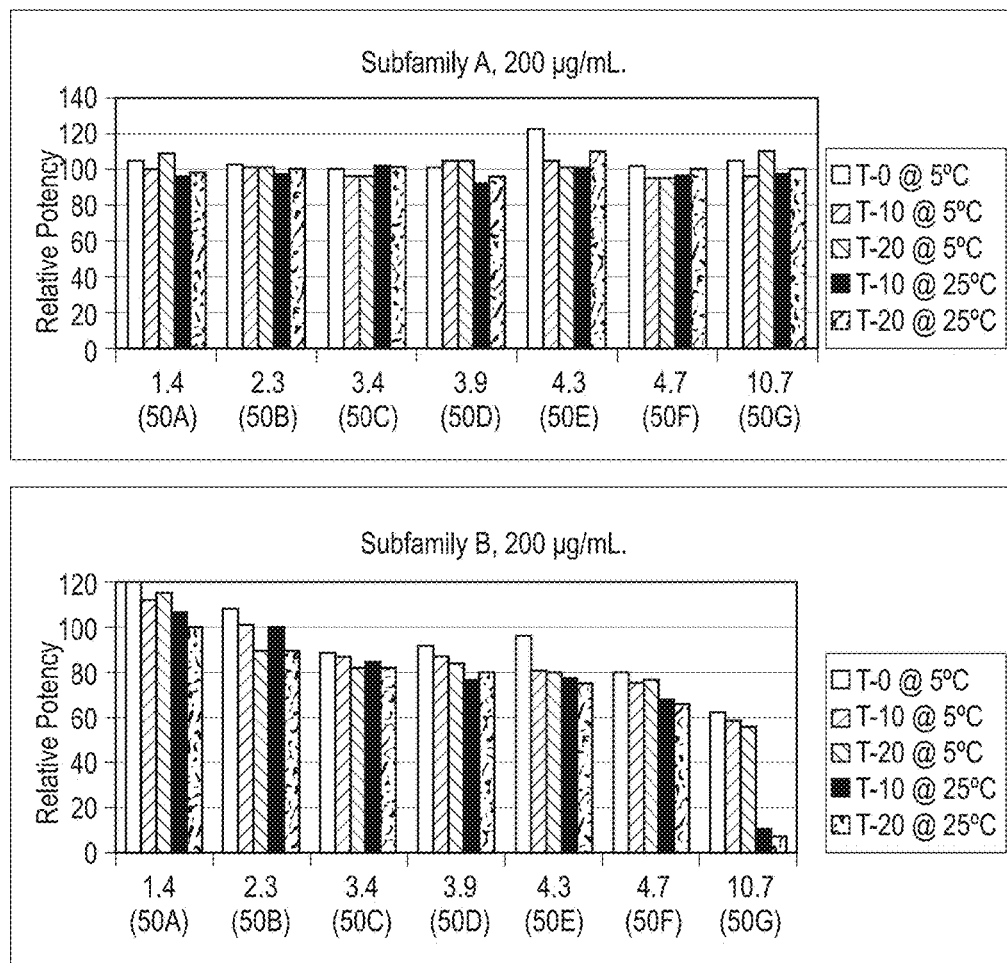
FIG. 5: Potency Results for 200 µg/mL with Different Molar Ratios

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

DEFINITIONS

As used herein, the singular forms "a," "an," and "the" include plural references unless the context clearly dictates otherwise. Thus, e.g., references to "the method" includes one or more methods, and/or steps of the type described herein and/or which will become apparent to one of ordinary skill in the art upon reading this disclosure and so forth.

As used herein, the plural forms include singular references unless the context clearly dictates otherwise. Thus, e.g., references to "the methods" includes one or more methods, and/or steps of the type described herein and/or which will become apparent to one of ordinary skill in the art upon reading this disclosure and so forth.

As used herein, "about" means within a statistically meaningful range of a value such as a stated concentration range, time frame, molecular weight, temperature or pH. Such a range can be within an order of magnitude, typically within 20%, more typically still within 10%, and even more typically within 5% of a given value or range. The allowable variation encompassed by the term "about" will depend upon the particular system under study, and can be readily appreciated by one of ordinary skill in the art. Whenever a range is recited within this application, every whole number integer within the range is also contemplated as an embodiment of the invention.

The term "adjuvant" refers to a compound or mixture that enhances the immune response to an antigen as further described and exemplified herein. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant.

The term "binding of aluminum to protein" refers to the percentage of protein molecules in a composition that are bound to aluminum. The binding of aluminum to protein can be determined using methods disclosed herein or known in the art.

The term "effective immunogenic amount" as used herein refers to an amount of a polypeptide or composition comprising a polypeptide which is effective in eliciting an immune response in a vertebrate host. For example, an effective immunogenic amount of a rLP2086 protein of this invention is an amount that is effective in eliciting an immune response in a vertebrate host. The particular "effective immunogenic dosage or amount" will depend upon the age, weight and medical condition of the host, as well as on the method of administration. Suitable doses are readily determined by persons skilled in the art.

The term "molar ratio" as used herein refers to the ratio of the number of moles of two different elements in a composition. In some embodiments, the molar ratio is the ratio of moles of detergent to moles of protein. In some embodiments, the molar ratio is the ratio of moles of Polysorbate 80 to moles of protein. Based on the protein and Polysorbate 80 concentrations, the Molar Ratio is calculated using the following equation:

$$\text{Molar Ratio} = \frac{\% PS80}{\text{mg/mL Protein}} \times 216$$

For example, a composition comprising 0.01% Polysorbate 80 and 200 µg has a detergent-to-protein molar ratio of 10.8:1 [(0.01/0.2)×216]. A ratio of 3 moles Polysorbate 80 to 2 moles of protein would be expressed as a molar ratio of PS80 to protein of 3:2. Further, if a molar ratio is recited as a single number, it refers to a ratio of that single number to 1. For example, Polysorbate 80-to-protein ratios of 0.5, 2, and 10 refer to ratios of 0.5:1, 2:1 and 10:1, respectively. As used herein, the terms "detergent to protein" molar ratio and "Polysorbate 80 to protein" molar ratio refer in general to the molar ratio of detergent (or Polysorbate 80) to protein antigens, particularly P2086 antigens. Based on the teachings disclosed herein, one of skill in the art would be able to determine how to calculate molar ratios for other detergents and the optimal molar ratio for formulations with other detergents. As used herein, a "low" molar ratio refers in general to a molar ratio of the detergent to protein antigen in the immunogenic composition that is less than a "high" molar ratio. A "high" molar ratio refers in general to a molar ratio of the detergent to protein antigen in the immunogenic composition that is greater than a "low" molar ratio. In some embodiments, a "high molar ratio" of detergent to protein refers to a molar ratio greater than 10:1. In some embodiments, a "low molar ratio" of detergent to protein refer to a molar ratio between 0.5:1 and 10:1.

The term "ORF2086" as used herein refers to Open Reading Frame 2086 from a *Neisseria* species bacteria. *Neisseria* ORF2086, the proteins encoded therefrom, fragments of those proteins, and immunogenic compositions comprising those proteins are known in the art and are described, e.g., in U.S. Patent Application Publication Nos. US 20060257413 and US 20090202593, each of which is hereby incorporated by reference in its entirety. The term "P2086" generally refers to the protein encoded by ORF2086. The P2086 proteins of the invention may be lipidated or non-lipidated. "LP2086" and "P2086" typically refer to lipidated and non-lipidated forms of a 2086 protein, respectively. The P2086 protein of the invention may be recombinant. "rLP2086" and "rP2086" typically refer to lipidated and non-lipidated forms of a recombinant 2086 protein, respectively.

The term "pharmaceutically acceptable carrier" as used herein is intended to include any and all solvents, dispersion media, coatings, antibacterial and antifungal agents, isotonic and absorption delaying agents, and the like, compatible with administration to humans or other vertebrate hosts. Typically, a pharmaceutically acceptable carrier is a carrier approved by a regulatory agency of a Federal, a state government, or other regulatory agency, or listed in the U.S. Pharmacopeia or other generally recognized pharmacopeia for use in animals, including humans as well as non-human mammals. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin. Water, saline solutions and aqueous dextrose and glycerol solutions can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting, bulking, emulsifying agents, or pH buffering agents. These compositions can take the form of solutions, suspensions, emulsion, sustained release formulations and the like. Examples of suitable pharmaceutical carriers are described in "Remington's Pharmaceutical Sciences" by E. W. Martin. The formulation should suit the mode of administration. The appropriate carrier will be evident to those skilled in the art and will depend in large part upon the route of administration.

The term "potency" refers to an antigen's ability to raise an immunogenic response. In some embodiments, potency is measured by an epitopes ability to bind to an antibody. Potency may be lost or reduced over time due to loss of antigen or epitope integrity or a change in antigen or epitope conformation. Potency may be lost or reduced due to factors including, but not limited to, light, temperature, freeze/thaw cycles, agitation, and pH. Potency can be measured by the methods disclosed herein and by assays known in the art. Such potency determination assays include, but are not limited to, animal vaccination models, serum bactericidal assays (SBA), flow cytometry, and in vitro potency assays. The preferred methods for determining potency are SBA and in vitro potency assays. A more preferred method for determining potency is SBA. In some embodiments, potency can be determined using at least one monoclonal antibody directed against at least one epitope that is involved in immune response. In some embodiments, potency of a test sample is compared against potency of a reference standard. In some embodiments, the reference standard is the test sample at $T_0$. In some embodiments, the reference standard is an immunogenic composition without a detergent. In some embodiments, the reference standard is an immunogenic composition with a detergent-to-protein molar ratio higher than 10:1.

A "protective" immune response refers to the ability of an immunogenic composition to elicit an immune response, either humoral or cell mediated, which serves to protect the subject from an infection. The protection provided need not be absolute, i.e., the infection need not be totally prevented or eradicated, if there is a statistically significant improvement compared with a control population of subjects, e.g. infected animals not administered the vaccine or immunogenic composition. Protection may be limited to mitigating the severity or rapidity of onset of symptoms of the infection. In general, a "protective immune response" would include the induction of an increase in antibody levels specific for a particular antigen in at least 50% of subjects, including some level of measurable functional antibody responses to each antigen. In particular situations, a "protective immune response" could include the induction of a two fold increase in antibody levels or a four fold increase in antibody levels specific for a particular antigen in at least 50% of subjects, including some level of measurable functional antibody responses to each antigen. In certain embodiments, opsonising antibodies correlate with a protective immune response. Thus, protective immune response may be assayed by measuring the percent decrease in the bacterial count in an opsonophagocytosis assay, for instance those described below. In some embodiments, there is a decrease in bacterial count of at least 10%, 25%, 50%, 65%, 75%, 80%, 85%, 90%, 95% or more, as compared to the bacterial count in the absence of the immunogenic composition.

The terms "protein", "polypeptide" and "peptide" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature, but which may be non-conservative), to a native sequence, preferably such that the protein maintains the ability to elicit an immunological response within an animal to which the protein is administered. Also included are post-expression modifications, e.g. glycosylation, acetylation, lipidation, phosphorylation and the like.

The term "recombinant" as used herein refers to any protein, polypeptide, or cell expressing a gene of interest that is produced by genetic engineering methods. The term "recombinant" as used with respect to a protein or polypeptide, means a polypeptide produced by expression of a recombinant polynucleotide. The proteins of the present invention may be isolated from a natural source or produced by genetic engineering methods. "Recombinant," as used herein, further describes a nucleic acid molecule, which, by virtue of its origin or manipulation, is not associated with all or a portion of the polynucleotide with which it is associated in nature. The term "recombinant" as used with respect to a host cell means a host cell which includes a recombinant polynucleotide.

The terms "stable" and "stability" refer the ability of an antigen to remain immunogenic over a period of time. Stability may be measured in potency over time. The terms "stable" and "stability" further refer to the physical, chemical, and conformational stability of the immunogenic composition. Instability of a protein composition may be caused by chemical degradation or aggregation of the protein molecules to form higher order polymers, by dissociation of the heterodimers into monomers, deglycosylation, modification of glycosylation, or any other structural modification that reduces at least one biological activity of the protein composition included in the present invention. Stability may be assessed by methods well-known in the art, including measurement of a sample's light scattering, apparent attenuation of light (absorbance, or optical density), size (e.g. by size exclusion chromatography), in vitro or in vivo biological activity and/or properties by differential scanning calorimetry (DSC). Other methods for assessing stability are known in the art and can also be used according to the present invention.

In some embodiments, an antigen in a stable formulation of the invention may maintain at least 50%, 60%, 70%, 75%, 80%, 85%, 90%, 95%, 96%, 97%, 98%, 99% or 100% potency, as compared to a reference standard, for at least 1 month, 2 months, 3 months, 4 months, 5 months, 6 months, 9 months, 12 months, 18 months, 24 months, 30 months, 36 months, 42 months, 48 months, 54 months, or 60 months. In some embodiments, an antigen in a stable formulation of the invention may maintain at least 50% potency, as compared to a reference standard, for at least 1 year, 2 years, 3 years, 4 years or 5 years. The terms "stable" and "stability" also refer to the ability of an antigen to maintain epitopes or immunoreactivity over a period of time. For example, an antigen in a stable formulation of the invention may maintain at least 50%, 60%, 70%, 75%, 80%, 85%, 90%, 95%, 96%, 97%, 98%, 99% or 100% of its epitopes or immunoreactivity, as compared to a reference standard, for at least 1 month, 2 months, 3 months, 4 months, 5 months, 6 months, 9 months, 12 months, 18 months, 24 months, 30 months, 36 months, 42 months, 48 months, 54 months, or 60 months. In some embodiments, stability is measured with respect to an environmental condition. Non-limiting examples of environmental conditions include light, temperature, freeze/thaw cycles, agitation, and pH. One of skill in the art would be able to determine the presence of antigenic epitopes or immunoreactivity using the methods disclosed herein or other methods known in the art. See, e.g., McNeil et al. Vaccine, 27: 3417-3421 (2009). In some embodiments, the stability of an antigen is measured from the date of its formulation. In some embodiments, the stability of an antigen is measured from the date of a change in its storage conditions. Non-limiting examples of changes in storage conditions include changing from frozen to refrigerated, changing from frozen to room temperature, changing from refrigerated to room temperature, changing from refrigerated to frozen, changing from room temperature to frozen, changing from room temperature to refrigerated, changing from light to dark, or introduction of agitation.

The terms "stabilizer" refers to a compound that binds to an antigen and maintains the epitopes or immunoreactivity of the antigen over a period of time. Stabilizers are known in the art. Examples of stabilizers include multivalent cations, for example, calcium or aluminum.

The term "subject" refers to a mammal, bird, fish, reptile, or any other animal. The term "subject" also includes humans. The term "subject" also includes household pets. Non-limiting examples of household pets include: dogs, cats, pigs, rabbits, rats, mice, gerbils, hamsters, guinea pigs, ferrets, birds, snakes, lizards, fish, turtles, and frogs. The term "subject" also includes livestock animals. Non-limiting examples of livestock animals include: alpaca, bison, camel, cattle, deer, pigs, horses, llamas, mules, donkeys, sheep, goats, rabbits, reindeer, yak, chickens, geese, and turkeys.

The terms "vaccine" or "vaccine composition", which are used interchangeably, refer to pharmaceutical compositions comprising at least one immunogenic composition that induces an immune response in a subject.

General Description

The present invention arises out of the novel discovery that rLP2086 Subfamily B antigens, but not rLP2086 Subfamily A antigens, lose potency over time in a bivalent vaccine formulation and are thus unstable. By varying components in the bivalent formulation, it was determined that high molar ratios of detergent to protein in the bivalent vaccine formulation resulted in rLP2086 Subfamily B antigen specific instability. Reducing the molar ratio of detergent to protein in bivalent and monovalent formulations resulted in increased stability, as determined by maintenance of potency over time, of rLP2086 Subfamily B antigen without affecting the stability of rLP2086 Subfamily A antigen. This result is surprising because lipoproteins are typically purified and stored using high detergent concentrations to prevent aggregation of their hydrophobic lipid moieties. Accordingly, in some embodiments, the invention provides an immunogenic composition comprising a rLP2086 Subfamily B antigen and low molar ratio of detergent to protein. In some embodiments, the invention provides a method of maintaining stability of a rLP2086 Subfamily B antigen in an immunogenic composition comprising the step of storing the rLP2086 Subfamily B antigen in a buffer comprising a low molar ratio of detergent to protein.

Further studies revealed that low molar ratio formulations resulted in aggregation of rLP2086 Subfamily A and B antigens upon agitation of the low molar ratio immunogenic compositions. Increasing aluminum concentration in low molar ratio compositions, however, prevented aggregation of rLP2086 Subfamily A and B antigens, even with agitation. Moreover, rLP0286 Subfamily A antigens are more sensitive to the effects of low detergent molar ratios in the absence of aluminum. Accordingly, in some embodiments, the invention provides an immunogenic composition comprising rLP2086 Subfamily A antigen, rLP2086 Subfamily B antigen, high concentration aluminum and low molar ratio of detergent to protein. In some embodiments, the invention provides a method of maintaining stability of rLP2086 Subfamily A antigen and rLP2086 Subfamily B antigen in an immunogenic composition comprising the step of storing the rLP2086 Subfamily A antigen and rLP2086 Subfamily B antigen in a buffer comprising a high concentration of aluminum and a low molar ratio of detergent to protein.

Immunogenic Compositions

Immunogenic compositions that include a protein encoded by a nucleotide sequence from *Neisseria meningitidis* ORF2086 are known in the art. Exemplary immunogenic compositions include those described in US patent application publication numbers US 20060257413 and US 20090202593, which are incorporated herein by reference in their entirety. Such immunogenic compositions described therein include a protein exhibiting bactericidal activity identified as ORF2086 protein, immunogenic portions thereof, and/or biological equivalents thereof. The ORF2086 protein refers to a protein encoded by open reading frame 2086 of *Neisseria* species.

The protein may be a recombinant protein or an isolated protein from native *Neisseria* species. For example, *Neisseria* ORF2086 proteins may be isolated from bacterial strains, such as those of *Neisseria* species, including strains of *Neisseria meningitidis* (serogroups A, B, C, D, W-135, X, Y, Z, and 29E), *Neisseria gonorrhoeae*, and *Neisseria lactamica*, as well as immunogenic portions and/or biological equivalents of said proteins.

The ORF2086 proteins include 2086 Subfamily A proteins and Subfamily B proteins, immunogenic portions thereof, and/or biological equivalents thereof. The ORF2086 proteins or equivalents thereof, etc. may be lipidated or non-lipidated. Preferably, the *Neisseria* ORF2086 protein is lipidated.

In an one embodiment, the immunogenic composition includes an isolated protein having at least 95% amino acid sequence identity to a protein encoded by a nucleotide sequence from *Neisseria* ORF2086.

In one embodiment, the immunogenic composition includes an isolated protein having at least 95% amino acid sequence identity to a Subfamily A protein encoded by a nucleotide sequence from *Neisseria* ORF2086. Preferably, the immunogenic composition includes an isolated Subfamily A protein encoded by a nucleotide sequence from *Neisseria* ORF2086.

In another embodiment, the immunogenic composition includes an isolated protein having at least 95% amino acid sequence identity to a Subfamily B protein encoded by a nucleotide sequence from *Neisseria* ORF2086. Preferably, the immunogenic composition includes an isolated Subfamily B protein encoded by a nucleotide sequence from *Neisseria* ORF2086. In some embodiments, the ORF2086 Subfamily B protein is a B01 variant.

In yet another embodiment, the immunogenic composition includes an isolated protein having at least 95% amino acid sequence identity to a Subfamily A protein encoded by a nucleotide sequence from *Neisseria* ORF2086, and an isolated protein having at least 95% amino acid sequence identity to a Subfamily B protein encoded by a nucleotide sequence from *Neisseria* ORF2086. Preferably, the immunogenic composition includes an isolated Subfamily A protein encoded by a nucleotide sequence from *Neisseria* ORF2086 and an isolated Subfamily B protein encoded by a nucleotide sequence from *Neisseria* ORF2086.

In one embodiment, the immunogenic composition includes a 1:1 ratio of a Subfamily A protein to a Subfamily B protein.

The immunogenic composition may include a protein encoded by a nucleotide sequence from *Neisseria* ORF2086, polynucleotides, or equivalents thereof as the sole active immunogen in the immunogenic composition. Alternatively, the immunogenic composition may further include active immunogens, including other *Neisseria* sp. immunogenic polypeptides, or immunologically-active proteins of one or more other microbial pathogens (e.g. virus, prion, bacterium, or fungus, without limitation) or capsular polysaccharide. The compositions may comprise one or more desired proteins, fragments or pharmaceutical compounds as desired for a chosen indication.

Any multi-antigen or multi-valent immunogenic composition is contemplated by the present invention. For example, the immunogenic composition may include combinations of two or more ORF2086 proteins, a combination of ORF2086 protein with one or more Por A proteins, a combination of ORF2086 protein with *meningococcus* serogroup A, C, Y and W135 polysaccharides and/or polysaccharide conjugates, a combination of ORF2086 protein with *meningococcus* and *pneumococcus* combinations, or a combination of any of the foregoing in a form suitable for a desired administration, e.g., for mucosal delivery. Persons of skill in the art would be readily able to formulate such multi-antigen or multi-valent immunologic compositions.

The present invention also contemplates multi-immunization regimens wherein any composition useful against a pathogen may be combined therein or therewith the compositions of the present invention. For example, without limitation, a patient may be administered the immunogenic composition of the present invention and another immunological composition for immunizing against human papillomavirus virus (HPV), such as the HPV vaccine GARDASIL®, as part of a multi-immunization regimen. Persons of skill in the art would be readily able to select immunogenic compositions for use in conjunction with the immunogenic compositions of the present invention for the purposes of developing and implementing multi-immunization regimens.

The ORF2086 polypeptides, fragments and equivalents can be used as part of a conjugate immunogenic composition; wherein one or more proteins or polypeptides are conjugated to a carrier in order to generate a composition that has immunogenic properties against several serotypes and/or against several diseases. Alternatively, one of the ORF2086 polypeptides can be used as a carrier protein for other immunogenic polypeptides. Formulation of such immunogenic compositions is well known to persons skilled in this field.

Immunogenic compositions of the invention preferably include a pharmaceutically acceptable carrier. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. Suitable pharmaceutically acceptable carriers include, for example, one or more of water, saline, phosphate buffered saline, dextrose, glycerol, ethanol and the like, as well as combinations thereof.

Pharmaceutically acceptable carriers may further include minor amounts of auxiliary substances such as wetting or emulsifying agents, preservatives or buffers, which enhance the shelf life or effectiveness of the antibody. The preparation and use of pharmaceutically acceptable carriers is well known in the art. Except insofar as any conventional media or agent is incompatible with the active ingredient, use thereof in the immunogenic compositions of the present invention is contemplated.

Immunogenic compositions can be administered parenterally, e.g., by injection, either subcutaneously or intramuscularly, as well as orally or intranasally. Methods for intramuscular immunization are described by Wolff et al. *Biotechniques;* 11(4):474-85, (1991). and by Sedegah et al. *PNAS* Vol. 91, pp. 9866-9870, (1994). Other modes of administration employ oral formulations, pulmonary formulations, suppositories, and transdermal applications, for example, without limitation. Oral formulations, for example, include such normally employed excipients as, for example, pharmaceutical grades of mannitol, lactose, starch, magnesium stearate, sodium saccharine, cellulose, magnesium carbonate, and the like, without limitation. Preferably, the immunogenic composition is administered intramuscularly.

The immunogenic compositions of the invention can include one or more adjuvants. Exemplary adjuvants include, but are not limited to aluminum hydroxide; aluminum phosphate; STIMULON™ QS-21 (Aquila Biopharmaceuticals, Inc., Framingham, Mass.); MPL™ (3-O-deacylated monophosphoryl lipid A; Corixa, Hamilton, Mont.), 529 (an amino alkyl glucosamine phosphate compound, Corixa, Hamilton, Mont.), IL-12 (Genetics Institute, Cambridge, Mass.); GM-CSF (Immunex Corp., Seattle, Wash.); N-acetyl-muramyl-L-theronyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphos-phoryloxy-ethylamin e) (CGP 19835A, referred to as MTP-PE); and cholera toxin. In certain preferred embodiments, the adjuvant is QS-21.

Additional exemplary adjuvants include non-toxic derivatives of cholera toxin, including its A subunit, and/or conjugates or genetically engineered fusions of the *N. meningitidis* polypeptide with cholera toxin or its B subunit ("CTB"), procholeragenoid, fungal polysaccharides, including schizophyllan, muramyl dipeptide, muramyl dipeptide ("MDP") derivatives, phorbol esters, the heat labile toxin of *E. coli*, block polymers or saponins Aluminum phosphate has been used as the adjuvant in a phase 1 clinical trial to a concentration 0.125 mg/dose, much lower than the limit of 0.85 mg/dose specified by the US Code of Federal Regulations [610.15(a)]. Aluminum-containing adjuvants are widely used in humans to potentiate the immune response of antigens when administered intramuscularly or subcutaneously.

In certain preferred embodiments, the proteins of this invention are used in an immunogenic composition for oral administration which includes a mucosal adjuvant and used for the treatment or prevention of *N. meningitidis* infection in a human host. The mucosal adjuvant can be a cholera toxin; however, preferably, mucosal adjuvants other than cholera toxin which may be used in accordance with the present invention include non-toxic derivatives of a cholera holotoxin, wherein the A subunit is mutagenized, chemically modified cholera toxin, or related proteins produced by modification of the cholera toxin amino acid sequence. For a specific cholera toxin which may be particularly useful in preparing immunogenic compositions of this invention, see the mutant cholera holotoxin E29H, as disclosed in Published International Application WO 00/18434, which is hereby incorporated herein by reference in its entirety. These may be added to, or conjugated with, the polypeptides of this invention. The same techniques can be applied to other molecules with mucosal adjuvant or delivery properties such as *Escherichia coli* heat labile toxin (LT). Other compounds with mucosal adjuvant or delivery activity may be used such as bile; polycations such as DEAE-dextran and polyornithine; detergents such as sodium dodecyl benzene sulphate; lipid-conjugated materials; antibiotics such as streptomycin; vitamin A; and other compounds that alter the structural or functional integrity of mucosal surfaces. Other mucosally active compounds include derivatives of microbial structures such as MDP; acridine and cimetidine. STIMULON™ QS-21, MPL, and IL-12, as described above, may also be used.

The immunogenic compositions of this invention may be delivered in the form of ISCOMS (immune stimulating complexes), ISCOMS containing CTB, liposomes or encapsulated in compounds such as acrylates or poly(DL-lactide-co-glycoside) to form microspheres of a size suited to adsorption. The proteins of this invention may also be incorporated into oily emulsions.

An amount (i.e., dose) of immunogenic composition that is administered to the patient can be determined in accordance with standard techniques known to those of ordinary skill in the art, taking into consideration such factors as the particular antigen, the adjuvant (if present), the age, sex, weight, species, condition of the particular patient, and the route of administration.

For example, a dosage for an adolescent human patient may include at least 0.1 µg, 1 µg, 10 µg, or 50 µg of a *Neisseria* ORF2086 protein, and at most 80 µg, 100 µg, 150 µg, or 200 µg of a *Neisseria* ORF2086 protein. Any minimum value and any maximum value may be combined to define a suitable range.

In Vitro Potency Assay

Potency is determined by quantitation of functional epitopes in Subfamily A and Subfamily B proteins in an immunogenic composition using conformation-specific monoclonal antibodies against a rLP2086 reference material. Potency is determined by quantitative measure of the functional epitopes in Subfamily A or Subfamily B rLP2086 proteins that will elicit immune response in vivo to generate bactericidal antibodies. Quantitative technology is used for potency assay with selected monoclonal antibodies (mAbs). Two functional monoclonal antibodies that are conformational and non-overlapping are selected for each Subfamily rLP2086 protein in the immunogenic compositions. Between the two purified monoclonal antibodies, the first antibody is conjugated to a first tag, wherein the first tag is used to capture of rLP2086 protein molecule. In some embodiments, the first tag is biotin, glutathione-S transferase (GST), a 6×His tag, or beads (e.g. carboxylated polystyrene beads or paramagnetic beads). In some embodiments the first tag is captured with streptavidin beads, a streptavidin column, nickel beads, a nickel column, centrifugation or with a magnetic field. The second antibody is conjugated to a second tag, wherein the second tag is quantifiable. In some embodiments, the second tag is biotin, horseradish peroxidase (HRP), a fluorophore or a radiolabel. In some embodiments, the second tag is detected with streptavidin conjugated to a fluorophore or HRP, by electrochemiluminescence, detection of fluorescence, or detection of radioactivity. Only the proteins that exhibit both epitopes recognized by the two mAbs in each immunogenic composition will be measured. Changes in any one or both epitopes of the protein will be reflected. The potency of the sample is reported relative to the potency of the reference material.

In some embodiments, the invention encompasses a method for determining the potency of a 2086 protein. In some embodiments, the method comprises the steps of: (1) incubating a first monoclonal Ab and a second mAb with an immunogenic composition comprising a 2086 protein, wherein the first mAb is conjugated to a first tag that is used to capture the mAb and the second mAb is conjugated to a second tag that is detectable and wherein the first and second mAbs are directed to different conformational epitopes on a 2086 reference protein; (2) capturing the first mAb-bound 2086 protein using the first tag; and (3) detecting and quantifying the amount of captured second mAb-bound 2086 protein using the second tag. In some embodiments, the 2086 protein is a Subfamily A protein. In some embodiments, the 2086 protein is a Subfamily B protein. In some embodiments, the 2086 protein is lipidated. In some embodiments, the 2086 protein is non-lipidated. In some embodiments, the 2086 protein is recombinant. In some embodiments, the first tag is biotin, a 6×His tag, or beads (e.g. carboxylated polystyrene beads or paramagnetic beads). In some embodiments, the first tag is captured with streptavidin beads, a streptavidin column, glutathione beads, glutathione column, nickel beads, a nickel column, centrifugation or with a magnetic field. In some embodiments, the second tag is biotin, HRP, a fluorophore or a radiolabel. In some embodiments, the second tag is detected with streptavidin conjugated to a fluorophore or HRP, by electrochemiluminescence, detection of fluorescence, or detection of radioactivity. In some embodiments, the immunogenic composition comprises multiple 2086 protein variants.

Stability of rLP2086 Subfamily B Antigen Potency

In some embodiments, the invention provides an immunogenic composition for stabilizing a rLP2086 Subfamily B antigens over time comprising a buffer with a low detergent-to-protein molar ratio.

In some embodiments, the detergent-to-protein molar ratio in the immunogenic composition is between about 0.5 and about 10. In some embodiments, the detergent-to-protein molar ratio in the immunogenic composition is between about 1 and about 5. In some embodiments, the detergent-to-protein molar ratio in the immunogenic composition is between about 1.4 and about 4.2. In some embodiments, the detergent-to-protein molar ratio in the immunogenic composition is about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.5, about 6.0, about 6.5, about 7.0, about 7.5, about 8.0, about 8.5, about 9.0, about 9.5, or about 10. In some embodiments, the detergent is a non-ionic detergent. In some embodiments, the detergent is a polysorbate detergent. In some embodiments, the detergent is Polysorbate 80.

In some embodiments, the immunogenic composition further comprises a multivalent cation. In some embodiments, the multivalent cation is calcium or aluminum. In some embodiments, the aluminum is present as one or more of AlPO4, Al(OH)$_3$, Al$_2$(SO$_4$)$_3$ and alum. In some embodiments, the immunogenic composition comprises between about 0.1 mg/mL and about 1 mg/mL; between about 0.25 mg/mL and about 0.75 mg/mL, or between about 0.4 mg/mL and about 0.6 mg/mL aluminum. In some embodiments, the immunogenic composition comprises about 0.1 mg/mL, about 0.15 mg/mL; about 0.2 mg/mL, about 0.25 mg/mL, about 0.3 mg/mL, about 0.35 mg/mL, about 0.4 mg/mL, about 0.45 mg/mL, about 0.5 mg/mL, about 0.55 mg/mL, about 0.6 mg/mL, about 0.65 mg/mL, about 0.7 mg/mL, about 0.75 mg/mL, about 0.8 mg/mL, about 0.85 mg/mL, 0.9 mg/mL, about 0.95 mg/mL, or about 1 mg/mL aluminum. In some embodiments, there is at least 90%, at least 95%, at least 96%, at least 97%, at least 98%, at least 99% or 100% binding of aluminum to protein.

In some embodiments, the immunogenic composition further comprises a buffer comprising histidine. In some embodiments, the concentration of histidine is between about 2 mM and about 20 mM; between about 5 mM and about 15 mM, or between about 8 mM and 12 mM. In some embodiments, the concentration of histidine is about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

In some embodiments, the immunogenic composition further comprises a buffer comprising succinate. In some embodiments, the concentration of succinate is between about 2 mM and about 20 mM; between about 2 mM and about 10 mM, or between about 3 mM and 7 mM. In some embodiments, the concentration of succinate is about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

In some embodiments, the pH of the immunogenic composition has a pH between about 5.0 and about 8.0; between about 5.5 and about 7.0; or between about 5.8 and about 6.0. In some embodiments, the pH of the immunogenic composition has a pH about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

In some embodiments, the formulation of MnB rLP2086 Subfamily B protein antigen immunogenic composition is 10 mM histidine-buffered saline, pH 6.0, containing 0.5 mg/mL aluminum as aluminum phosphate and Polysorbate 80:protein molar ratio of 2.8.

In some embodiments, the formulation of MnB rLP2086 Subfamily B protein antigen immunogenic composition is 5 mM succinate-buffered saline, pH 6.0, containing 0.5 mg/mL aluminum as aluminum phosphate and Polysorbate 80:protein molar ratio of 2.8.

In some embodiments, the invention provides a method of stabilizing a rLP2086 Subfamily B antigens over time comprising storing the antigens in a buffer with a low detergent-to-protein molar ratio.

In some embodiments, the detergent-to-protein molar ratio in the buffer is between about 0.5 and about 10. In some embodiments, the detergent-to-protein molar ratio in the buffer is between about 1 and about 5. In some embodiments, the detergent-to-protein molar ratio in the buffer is between about 1.4 and about 4.2. In some embodiments, the detergent-to-protein molar ratio in the buffer is about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.5, about 6.0, about 6.5, about 7.0, about 7.5, about 8.0, about 8.5, about 9.0, about 9.5, or about 10. In some embodiments, the detergent is a non-ionic detergent. In some embodiments, the detergent is a polysorbate detergent. In some embodiments, the detergent is polysorbate-80.

In some embodiments, the buffer further comprises a multivalent cation. In some embodiments, the multivalent cation is calcium or aluminum. In some embodiments, the aluminum is present as one or more of AlPO4, Al(OH)$_3$, Al$_2$(SO$_4$)$_3$ and alum. In some embodiments, the stabilizer in the buffer is between about 0.1 mg/mL and about 1 mg/mL; between about 0.25 mg/mL and about 0.75 mg/mL, or between about 0.4 mg/mL and about 0.6 mg/mL aluminum. In some embodiments, the stabilizer in the buffer is about 0.1 mg/mL, about 0.15 mg/mL; about 0.2 mg/mL, about 0.25 mg/mL, about 0.3 mg/mL, about 0.35 mg/mL, about 0.4 mg/mL, about 0.45 mg/mL, about 0.5 mg/mL, about 0.55 mg/mL, about 0.6 mg/mL, about 0.65 mg/mL, about 0.7 mg/mL, about 0.75 mg/mL, about 0.8 mg/mL, about 0.85 mg/mL, 0.9 mg/mL, about 0.95 mg/mL, or about 1 mg/mL aluminum. In some embodiments, there is at least 90%, at least 95%, at least 96%, at least 97%, at least 98%, at least 99% or 100% binding of aluminum to protein.

In some embodiments, the buffer further comprises histidine. In some embodiments, the concentration of histidine is between about 2 mM and about 20 mM; between about 5 mM and about 15 mM, or between about 8 mM and 12 mM. In some embodiments, the concentration of histidine is about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

In some embodiments, the buffer further comprises succinate. In some embodiments, the concentration of succinate is between about 2 mM and about 20 mM; between about 2 mM and about 10 mM, or between about 3 mM and 7 mM. In some embodiments, the concentration of succinate is about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

In some embodiments, the buffer has a pH of between about 5.0 and about 8.0; between about 5.5 and about 7.0; or between about 5.8 and about 6.0. In some embodiments, the buffer has a pH of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

In some embodiments, the buffer in which the MnB rLP2086 Subfamily B protein antigen is stored is 10 mM histidine-buffered saline, pH 6.0, containing 0.5 mg/mL aluminum as aluminum phosphate and Polysorbate 80:protein molar ratio of 2.8.

In some embodiments, the buffer in which the MnB rLP2086 Subfamily B protein antigen is stored is 5 mM succinate-buffered saline, pH 6.0, containing 0.5 mg/mL aluminum as aluminum phosphate and Polysorbate 80:protein molar ratio of 2.8.

Stability of rLP2086 Subfamily A and B Antigen Potency

In some embodiments, the invention provides an immunogenic composition for stabilizing rLP2086 Subfamily A and/or rLP2086 Subfamily B antigens over time comprising a buffer with a high stabilizer concentration and a low detergent-to-protein molar ratio.

In some embodiments, the detergent-to-protein molar ratio in the immunogenic composition is between about 0.5 and about 10. In some embodiments, the detergent-to-protein molar ratio in the immunogenic composition is between about 1 and about 5. In some embodiments, the detergent-to-protein molar ratio in the immunogenic composition is between about 1.4 and about 4.2. In some embodiments, the detergent-to-protein molar ratio in the immunogenic composition is about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.5, about 6.0, about 6.5, about 7.0, about 7.5, about 8.0, about 8.5, about 9.0, about 9.5, or about 10. In some embodiments, the detergent is a non-ionic detergent. In some embodiments, the detergent is a polysorbate detergent. In some embodiments, the detergent is Polysorbate 80.

In some embodiments, the immunogenic composition further comprises a multivalent cation. In some embodiments, the multivalent cation is calcium or aluminum. In some embodiments, the aluminum is present as one or more of AlPO4, Al(OH)$_3$, Al$_2$(SO$_4$)$_3$ and alum. In some embodiments, the immunogenic composition comprises between about 0.1 mg/mL and about 1 mg/mL; between about 0.25 mg/mL and about 0.75 mg/mL, or between about 0.4 mg/mL and about 0.6 mg/mL aluminum. In some embodiments, the immunogenic composition comprises about 0.1 mg/mL, about 0.15 mg/mL; about 0.2 mg/mL, about 0.25 mg/mL, about 0.3 mg/mL, about 0.35 mg/mL, about 0.4 mg/mL, about 0.45 mg/mL, about 0.5 mg/mL, about 0.55 mg/mL, about 0.6 mg/mL, about 0.65 mg/mL, about 0.7 mg/mL, about 0.75 mg/mL, about 0.8 mg/mL, about 0.85 mg/mL, 0.9 mg/mL, about 0.95 mg/mL, or about 1 mg/mL aluminum. In some embodiments, there is at least 90%, at least 95%, at least 96%, at least 97%, at least 98%, at least 99% or 100% binding of aluminum to protein.

In some embodiments, the immunogenic composition further comprises a buffer comprising histidine. In some embodiments, the concentration of histidine is between about 2 mM and about 20 mM; between about 5 mM and about 15 mM, or between about 8 mM and 12 mM. In some embodiments, the concentration of histidine is about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

In some embodiments, the immunogenic composition further comprises a buffer comprising succinate. In some embodiments, the concentration of succinate is between about 2 mM and about 20 mM; between about 2 mM and about 10 mM, or between about 3 mM and 7 mM. In some embodiments, the concentration of succinate is about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

In some embodiments, the immunogenic composition has a pH of between about 5.0 and about 8.0; between about 5.5 and about 7.0; or between about 5.8 and about 6.0. In some embodiments, the immunogenic composition has a pH of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

In some embodiments, the formulation of MnB rLP2086 Subfamily A and B protein antigens is 10 mM histidine-buffered saline, pH 6.0, containing 0.5 mg/mL aluminum as aluminum phosphate and Polysorbate 80:protein molar ratio of 2.8.

In some embodiments, the formulation of MnB rLP2086 Subfamily B protein antigen immunogenic composition is 5 mM succinate-buffered saline, pH 6.0, containing 0.5 mg/mL aluminum as aluminum phosphate and Polysorbate 80:protein molar ratio of 2.8.

In some embodiments, the invention provides a method of stabilizing rLP2086 Subfamily A and/or rLP2086 Subfamily B antigens over time comprising storing the antigens in a buffer with a high stabilizer concentration and a low detergent-to-protein molar ratio.

In some embodiments, the detergent-to-protein molar ratio less than 10:1. In some embodiments, the detergent-to-protein molar ratio in the buffer is between about 0.5 and about 10. In some embodiments, the detergent-to-protein molar ratio in the buffer is between about 1 and about 5. In some embodiments, the detergent-to-protein molar ratio in the buffer is between about 1.4 and about 4.2. In some embodiments, the detergent-to-protein molar ratio in the buffer is about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.5, about 6.0, about 6.5, about 7.0, about 7.5, about 8.0, about 8.5, about 9.0, about 9.5, or about 10. In some embodiments, the detergent is a non-ionic detergent. In some embodiments, the detergent is a polysorbate detergent. In some embodiments, the detergent is Polysorbate 80.

In some embodiments, the stabilizer in the buffer is a multivalent cation. In some embodiments, the multivalent cation is calcium or aluminum. In some embodiments, the aluminum is present as one or more of AlPO4, Al(OH)$_3$, Al$_2$(SO$_4$)$_3$ and alum. In some embodiments, the stabilizer in the buffer is between about 0.1 mg/mL and about 1 mg/mL; between about 0.25 mg/mL and about 0.75 mg/mL, or between about 0.4 mg/mL and about 0.6 mg/mL aluminum. In some embodiments, the stabilizer in the buffer is about 0.1 mg/mL, about 0.15 mg/mL; about 0.2 mg/mL, about 0.25 mg/mL, about 0.3 mg/mL, about 0.35 mg/mL, about 0.4 mg/mL, about 0.45 mg/mL, about 0.5 mg/mL, about 0.55 mg/mL, about 0.6 mg/mL, about 0.65 mg/mL, about 0.7 mg/mL, about 0.75 mg/mL, about 0.8 mg/mL, about 0.85 mg/mL, 0.9 mg/mL, about 0.95 mg/mL, or about 1 mg/mL aluminum. In some embodiments, there is at least 90%, at least 95%, at least 96%, at least 97%, at least 98%, at least 99% or 100% binding of aluminum to protein.

In some embodiments, the buffer further comprises histidine. In some embodiments, the concentration of histidine is between about 2 mM and about 20 mM; between about 5 mM and about 15 mM, or between about 8 mM and 12 mM. In some embodiments, the concentration of histidine is about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

In some embodiments, the buffer further comprises succinate. In some embodiments, the concentration of succinate is between about 2 mM and about 20 mM; between about 2 mM and about 10 mM, or between about 3 mM and 7 mM. In some embodiments, the concentration of succinate is about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

In some embodiments, the buffer has a pH of between about 5.0 and about 8.0; between about 5.5 and about 7.0; or between about 5.8 and about 6.0. In some embodiments, the buffer has a pH of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

In some embodiments, the buffer that the MnB rLP2086 Subfamily A and B protein antigens are stored in is 10 mM histidine-buffered saline, pH 6.0, containing 0.5 mg/mL aluminum as aluminum phosphate and Polysorbate 80:protein molar ratio of 2.8.

In some embodiments, the buffer that the MnB rLP2086 Subfamily A and B protein antigens are stored in is 5 mM succinate-buffered saline, pH 6.0, containing 0.5 mg/mL aluminum as aluminum phosphate and Polysorbate 80:protein molar ratio of 2.8.

In order that this invention may be better understood, the following examples are set forth. The examples are for the purpose of illustration only and are not to be construed as limiting the scope of the invention.

All references cited herein are hereby incorporated by reference.

EXAMPLES

Example 1

Experimental Procedures

Determination of Aluminum Binding

A composition comprising aluminum and at least one protein antigen was centrifuged such that the aluminum was pelleted. Centrifugation of aluminum absorbed proteins is known in the art. See e.g., Egan et al., Vaccine, Vol. 27(24): 3175-3180 (2009). Aluminum-bound protein was also pelleted, while non-aluminum-bound protein remained in the supernatant. Total protein in the supernatant and pellet were determined by Lowry Assay. The percentage bound protein was calculated by dividing the total protein in the supernatant by the total protein added to the composition and multiplying by 100%. Similarly, the percentage unbound protein was calculated by dividing the total protein in the supernatant by the total protein added to the composition and multiplying by 100%.

For compositions comprising both Subfamily A and Subfamily B antigens, the individual Subfamily A and B protein concentrations in the supernatant were determined by ion-exchange chromatography. The separation and elution of Subfamily A and B proteins was carried out using a strong anion column and a high salt concentration eluent. Both Subfamily A and B proteins were detected and quantified using a fluorescence detector set at Excitation=280 run and Emission=310 run. Subfamily A and Subfamily B proteins elute at distinct retention times and were quantified using a standard curve generated against a rLP2086 protein reference material. The percentage unbound protein was calculated by dividing the total protein in the supernatant by the total protein added to the composition and multiplying by 100%. The percentage bound protein was calculated by subtracting the percentage unbound protein from 100%.

In Vitro Potency Assay

The rLP2086 potency assay is a homogeneous capture assay or sandwich assay that relies on two functional monoclonal antibodies that recognize conformational and non-overlapping epitopes on a single protein molecule of the rLP2086 drug substance. One purified monoclonal antibody serves as the capture antibody (mAb) and is chemically conjugated to carboxylated polystyrene beads which have a unique color-coded identifier. The second antibody is biotinylated and serves as a detection antibody that is subsequently bound by streptavidin conjugated to the fluorophore R-phycoerythrin (SA-PE). The fluidics of a Bio-Plex detection instrument quantifies individual microspheres and their associated SA-PE signal. A fluorescence signal from the R-phycoerythrin associated with the microsphere will be detected only by ternary complex formation between bead-conjugated antibody, antigen, and detection antibody and will be proportional to the number of functional epitopes in the rLP2086 samples. A change in one or both epitopes resulting in a loss of fluorescence relative to a reference standard will indicate a loss in potency.

Reagents
Monoclonal antibody conjugated microspheres (conjugated to Luminex MicroPlex Microsphere bead region #12 or to bead region #66).
Biotinylated monoclonal antibody.
rLP2086 reference materials, Subfamilies A and B, 2 mg/ml. Store at −70° C.
rLP2086 Subfamily A and B bivalent control
Streptavidin, R-phycoerythrin conjugated, lyophilized
Buffers
10 mM Histidine, 150 mM NaCl, pH 6.0
5% w/v polysorbate 80 (PS-80) in 0.85% w/v saline.
Matrix Buffer (10 mM Histidine, 0.02% polysorbate 80, 150 mM NaCl, pH 6.0).
Assay Buffer (PBS, pH 7.4 with 0.1% BSA, 0.02% polysorbate 80, 0.1% azide).
100× Streptavidin, R-phycoerythrin-conjugated (SA-PE)—Open vial of lyophilized streptavidin, R-phycoerythrin and add 1 mL of distilled water. Vortexed until completely dissolved.
Procedure
200 μL of Subfamily A protein and 200 μL of Subfamily B protein were added to 600 μL of Matrix Buffer for a concentration of 400 μg/ml of each subfamily. A standard curve of eight concentrations (3333-1.5 ng/mL) was generated by diluting the stock solution in Assay Buffer.

200 μL of the bivalent control was added to 800 μL of Matrix Buffer for a concentration of 400 μg/mL of each subfamily. The 400 μg/mL stock to make 100, 50, and 12.5 ng/mL working concentrations diluted in Assay Buffer. 100 and 12.5 ng/mL represented high and low controls (CH) and (CL) respectively.

Test samples were diluted in Matrix Buffer to a concentration of 400 μg/mL. 100, 50, and 12.5 ng/mL working solutions were prepared from the 400 μg/mL stock.

A homogenous assay mixture using a conjugated bead concentration of $2 \times 10^5$ beads/mL and a detection antibody concentration of 30 μg/mL in Assay Buffer was prepared. A sample plate was prepared by adding 0.4 mL of standard, control, sample or blank to a 2 mL 96-well deep well plate. The filters of an 96-well MultiScreen$_{HTS}$-BV filter plate were pre-wet by adding 100 μL of Assay Buffer, which was then drawn through the filter by vacuum suction. 25 μL of the prepared homogenous assay mixture was added to 96-well plate. 25 μL of each standard, control, sample or blank solution was added to each well of the 96-well filter plate. The plates were incubated at room temperature for one hour with shaking After the antigen-antibody incubation buffer was removed by vacuum aspiration through the filter. The filter of each well was washed three times with 100 μL of Assay Buffer followed by vacuum aspiration. After the final wash, 50 μL of 1×SA-PE was added to each well. The plate was incubated 10 minutes at room temperature with shaking on a titer in the dark.

Following the SA-PE incubation, 75 μL of Assay Buffer was added to each well of the plate for a total volume of 125 μL. The plate was immediately read on a Bio-Plex 200 System.

Serum Bactericidal Assay

New Zealand White female rabbits, 2.5-3.0 kg, obtained from Charles River Canada (St. Constant, QC, Canada), were prescreened by whole cell ELISA to identify those with low reactivity against two different meningococcal strains (one from each P2086 subfamily). The rabbits, in general, had very low backgrounds, and those with the lowest values were selected for use. The rabbits were vaccinated intramuscularly at weeks 0, 4, and 9 with either monovalent rLP2086-A05, monovalent rLP2086-B01 or a bivalent r LP2086-A05+B01 vaccine. Each dose contained 100 m of protein for the monovalent vaccines and 100 m of each protein for the bivalent vaccine, formulated in 10 mM histidine buffer pH 6.0, 150 mM NaCl, 0.02% Polysorbate 80 and 250 μg AlPO4. The vaccine was injected intramuscularly into the right hind leg (0.5 ml/dose). As a control, one group of rabbits was vaccinated with the formulation buffer alone. Pre-immune (week 0) and immune (week 10) serum samples were obtained for analyses. All animal protocols adhered to the established Institutional Animal Care and Use Committee guidelines.

Serum bactericidal antibodies in rabbits immunized with rLP2086 vaccine were determined using SBAs with human complement. Rabbit immune sera were heat-inactivated to remove intrinsic complement activity and subsequently serially diluted 1:2 in Dulbecco's PBS with Ca2+ and Mg2+ (D-PBS) in a 96-well microtiter plate to test for serum bactericidal activity against *N. meningitidis* strains. Bacteria used in the assay were grown in GC media supplemented with Kellogg's supplement (GCK) and monitored by optical density at 650 nm. Bacteria were harvested for use in the assay at a final $OD_{650}$ of 0.50-0.55, diluted in D-PBS and 1000-3000 CFU were added to the assay mixture with 20% human complement.

Human serum with no detectable bactericidal activity was used as the exogenous complement source. Complement sources were tested for suitability against each individual test strain. A complement source was used only if the number of bacteria surviving in controls without added immune sera was >75%. Ten unique complement sources were required to perform the SBAs described in this study.

After a 30 min incubation at 37° C. with 5% $CO_2$, D-PBS was added to the reaction mixture and aliquots transferred to microfilter plates filled with 50% GCK media. The microfilter plates were filtered, incubated overnight at 37° C. with 5% $CO_2$ and microcolonies were stained and quantified. The serum bactericidal titers were defined as the interpolated reciprocal serum dilution that yielded a 50% reduction in CFU compared to the CFU in control wells without immune sera. The SBA titer is defined as the reciprocal of the interpolated dilution of test serum that causes a 50% reduction in bacterial counts after a 30 min incubation at 37° C. Susceptibility to killing with P2086 immune sera was established if there was a 4-fold or greater rise in SBA titer for P2086 immune sera compared to the corresponding pre-immune sera. The limit of detection was a titer of 8 for the rabbit sera. Sera that were negative against the assay strain at the starting dilution were assigned a titer of one half the limit of detection for the assay (i.e. 4 for the rabbit).

Flow Cytometry

MnB cells were grown to an $OD_{650}$ of 0.45-0.55 and subsequently fixed in 1% (v/v) paraformaldehyde in 1×PBS for 10 min. One hundred microliters/well of bacteria were plated into 96-well U-bottom polystyrene plates, spun down and washed once in 1% (w/v) BSA in 1×PBS. Anti-LP2086 monoclonal antibodies were added to the bacterial pellets, resuspended and incubated on ice for 30 min. After two washes in 1% BSA/PBS, biotinylated goat anti-mouse IgG (subclasses 1+2a+2b+3) (Jackson Immunoresearch) was added to the cell pellets, resuspended and incubated on ice for 30 min. The cells were washed twice and resuspended in streptavidin—PE (BD Biosciences) and incubated on ice for 30 min. After two washes in 1% BSA/PBS, the cell pellets were resuspended in 1% paraformaldehyde. Mouse IgG was included as a negative control. Twenty thousand (20,000) events per well were acquired on a BD LSR II flow cytometer and analyzed using FlowJo v7 software (Treestar, Ashland, Oreg.). The mean fluorescence intensity (MFI) of the PE channel was determined for each sample after gating on bacterial cells in the logarithmic FSC versus SSC dot plot. An MFI was considered positive if the MFI was three times that of the control mouse IgG MFI.

Example 2

Polysorbate 80 Binding to rLP2086 Proteins

Figure 14:
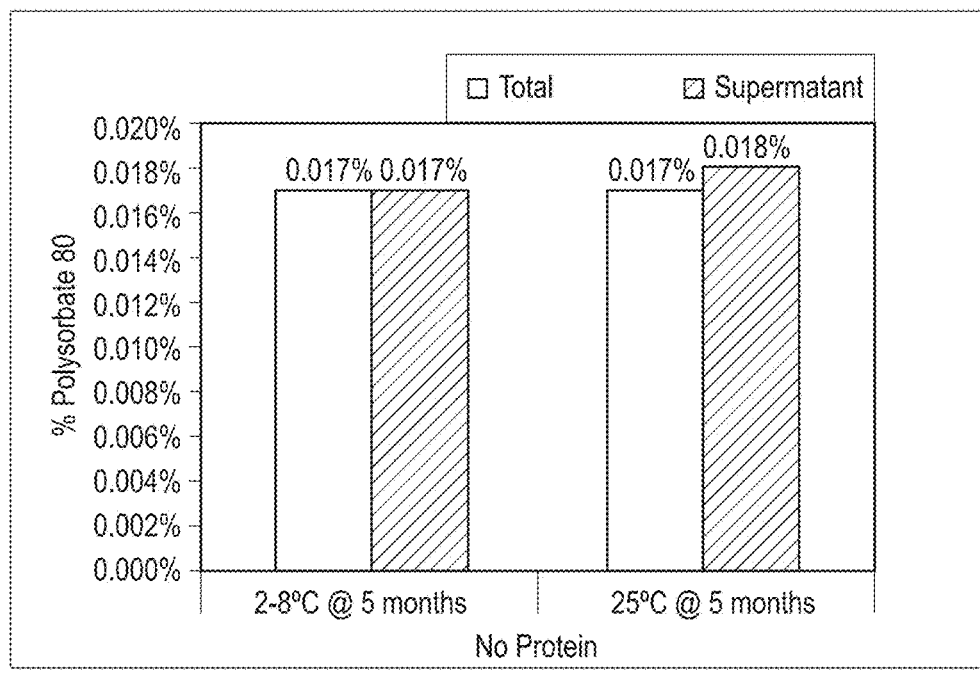
FIG. 14: Polysorbate 80 Results in rLP2086 Placebo with 0.5 mg/mL Aluminum
Figure 15:
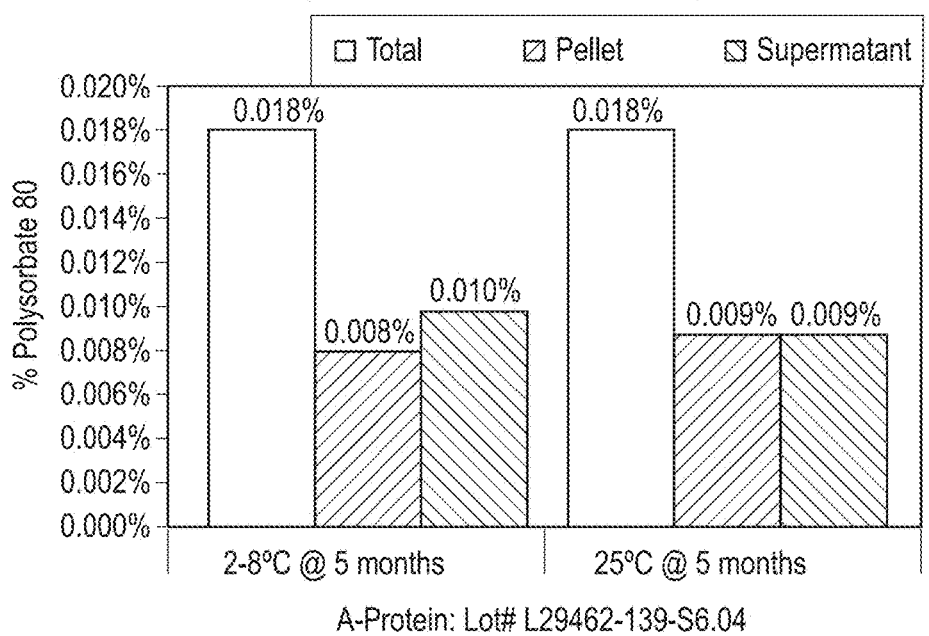
FIG. 15: Polysorbate 80 Results for Subfamily A
Figure 16:
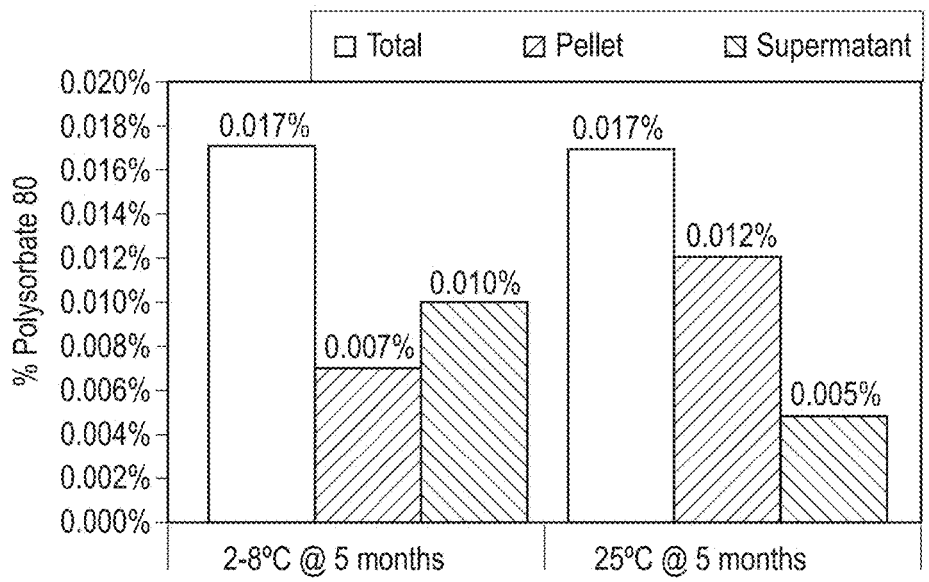
FIG. 16: Polysorbate 80 Results for Subfamily B
Figure 17:
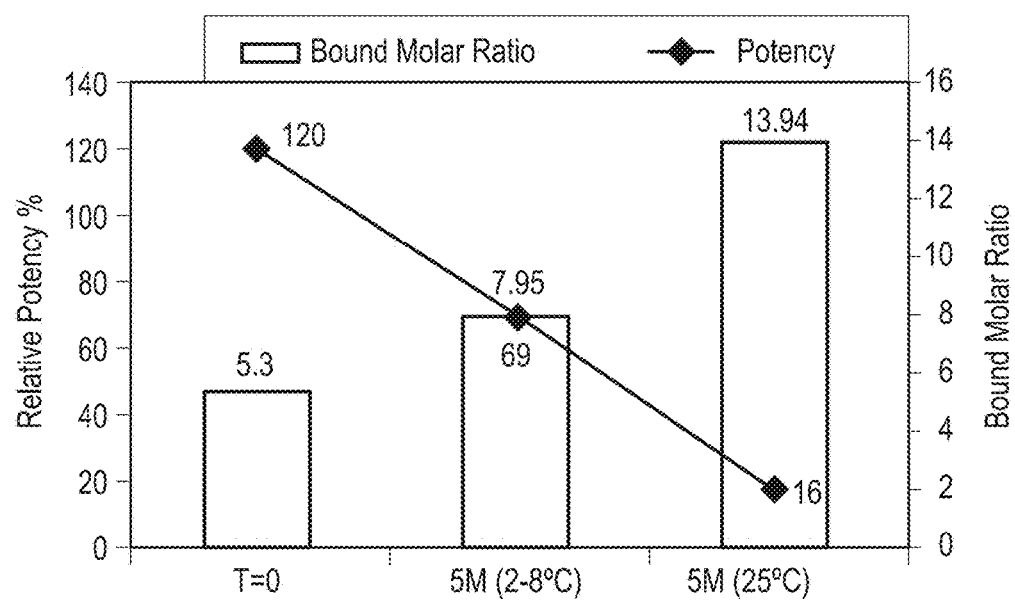
FIG. 17: Correlation of Potency and Bound Molar Ratio for Subfamily B

To understand the stability of Polysorbate 80 binding to each rLP2086 protein A and B, a rLP2086 formulated sample with 200 µg/mL Subfamily A with aluminum (Al) and another rLP2086 sample formulated with 200 µg/mL Subfamily B both stored at 2-8° C. and 25° C. were tested 5 months later for their protein and Polysorbate 80 content. A placebo (buffer+Al without protein) was also analyzed. The Polysorbate 80 distribution in the Placebo is shown in FIG. 14, while the Polysorbate 80 distributions for Subfamily A and B proteins are shown in FIG. 15 and FIG. 16, respectively. The Relative Potency (%) for Subfamily B was compared to the Bound Molar Ratio as shown in FIG. 17.

Results

As shown in FIG. 14, the total % Polysorbate 80 and the % Polysorbate 80 in the supernatant were the same (0.017%), which indicates that Polysorbate 80 did not bind to the aluminum or get trapped in the pellet. In addition, Polysorbate 80 was stable after 5 months at both 2-8° C. and 25° C.

The distribution of Polysorbate 80 in the bound (pellet), unbound (supernatant) and total of rLP2086 Subfamily A and Subfamily B samples are shown in FIG. 15 and FIG. 16, respectively. While the % Polysorbate 80 in the supernatant and pellet for Subfamily A at 2-8° C. and 25° C. at 5 months time point did not changed. More Polysorbate 80 was observed, however, in the pellet for Subfamily B sample at 25° C. at 5 months time point. Despite the different concentrations of Polysorbate 80 in the supernatant and pellet at 2-8° C. and 25° C., an accurate mass balance was achieved for both Subfamilies. As rLP2086 proteins bind 100% to aluminum phosphate at this matrix, Polysorbate 80 associated in the pellet was most likely bound to the protein molecules.

While both protein A and B bound to Polysorbate 80, protein A binding was the same for samples stored at 2-8° C. and 25° C., and protein B binding was almost double for samples stored at 25° C. compared to samples stored at 2-8° C. The Relative Potency for Subfamily B was determined at both 2-8° C. and 25° C. at $T_o$ and 5 months time points and was found to behave inversely to the Bound Molar Ratio as described in FIG. 17. The % Potency dropped from 120 at $T_0$ to 16% at 5M/25° C., while the Bound Molar Ratio increased from 5.3 to 13.9 in the same time period.

Example 3

Critical Molar Ratio Study

To determine the critical concentration of Polysorbate 80 required for rLP2086 stability, forty (40),LP2086 formulations were prepared containing Subfamily A only, Subfamily B only, and both Subfamily A and B at 200 µg/mL and 400 µg/mL with different Polysorbate 80 concentrations as described in Table 1. The total and bound proteins were determined for each sample as well as the % Polysorbate 80 in the total, supernatant and pellet at time zero ($T_0$), 14 days, and 1 Month at both 2-8° C. and 25° C. The results from this study are shown in FIG. 18 to FIG. 24.

TABLE 1

| Total Protein Antigen | Protein Subfamily | % Polysorbate 80 | | | | | |
|---|---|---|---|---|---|---|---|
| 0 | Placebo | 0.003 | X | 0.005 | X | X | X | 0.02 |
| 200 | A | X | 0.004 | 0.005 | 0.006 | 0.008 | 0.01 | 0.02 |
| 200 | B | 0.003 | 0.004 | 0.005 | 0.006 | 0.008 | 0.01 | 0.02 |
| 400 | A + B | X | X | X | 0.007 | X | 0.01 | 0.02 |
| 400 | A | X | X | X | 0.007 | X | 0.01 | 0.02 |
| 400 | B | X | X | X | 0.007 | X | 0.01 | 0.02 |

Results

Figure 18:
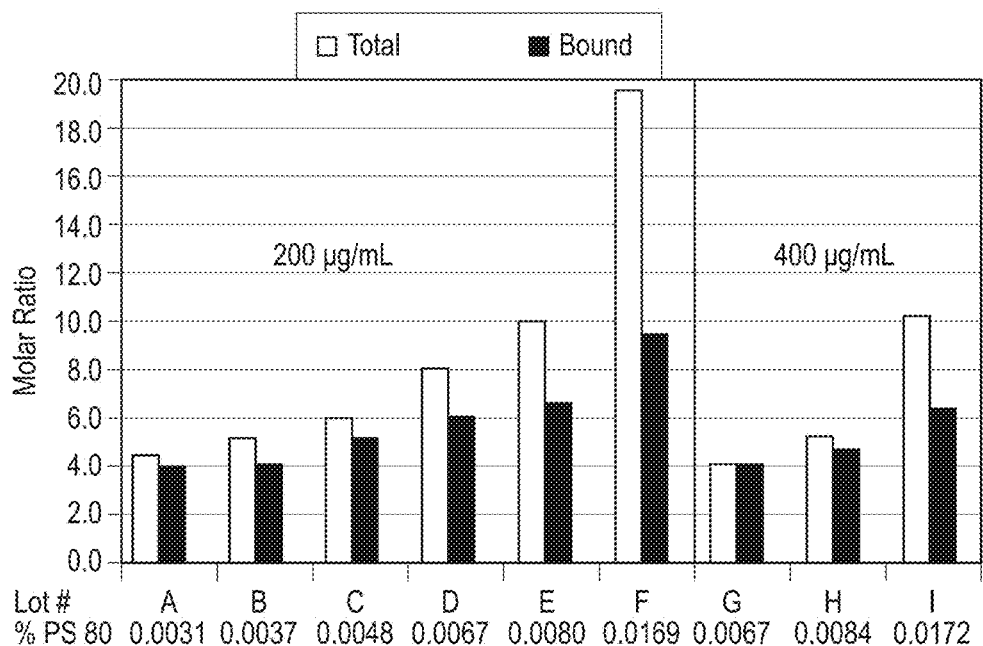
FIG. 18: Molar Ratio Results for Subfamily A

The Polysorbate 80 concentrations in the supernatant, pellet, and total were determined for all 40 rLP2086 formulation samples with aluminum phosphate. The Total and Bound Molar Ratios were determined for both Subfamily A and B and appear to be similar for both Subfamilies @ 200 µg/mL containing 0.005% Polysorbate 80 (5.4 Molar ratio) or less as shown in FIG. 18 and FIG. 19, respectively. The Total Molar Ratio for Subfamily B, however, was much higher than the Bound Molar Ratio for samples containing 0.0065% Polysorbate 80 (7.0 Molar ratio) or more. The data for Total and Bound Molar Ratios for Subfamily A, Subfamily B, and Subfamily A+B at 400 µg/mL each were also close for the formulations containing 0.008% Polysorbate 80 (8.6 Molar ratio) or less, however, the Total Molar Ratio was much higher than the Bound Molar Ratio for formulations containing 0.017% Polysorbate 80 (18.4 Molar ratio) as described in FIG. 20.

Example 4

Polysorbate 80 Binding Over Time

The percentage (%) Polysorbate 80 in the Supernatant and Pellet for Subfamily A and B formulation samples with AlPO4 was determined at $T_0$, 14 Days/25° C., 1 Month/4° C., and 1 Month/25° C. The % Polysorbate 80 in Supernatant for both Subfamily A and B formulation samples was relatively the same for samples stored at 2-8° C. The % Polysorbate 80 in the supernatant, however, decreased dramatically for samples stored at 25° C. even after only 14 days. The % Polysorbate 80 in Pellet for both Subfamily A and B were relatively similar at $T_0$/5° C. and 1 Month/5° C.

Figure 21:
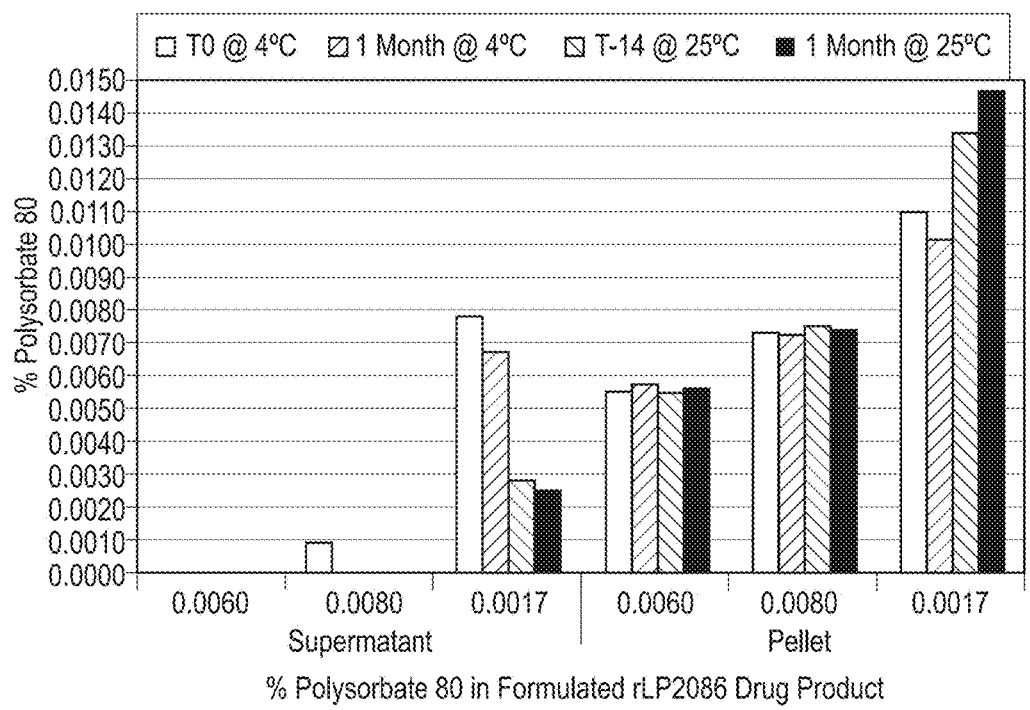
FIG. 21: Polysorbate 80 Results for rLP2086 Drug Product at Different Time Points
Figure 22:
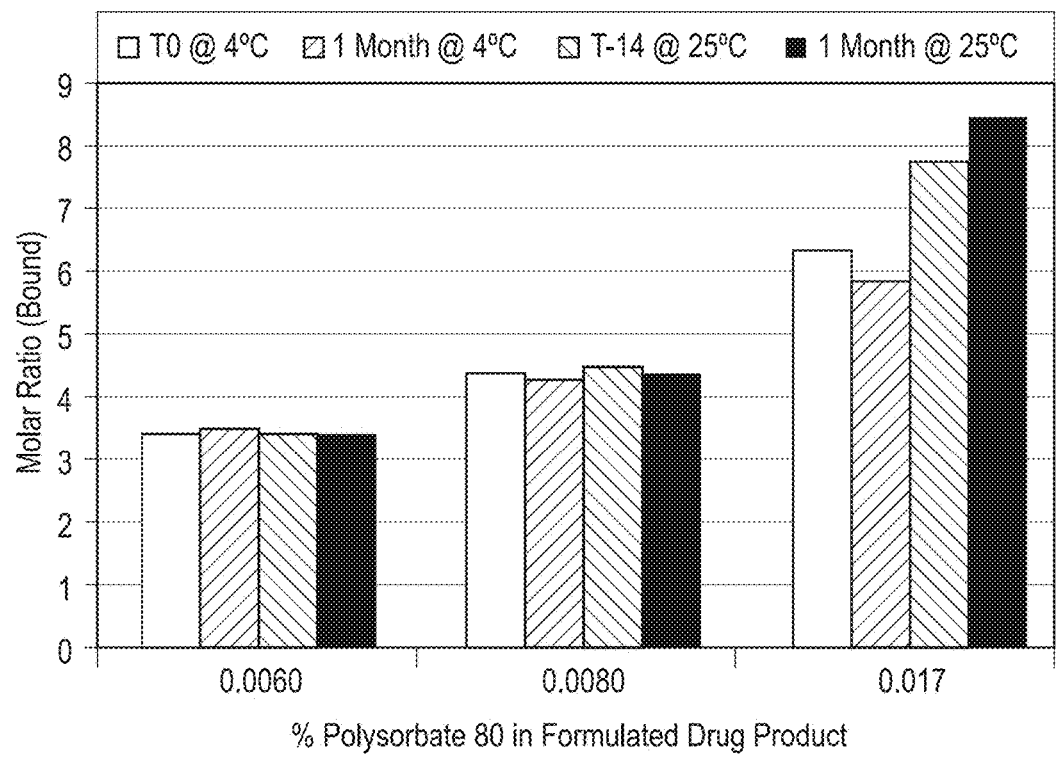
FIG. 22: Bound Molar Ratio Results for rLP2086 Drug Product at Different Time Points

C. The % Polysorbate in the supernatant, however, increased significantly for the samples stored at 25° C., especially for Subfamily B containing 0.008% Polysorbate 80 (8.6 Molar ratio) or higher. The % Polysorbate 80 was also determined in the Supernatant and Pellet for rLP2086 Subfamily A and B formulations with AlPO$_4$ at T$_0$, 14 Days/25° C., 1 Month/ 4° C., and 1 Month/25° C. As shown in FIG. 21, the Polysorbate 80 concentrations for samples containing 0.008% were approximately the same for all 4 time points. The Polysorbate 80 concentrations, however, increased for the sample containing 0.017% Polysorbate 80 stored at 25° C. No Polysorbate 80 was found in the supernatant of samples containing 0.008% Polysorbate 80 or less. As shown in FIG. 22, the Bound Molar Ratio was stable for samples containing 0.008% Polysorbate 80 or less at all 4 time points. The Bound Molar Ratio, however, increased for the sample containing 0.017% Polysorbate 80 stored at 25° C.

The Potency for Subfamily A and B formulation samples with AlPO$_4$ was determined at T$_0$ and 14 Days/25° C. (FIG. 23 and FIG. 25, respectively). As described in FIG. 23, the Potency for Subfamily A at different total molar ratios ranged from 91 to 102 at both 5° C. and 25° C. While the Bound Molar Ratio results were also relatively the same at either temperature, a slight increase in the Potency was seen as the total/Bound Molar Ratio increased.

The Potency for Subfamily B for the 5° C. samples was about 95% for total molar ratios up to 9.0. The Subfamily B potency, however, decreased to 79% as the total molar ratio increased to 18.1. Further, the sample with Total molar ratio at 18.1 had higher bound molar ratio compared to the other sample. At 25° C., the Subfamily B Potency exhibited a significant drop from 83% to 5% as the total molar ratio increased from 5.3 to 18.1. The bound molar ratio values for the 25° C. samples increased from 5.3 to 13.8 as the total molar ratio increased. Thus, the Potency for Subfamily B is inversely proportional to the Bound Molar Ratio.

Both Subfamily A and Subfamily B proteins bound to Polysorbate 80. Subfamily A binding was the same for samples stored at 2-8° C. and 25° C., but Subfamily B binding was almost double for samples stored at 25° C. Further, the Critical Molar Ratio Study indicated that the 200 µg/mL formulation samples were stable when containing 0.008% Polysorbate 80 or less, which is equivalent to a Total Molar Ratio of 4.2 or less.

Example 5

Detergent Concentration and rLP2086 Subfamily B Antigen Potency

Additional stability studies with varying concentrations of Polysorbate 80 corroborated the criticality of the molar ratio of Polysorbate 80 to protein for maintaining potency. In one experiment, the immunogenic composition was formulated at the 200 µg dosage (total protein concentration 400 µg/mL) at pH 6.3 in 10 mM histidine buffered saline (HBS) with 0.5 mg/mL aluminum (as aluminum phosphate) and spiked with 0.01%, 0.02%, 0.05% or 0.1% Polysorbate 80 (corresponding molar ratio of Polysorbate 80 to rLP2086 protein at 5.3, 10.7, 26.7 and 53.4). The formulated samples were incubated at 25° C. and control samples were stored at 2-8° C. There was no significant change in potency at time "0" at Polysorbate 80 concentrations up to 0.1%. For longer periods at 2-8° C. and 25° C., however, a reduction in potency was observed as a function of temperature and Polysorbate 80 concentration. As the concentration of Polysorbate 80 was increased from 0.01% to 0.1% in the immunogenic composition, the 3-month stability point demonstrated a reduction in potency of the Subfamily B protein to less than 10% and 25% at 25° C. and 2-8° C., respectively (FIG. 1).

An additional stability study (FIG. 2) was performed evaluating the Subfamily B protein at a concentration of 4 mg/mL in HBS and spiked with Polysorbate 80 to a final concentration of 0.06, 0.5 and 1% (corresponding molar ratios of 3.3, 26.7 and 53.4). The control contained 0.09% Polysorbate 80. The Subfamily B protein in 0.06% Polysorbate 80 (molar ratio of 3.3) was stable. The same samples containing increased concentration of Polysorbate 80 to 0.5% and 1% (molar ratios 26.7 and 53.4 respectively) were unstable. For 400 µg/mL immunogenic composition formulations, instability of Subfamily B protein was noted in all formulations containing 0.01% Polysorbate 80 concentration (5.3 molar ratio) or higher. At 4 mg/mL protein and 0.06% Polysorbate 80 concentrations, however, there was no reduction in potency because the ratio of Polysorbate 80 to protein (3.3) is lower than that at 400 µg/mL protein plus 0.01% Polysorbate 80 concentrations (molar ratio 5.3). The reduction in potency of Subfamily B protein by Polysorbate 80 is thus correlated to the molar ratio of the Polysorbate 80 detergent to protein and not to the absolute concentration of Polysorbate 80 in the matrix.

Accordingly, Polysorbate 80 concentration must be reduced in the immunogenic composition in order to maintain the stability of the Subfamily B protein in the vaccine and during subsequent storage at 2-8° C. An accelerated 28-day stability study was designed for the immunogenic composition with varying molar ratios of Polysorbate 80 (0, 1.1, 2.7 and 5.3) at 20 and 200 µg dosages (FIG. 3 and FIG. 4). A bivalent (Subfamily A and Subfamily B) formulation was prepared in 10 mM histidine buffered saline pH 6.0, 0.5 mg/mL aluminum as aluminum phosphate with various Polysorbate 80 concentrations. Samples were incubated at 25° C. along with a 2-8° C. control group. Samples were analyzed for potency at 0, 7, 14 and 28 days. Both Subfamily A (data not shown) and B proteins were stable for all groups containing less than a 5.3 molar ratio of Polysorbate 80 to protein. A potency value of greater than 80% is considered to be within the assay variability. At the 5.3 molar ratio, a decreasing trend for the Subfamily B protein potency was observed for 25° C. samples.

A comprehensive study evaluated all the potential clinical dosages (20, 60, 120 and 200 µg dosage) formulated with varying Polysorbate 80-to-protein molar ratios under accelerated storage stability conditions to investigate the effects of Polysorbate 80-to-protein molar ratios on the stability of MnB rLP2086 proteins. Bivalent MnB rLP2086 immunogenic compositions formulated at Polysorbate 80-to-protein molar ratios ranging from approximately 1.4 to 10.7 were used. To generate immunogenic compositions formulated at increasing Polysorbate 80-to-protein molar ratios (1.4, 2.4, 3.4, 3.9, 4.3, 4.7 and 10.7), antigens were adjusted to variable molar ratios by adding Polysorbate 80 such that during immunogenic composition formulation, additional Polysorbate 80 was not needed. There were two sets of antigen lots used in this study. One set of Subfamily A and B lots were generated with a Polysorbate 80-to-protein molar ratio of 1.4 and the other set at 2.4. The set of proteins with a molar ratio of 2.4 was used to adjust the molar ratios of 3.4, 3.9, 4.3, and 10.7 by spiking with additional Polysorbate 80. The final matrix of immunogenic composition was 10 mM histidine, 150 mM NaCl, pH 6.0, 0.5 mg/mL aluminum phosphate with the Polysorbate 80-to-protein molar ratios mentioned above. After storage at 2-8° C. or 25°

C. for specific intervals, gentle mixing was applied with a rocker 24 hours prior to testing. Total protein by IEX-HPLC, potency, appearance, optical density at 320 nm of the supernatant fraction and pH were tested.

Figure 6:
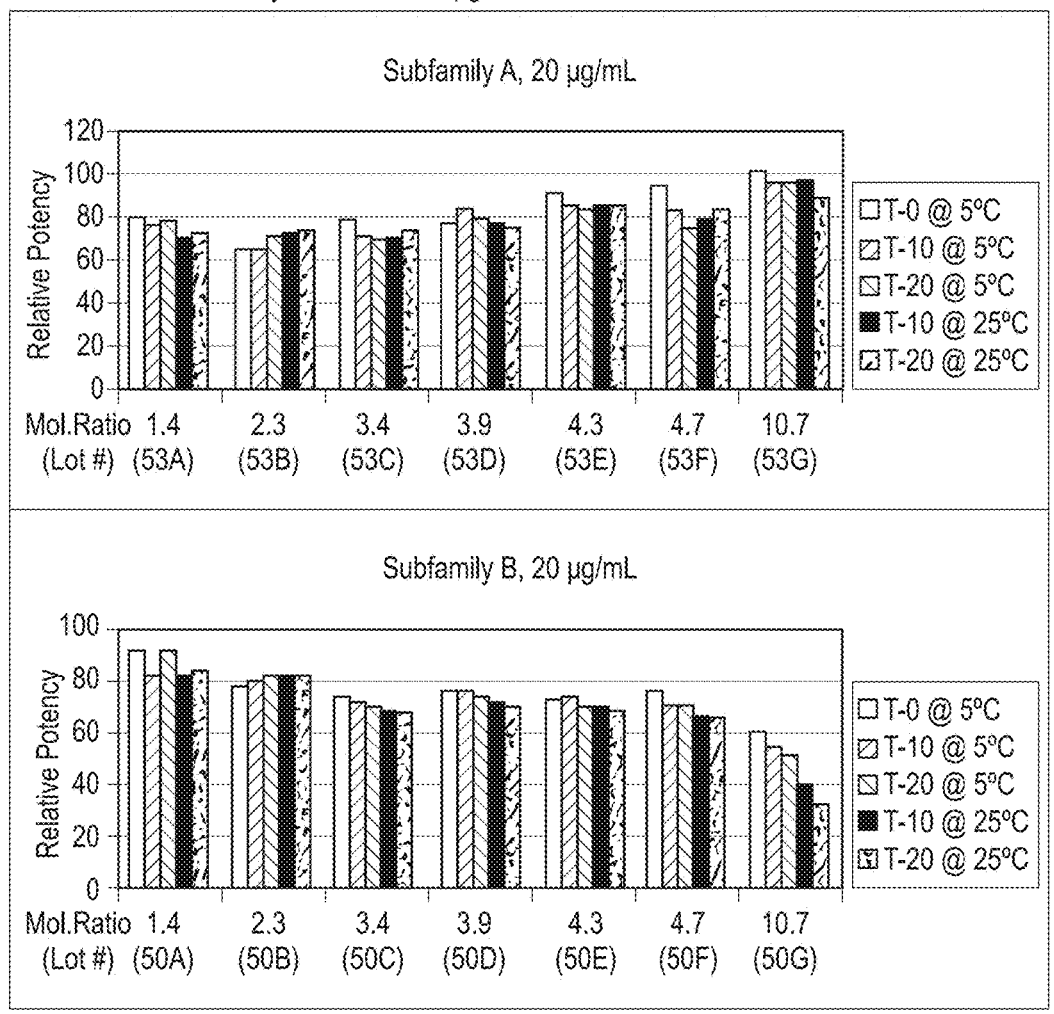
FIG. 6: Potency Results for 20 µg/mL with Different Molar Ratios

Potency results of 200 and 20 µg doses are shown in FIG. 5 and FIG. 6, respectively. The potency assay was more sensitive than other tests used in the study. Overall, there was no significant reduction in potency observed either for Subfamily A or B antigens as compared to the initial time point for all dosages with molar ratios of 4.3 and lower. Formulations with a molar ratio of 4.7 were considered at marginal due to a slight reduction in potency for Subfamily B proteins stored at 25° C. The potency results for Subfamily B antigen for formulations at a molar ratio of 10.7 were significantly lower for samples stored at 25° C. than those stored at 2-8° C.

Example 6

Aluminum Concentration and rLP2086 Subfamily A and B Antigen Potency

Figure 7:
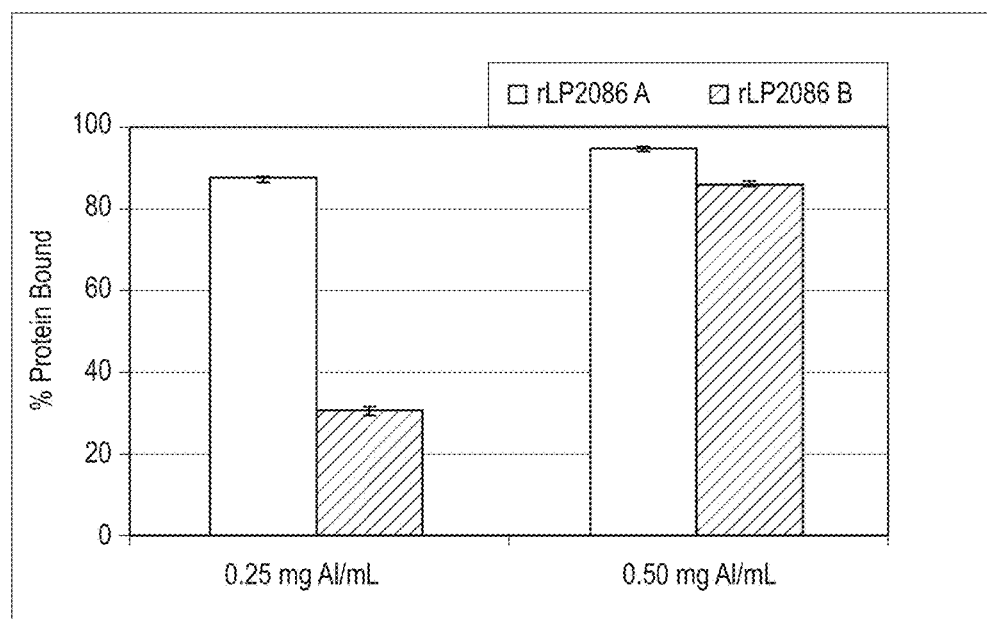
FIG. 7: Protein Binding to Aluminum Phosphate at pH 6.5

A number of experiments were conducted to determine the optimal level of aluminum phosphate to ensure greater than 95% binding of both Subfamily A and B proteins. Initial studies focused on optimization of the formulation at pH 6.5. Formulations were prepared with a target dosage of 200 µg/mL of each protein from Subfamily A and B proteins in 10 mM histidine buffer at pH 6.5 with 0.02% Polysorbate 80 and either 0.25 or 0.5 mg/mL aluminum (as aluminum phosphate). Subfamily B protein bound to aluminum phosphate to a lesser extent than did Subfamily A protein (FIG. 7). Increasing the aluminum content from 0.25 mg/mL to 0.5 mg/mL increased binding of Subfamily B protein to >80%. Since the binding mechanism between protein and aluminum suspension is mostly an ionic interaction, the pH of the suspension is a factor that influences binding.

Figure 8:
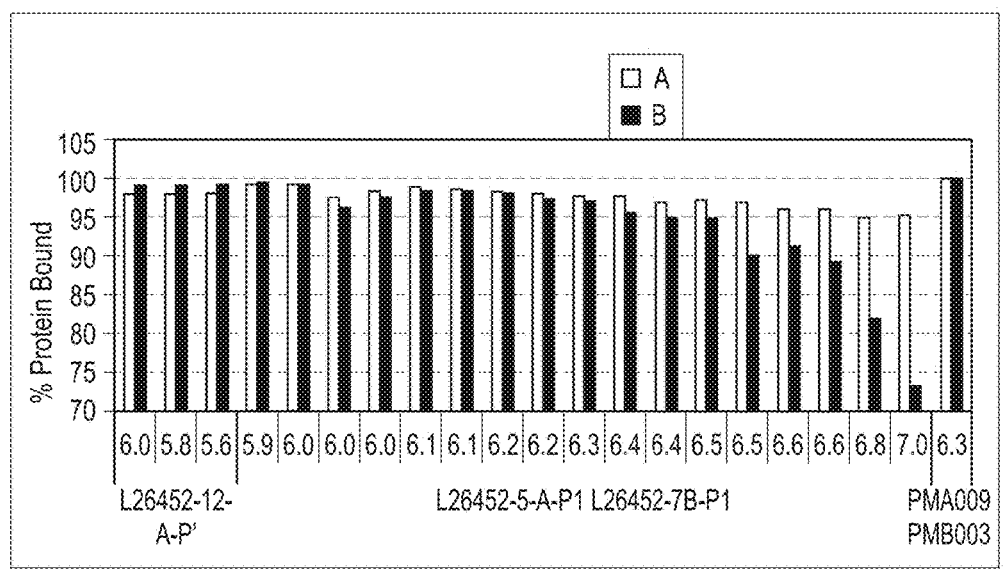
FIG. 8: Binding of MnB rLP2086 Subfamily A and B as a Function of pH.

The formulation pH was optimized to ensure greater than 90-95% binding of the Subfamily B protein. Multiple formulations at 200 µg/mL of each A and B proteins with pH ranging from 5.6 through 6.5 with different lots of immunogenic compositions were examined (FIG. 8). Greater than 90-95% binding of both proteins occurred at formulations with pH ranging from 5.6 to 6.4. As the pH of the formulations increased to 6.5 and above, the binding of Subfamily B protein was significantly reduced. The recommended target pH is 6.0 to ensure greater than 90% binding of both Subfamily A and B proteins.

The robustness of the formulation under formulation variables and/or limits by varying the pH, buffer, protein, and Polysorbate 80 concentrations was also evaluated (FIG. 9). While the binding of Subfamily A protein was consistently high (≥95%) with total protein concentration up to 500 µg/mL (250 µg/mL each protein), Subfamily B protein binding was more sensitive to protein concentration and pH. As commercial formulations at a 200 µg dosage are used, the results from this experiment further supported the recommended formulation at a pH of 6.0 with 0.5 mg/mL aluminum phosphate.

Formulations with and without aluminum phosphate were evaluated to investigate the feasibility of providing a stable formulation without aluminum phosphate at concentrations of Polysorbate 80 low enough for Subfamily B protein stability. Immunogenic compositions were formulated at 20 and 200 µg dosages in histidine buffered saline buffer with Polysorbate 80 concentration ranging from 0 to 5.3 molar ratios. Half of the samples were subjected to agitation with a digital multi-tube vortexer set at 500 rpm under pulse mode (2 seconds on and one second off) for 24 hours prior to testing. This condition was adopted to simulate the ISTA tests (International Safe Transit Association) typically performed at the final immunogenic composition shipping package stage to mimic extreme vibrations during shipping conditions.

Figure 11:
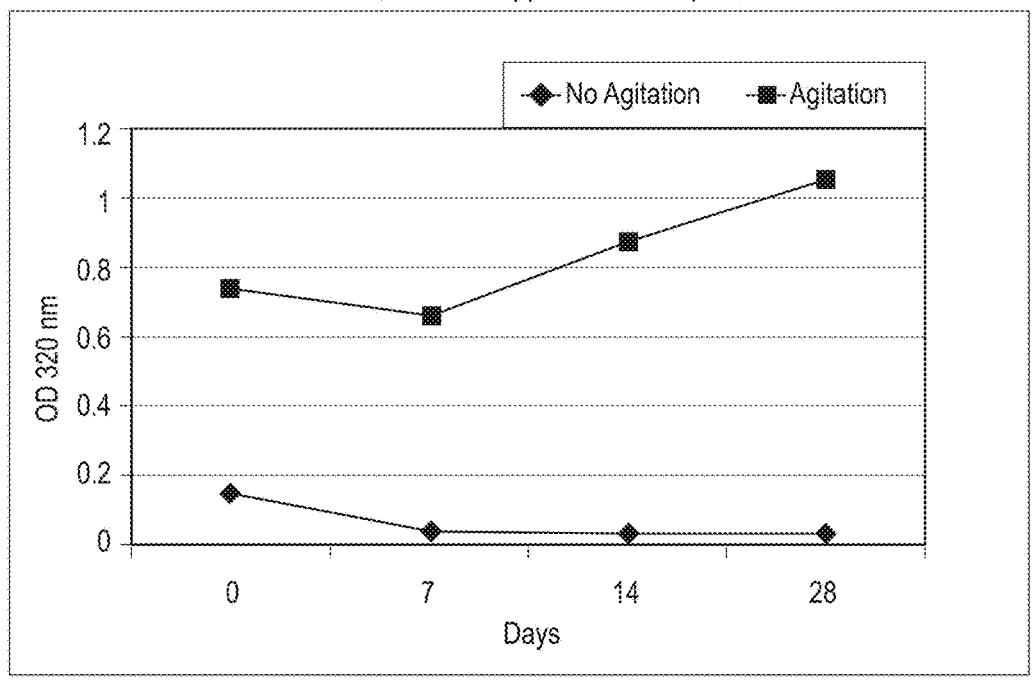
FIG. 11: OD Measurements of Appearance Samples, 2-8° C.

With agitation, formulations without aluminum phosphate precipitated which eventually led to potency loss of both Subfamily A and B antigens. An appearance test (FIG. 10) and absorbance measurements at k=320 nm (FIG. 11) demonstrated the formation of aggregates and/or precipitates when formulations without aluminum phosphate were agitated. Potency testing of these samples (FIG. 12 and FIG. 13) demonstrated significant loss of potency for both Subfamily A and B proteins at all time points tested. The loss of potency was most pronounced in formulations containing low amounts of Polysorbate 80. Since low amounts of Polysorbate 80 are necessary to maintain Subfamily B protein stabilization, the inclusion of aluminum phosphate in the formulation is required to preserve stability. rLP2086 immunogenic compositions may be formulated with aluminum phosphate, which will function to enhance potency stability as measured by the in vitro potency assay.

Example 7

Succinate and Histidine as Buffers

A series of formulations were prepared to compare binding of rLP2086 Subfamily A and B proteins in succinate and histidine, as well as effects of pH, Polysorbate 80, and $MgCl_2$ on binding (Table 2). The robustness of the formulation under formulation variables and or limits by varying the pH, buffer, protein, and polysorbate concentrations was evaluated (FIGS. 25 and 26). The binding of aluminum to Subfamily A and Subfamily B protein was similar regardless of the buffer (histidine or succinate) used.

TABLE 2

Formulations to Evaluate Histidine and Succinate buffers, $MgCl_2$, Polysorbate 80, and pH 5.6-6.0 on Binding of rLP2086 with $AlPO_4$[1]

| rLP2086 A (µg/mL) | rLP2086 B (µg/mL) | Histidine (mM) | Succinate (mM) | PS 80 (%) | Saline (%) | $MgCl_2$ (mM) | Target pH |
|---|---|---|---|---|---|---|---|
| 200 | 200 | 0 | 5 | 0.020 | 0.9 | 0 | 6.0 |
| 200 | 200 | 0 | 5 | 0.020 | 0.9 | 0 | 5.8 |
| 200 | 200 | 0 | 5 | 0.020 | 0.9 | 0 | 5.6 |
| 200 | 200 | 0 | 5 | 0.010 | 0.9 | 0 | 6.0 |
| 200 | 200 | 0 | 5 | 0.005 | 0.9 | 0 | 6.0 |
| 250 | 250 | 0 | 5 | 0.020 | 0.9 | 0 | 6.0 |
| 250 | 250 | 0 | 5 | 0.020 | 0.9 | 0 | 5.8 |
| 250 | 250 | 0 | 5 | 0.020 | 0.9 | 0 | 5.6 |
| 200 | 200 | 0 | 10 | 0.020 | 0.9 | 0 | 6.0 |
| 200 | 200 | 0 | 20 | 0.020 | 0.9 | 0 | 6.0 |
| 200 | 200 | 0 | 5 | 0.020 | 0.9 | 10 | 6.0 |
| 200 | 200 | 10 | 0 | 0.020 | 0.9 | 0 | 6.0 |
| 200 | 200 | 10 | 0 | 0.020 | 0.9 | 0 | 5.8 |
| 200 | 200 | 10 | 0 | 0.020 | 0.9 | 0 | 5.6 |
| 200 | 200 | 10 | 0 | 0.010 | 0.9 | 0 | 6.0 |
| 200 | 200 | 10 | 0 | 0.005 | 0.9 | 0 | 6.0 |
| 250 | 250 | 10 | 0 | 0.020 | 0.9 | 0 | 6.0 |
| 250 | 250 | 10 | 0 | 0.020 | 0.9 | 0 | 5.8 |
| 250 | 250 | 10 | 0 | 0.020 | 0.9 | 0 | 5.6 |
| 200 | 200 | 5 | 0 | 0.020 | 0.9 | 0 | 6.0 |
| 200 | 200 | 20 | 0 | 0.020 | 0.9 | 0 | 6.0 |
| 200 | 200 | 10 | 0 | 0.020 | 0.9 | 10 | 6.0 |

[1]All formulations described in Table 2 contain 0.5 mg Al/mL.

The effect of buffer salt and mixing time on aluminum binding were evaluated with three commonly used buffer salts, chosen because their pKa's are in the physiologic range and because these salts are generally regarded as safe. rLP2086 Subfamily A and B proteins were formulated with one of the three buffer salts: 5 mM succinate, 10 mM histidine, or 10 mM phosphate at a pH suitable for the pKa of each salt to determine the extent of binding at each condition. The time required for binding to reach completion was evaluated by allowing the samples to mix for either 5 or 120 min before measuring the amount of protein bound.

Figure 27:
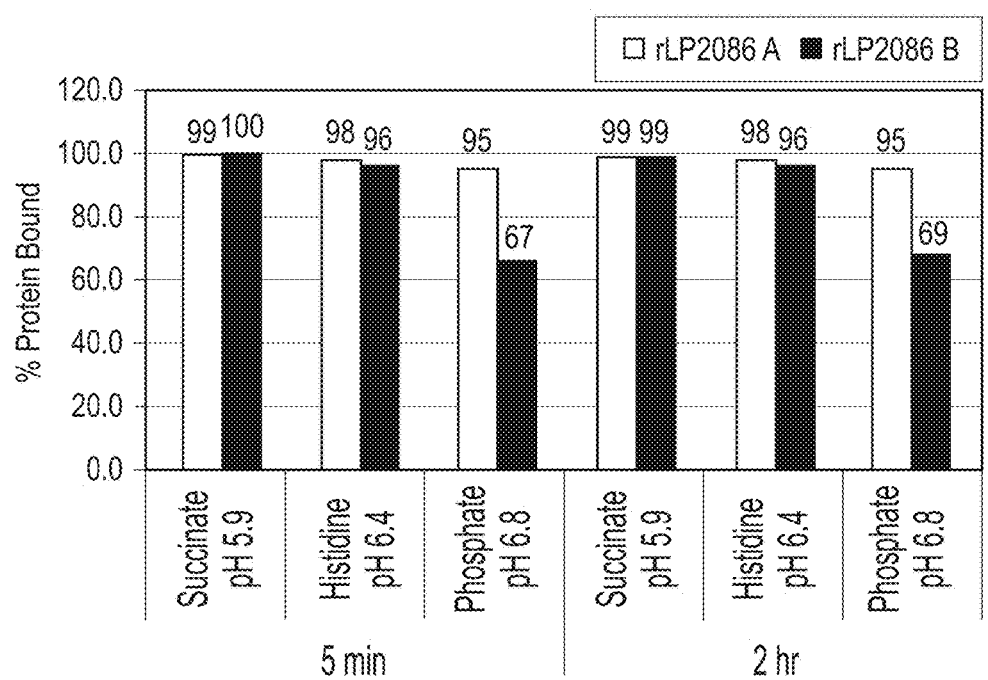
FIG. 27: Comparison of Binding in Succinate, Histidine, and Phosphate buffer

As shown in FIG. 27, Subfamily B protein exhibited reduced binding at pH 6.8 in phosphate buffer, while Subfamily A protein was not significantly affected at the same conditions. The amount of protein bound to aluminum was similar in samples formulated with histidine or succinate. Thus, these two buffer salts were chosen for further evaluation. While not wishing to be bound by theory, it is possible that the reduced binding in phosphate buffer results from competition for binding sites on AlPO4 with the added phosphate ions.

At these conditions and concentrations of protein and AlPO4, binding was complete after 5 min of mixing at room temperature as similar results were obtained after mixing for 2 hours.

To further examine whether the reduced binding of Subfamily B protein in phosphate buffer at pH 6.8 was due to pH or differences between buffer salts, binding was measured over a pH range of 5.3 to 7.0 in either histidine- or succinate-buffered formulations. Bivalent formulations were prepared containing 0.2 mg/mL of each subfamily protein (0.4 mg/mL total protein), 0.02% PS80, 0.5 mg Al/mL, and 150 mM NaCl. Samples were formulated in either 10 mM histidine or 5 mM succinate to compare the effect of buffer salt. After formulation, the pH of each sample was individually verified.

The binding profile from pH 5.3 to 7.0 is shown for Subfamily A protein in FIG. 28 and for Subfamily B protein in FIG. 28. Subfamily A protein exhibited little change in the amount of protein bound, with binding remaining above 95% across the pH range tested. A formulation containing histidine with a target pH 7.0 resulted in a pH of 6.8. The pH was not adjusted to 7.0 (e.g. by addition of base) to avoid possible effects on the protein or AlPO4 and results for this datapoint are therefore not available.

The binding profile of Subfamily B protein (shown in FIG. 29) exhibited a pH-dependent trend. Whether binding was performed in histidine or succinate buffered formulations, however, the amount of protein bound to aluminum was similar. Binding was dependent on the pH of the formulation rather than the buffering salt. Binding remained at 95% up to pH 6.5 (94% in histidine, 95% in succinate), but decreased when pH was greater than 6.5. At pH 7.0, binding decreased to about 82%, with minor differences between buffering salts.

To obtain robust binding of Subfamily B protein with AlPO4 at these concentrations, a pH of 6.5 or less is preferred.

Example 8

Safety, Tolerability And Immunogenecity Study

A study is conducted to assess the safety, tolerability, and immunogenicity of rLP2086 vaccine administered in a healthy adolescent population, according to regimens of either 0 and 2 months; 0, 2, and 6 months; 0 and 2 months followed by a 12-month booster dose.

The immunogenic composition is a rLP2086 vaccine (recombinant lipidated). The immunogenic composition includes a *N. meningitidis* serogroup B recombinant ORF2086 protein that was expressed in *Escherichia coli* and formulated in a bivalent vaccine composed of one subfamily A strain and one subfamily B strain of rLP2086. In particular, the immunogenic composition is a 0.5 mL dose formulated to contain 60 μg, 120 μg, or 200 μg each of a purified subfamily A and a purified subfamily B rLP2086 protein, a 2.8 molar ratio of polysorbate 80, and 0.25 mg of $Al^{3+}$ as AlPO4, 10 mM histidine-buffered saline at pH 6.0. A control composition includes a normal saline solution (0.9% sodium chloride) in a 0.5 mL dose.

Subjects are randomly assigned to 5 groups. See Table 3. The subjects are stratified into two age groups, ≥11 to <14 and ≥14 to <19 years of age.

TABLE 3

Study Design

| | Vaccination 1 | Vaccination 2 | Post-Vaccination 2 Blood draw | Vaccination 3 | Post-Vaccination 3 Blood draw | Vaccination 4 | Post-Vaccination 4 Blood Draw |
|---|---|---|---|---|---|---|---|
| Visit number | 1 | 2 | 3 | 4 | 5 | 6 | 7 |
| Approximate month | 0 | 2 | 3 | 6 | 7 | 12 | 13 |
| Group 1 | rLP2086 | rLP2086 | | Saline | | Saline | |
| Group 2 | rLP2086 | rLP2086 | | rLP2086 | | Saline | |
| Group 3 | rLP2086 | rLP2086 | | Saline | | rLP2086 | |
| Group 4 | rLP2086 | Saline | | rLP2086 | | Saline | |
| Group 5 | Saline | Saline | | rLP2086 | | rLP2086 | |
| Blood Draw | 20 mL | | 20 mL | | 20 mL | 20 mL | 20 mL |

Saline is used as a placebo because there is no proven safe, immunogenic, and effective vaccine against MnB that could serve as an active control.

Subjects receive one dose of rLP2086 vaccine or saline at each of the vaccination visits (e.g., visits 1, 2, 4, and 6) according to Table 3. Standard vaccination practices are observed and the vaccine is not injected into blood vessels. The rLP2086 vaccine is administered intramuscularly by injecting 0.5 mL into the upper deltoid muscle. Saline is administered intramuscularly into the upper deltoid muscle.

A. Visit 1

On Visit 1, day 1, vaccination 1, the subject first has blood drawn and then receives a vaccination. The visit 1 blood draw and vaccination 1 occurs on the same day. Before vaccination, a blood sample (approximately 20 mL) from the subject is collected. For subjects randomized to group 1, 2, 3, and 4, a single 0.5-mL intramuscular injection of rLP2086 vaccine is administered into the upper deltoid muscle. For subjects in group 5, a single 0.5-mL intramuscular injection of saline is administered into the upper deltoid muscle.

B. Visit 2 (42 to 70 days after Visit 1), Vaccination 2

For groups 1, 2, and 3, a single 0.5-mL intramuscular injection of rLP2086 vaccine is administered into the upper deltoid muscle. For groups 4 and 5, a single 0.5-mL intramuscular injection of saline is administered into the upper deltoid muscle.

C. Visit 3 (28 to 42 days after Visit 2), Post vaccination 2 Blood Draw

A blood sample (approximately 20 mL) from the subject is collected.

D. Visit 4 (105 to 126 days after Visit 2), Vaccination 3

For groups 2, 4, and 5, a single 0.5-mL intramuscular injection of rLP2086 vaccine is administered into the upper deltoid muscle. For groups 1 and 3, a single 0.5-mL intramuscular injection of saline is administered into the upper deltoid muscle.

E. Visit 5 (28 to 42 days after Visit 4), Post vaccination 3 Blood Draw

A blood sample (approximately 20 mL) from the subject is collected.

F. Visit 6 (161 to 175 days after Visit 4), Vaccination 4

At visit 6, the subject first has blood drawn and then receives a vaccination. The visit 6 blood draw and vaccination 4 occurs on the same day. Before vaccination, a blood sample (approximately 20 mL) from the subject is collected. For groups 3 and 5, a single 0.5-mL intramuscular injection of rLP2086 vaccine is administered into the upper deltoid muscle. For subjects in groups 1, 2, and 4, a single 0.5-mL intramuscular injection of saline is administered into the upper deltoid muscle.

G. Visit 7 (28 to 42 days after Visit 6), Post vaccination 4 Blood Draw

A blood sample (approximately 20 mL) from the subject is collected.

Immunogenicity Results

The primary objective of this study was to assess the immunogenicity of 60 μg, 120 μg, and 200 μg rLP2086 vaccine as measured by SBA performed with MnB strains expressing LP2086 subfamily A and B proteins.

The secondary objective of this study was to assess the immunogenicity of 60 μg, 120 μg, and 200 μg rLP2086 vaccine as determined by quantitation of Ig binding to rLP2086 vaccine subfamily A and B proteins.

SBA activity was assessed using 3 subfamily A and 3 subfamily B strains as shown in Table 4.

TABLE 4

Analysis of Subjects Achieving SBA Titer of Fold Rise ≥ 4 From Predose 1 - mITT Population (Study 6108A1-2001-WW/B1971005)

| Strain | Randomized Vaccine Group | $N^a$ | $n^b$ (%) | (95% $CI^c$) | p-Value$^d$ |
|---|---|---|---|---|---|
| 1-month postdose 2 | | | | | |
| Subfamily A Strain 1 | Control | 80 | 1 (1.3) | (0.0, 6.8) | >0.9999 |
| | 60 μg rLP2086 Vaccine | 18 | 16 (88.9) | (65.3, 98.6) | 0.0007 |
| | 120 μg rLP2086 Vaccine | 115 | 96 (83.5) | (75.4, 89.7) | <0.0001 |
| | 200 μg rLP2086 Vaccine | 106 | 93 (87.7) | (79.9, 93.3) | <0.0001 |
| Subfamily B Strain 1 | Control | 84 | 0 (0.0) | (0.0, 4.3) | >0.9999 |
| | 60 μg rLP2086 Vaccine | 21 | 15 (71.4) | (47.8, 88.7) | 0.0392 |
| | 120 μg rLP2086 Vaccine | 121 | 72 (59.5) | (50.2, 68.3) | 0.0225 |
| | 200 μg rLP2086 Vaccine | 114 | 68 (59.6) | (50.1, 68.7) | 0.0244 |
| 1-month postdose 3 | | | | | |
| Subfamily A Strain 1 | Control | 73 | 4 (5.5) | (1.5, 13.4) | >0.9999 |
| | 60 μg rLP2086 Vaccine | 19 | 17 (89.5) | (66.9, 98.7) | 0.0004 |
| | 120 μg rLP2086 Vaccine | 111 | 103 (92.8) | (86.3, 96.8) | <0.0001 |
| | 200 μg rLP2086 Vaccine | 100 | 94 (94.0) | (87.4, 97.8) | <0.0001 |
| Subfamily B Strain 1 | Control | 79 | 1 (1.3) | (0.0, 6.9) | >0.9999 |
| | 60 μg rLP2086 Vaccine | 21 | 17 (81.0) | (58.1, 94.6) | 0.0036 |
| | 120 μg rLP2086 Vaccine | 112 | 97 (86.6) | (78.9, 92.3) | <0.0001 |
| | 200 μg rLP2086 Vaccine | 105 | 89 (84.8) | (76.4, 91.0) | <0.0001 |

Abbreviation: CI = confidence interval; SBA = serum bactericidal assay.

Note:

The assay validation supports a lower limit of quantitation (LLOQ) of Subfamily A strain 1 = 9 and Subfamily B Strain 1 = 10. SBA titers above the LLOQ are considered accurate and their quantitated values will be reported. Values below the LLOQ or denoted as below LLOQ will be set to 0.5*LLOQ for analysis.

The proportions of subjects with titers achieving a defined level are presented in Table 5. For both subfamilies, the proportions of subjects achieving defined SBA titer levels were greater at postdose 3 than at postdose 2.

TABLE 5

Subjects Achieving Defined SBA Titer Levels in Stage 1 - mITT Population (Study 6108A1-2001-WW/B1971005)

| | | | Vaccine Group (as Randomized) | | | | | | | | | | | | | | | |
|---|---|---|---|---|---|---|---|---|---|---|---|---|---|---|---|---|---|---|
| | | | Control | | | | rLP2086 Vaccine | | | | | | | | | | | |
| | Sampling | | | | | | 60 µg | | | | 120 µg | | | | 200 µg | | | |
| Strain | Time Point | SBA Titer | $N^a$ | $n^b$ | % | (95% $CI^c$) | $N^a$ | $n^b$ | % | (95% $CI^c$) | $N^a$ | $n^b$ | % | (95% $CI^c$) | $N^a$ | $n^b$ | % | (95% $CI^c$) |
| Subfamily A Strain 2 | Predose 1 | 32 | 64 | 7 | 10.9 | (5.3, 21.2) | 15 | 0 | 0.0 | (0.2, 35.8) | 90 | 9 | 10.0 | (5.3, 18.1) | 92 | 11 | 12.0 | (6.7, 20.3) |
| | | 64 | 64 | 2 | 3.1 | (0.8, 11.7) | 15 | 0 | 0.0 | (0.2, 35.8) | 90 | 7 | 7.8 | (3.8, 15.4) | 92 | 5 | 5.4 | (2.3, 12.4) |
| | | 128 | 64 | 0 | 0.0 | (0.0, 11.2) | 15 | 0 | 0.0 | (0.2, 35.8) | 90 | 1 | 1.1 | (0.2, 7.5) | 92 | 0 | 0.0 | (0.0, 8.0) |
| | 1-month postdose 2 | 32 | 69 | 3 | 4.3 | (1.4, 12.6) | 21 | 20 | 95.2 | (72.9, 99.3) | 115 | 113 | 98.3 | (93.3, 99.6) | 115 | 105 | 91.3 | (84.6, 95.3) |
| | | 64 | 69 | 1 | 1.4 | (0.2, 9.6) | 21 | 18 | 85.7 | (63.9, 95.3) | 115 | 95 | 82.6 | (74.6, 88.5) | 115 | 83 | 72.2 | (63.3, 79.6) |
| | | 128 | 69 | 1 | 1.4 | (0.2, 9.6) | 21 | 11 | 52.4 | (31.8, 72.1) | 115 | 51 | 44.3 | (35.5, 53.5) | 115 | 49 | 42.6 | (33.9, 51.8) |
| | 1-month postdose 3 | 32 | 57 | 5 | 8.8 | (3.7, 19.4) | 19 | 18 | 94.7 | (70.6, 99.3) | 108 | 108 | 100.0 | (93.1, 100.0) | 99 | 98 | 99.0 | (93.2, 99.9) |
| | | 64 | 57 | 3 | 5.3 | (1.7, 15.1) | 19 | 18 | 94.7 | (70.6, 99.3) | 108 | 103 | 95.4 | (89.4, 98.1) | 99 | 90 | 90.9 | (83.4, 95.2) |
| | | 128 | 57 | 2 | 3.5 | (0.9, 13.0) | 19 | 13 | 68.4 | (45.2, 85.1) | 108 | 73 | 67.6 | (58.2, 75.7) | 99 | 67 | | (57.9, 76.1) |
| Subfamily A Strain 1 | Predose 1 | 16 | 81 | 10 | 12.3 | (6.8, 21.4) | 21 | 1 | 4.8 | (0.7, 27.1) | 122 | 11 | 9.0 | (5.1, 15.6) | 114 | 7 | 6.1 | (3.0, 12.3) |
| | | 32 | 81 | 6 | 7.4 | (3.4, 15.5) | 21 | 1 | 4.8 | (0.7, 27.1) | 122 | 7 | 5.7 | (2.8, 11.5) | 114 | 5 | 4.4 | (1.8, 10.1) |
| | | 64 | 81 | 4 | 4.9 | (1.9, 12.4) | 21 | 0 | 0.0 | (0.1, 28.2) | 122 | 3 | 2.5 | (0.8, 7.3) | 114 | 2 | 1.8 | (0.4, 6.7) |
| | | 128 | 81 | 1 | 1.2 | (0.2, 8.2) | 21 | 0 | 0.0 | (0.1, 28.2) | 122 | 1 | 0.8 | (0.1, 5.6) | 114 | 0 | 0.0 | (0.0, 6.6) |
| | 1-month postdose 2 | 16 | 83 | 6 | 7.2 | (3.3, 15.2) | 18 | 16 | 88.9 | (64.8, 97.2) | 118 | 105 | 89.0 | (81.9, 93.5) | 110 | 100 | 90.9 | (83.9, 95.0) |
| | | 32 | 83 | 3 | 3.6 | (1.2, 10.6) | 18 | 16 | 88.9 | (64.8, 97.2) | 118 | 101 | 85.6 | (78.0, 90.9) | 110 | 90 | 81.8 | (73.5, 88.0) |
| | | 64 | 83 | 1 | 1.2 | (0.2, 8.1) | 18 | 15 | 83.3 | (59.1, 94.5) | 118 | 70 | 59.3 | (50.2, 67.8) | 110 | 71 | 64.5 | (55.2, 72.9) |
| | | 128 | 83 | 0 | 0.0 | (0.0, 8.9) | 18 | 6 | 33.3 | (15.8, 57.1) | 118 | 33 | 28.0 | (20.6, 36.7) | 110 | 44 | 40.0 | (31.3, 49.4) |
| | 1-month postdose 3 | 16 | 76 | 9 | 11.8 | (6.3, 21.2) | 20 | 18 | 90.0 | (67.6, 97.5) | 114 | 110 | 96.5 | (91.0, 98.7) | 104 | 100 | 96.2 | (90.2, 98.5) |
| | | 32 | 76 | 6 | 7.9 | (3.6, 16.5) | 20 | 18 | 90.0 | (67.6, 97.5) | 114 | 108 | 94.7 | (88.8, 97.6) | 104 | 99 | 95.2 | (89.0, 98.0) |
| | | 64 | 76 | 3 | 3.9 | (1.3, 11.5) | 20 | 17 | 85.0 | (62.4, 95.1) | 114 | 102 | 89.5 | (82.4, 93.9) | 104 | 91 | 87.5 | (79.7, 92.6) |
| | | 128 | 76 | 1 | 1.3 | (0.2, 8.8) | 20 | 8 | 40.0 | (21.4, 62.0) | 114 | 78 | 68.4 | (59.3, 76.3) | 104 | 63 | 60.6 | (50.9, 69.5) |
| Subfamily A Strain 3 | Predose 1 | 16 | 80 | 8 | 10.0 | (5.1, 18.7) | 21 | 1 | 4.8 | (0.7, 27.1) | 119 | 9 | 7.6 | (4.0, 13.9) | 115 | 7 | 6.1 | (2.9, 12.2) |
| | | 32 | 80 | 6 | 7.5 | (3.4, 15.7) | 21 | 1 | 4.8 | (0.7, 27.1) | 119 | 6 | 5.0 | (2.3, 10.8) | 115 | 5 | 4.3 | (1.8, 10.0) |
| | | 64 | 80 | 2 | 2.5 | (0.6, 9.4) | 21 | 0 | 0.0 | (0.1, 28.2) | 119 | 1 | 0.8 | (0.1, 5.7) | 115 | 4 | 3.5 | (1.3, 8.9) |
| | | 128 | 80 | 1 | 1.3 | (0.2, 8.3) | 21 | 0 | 0.0 | (0.1, 28.2) | 119 | 0 | 0.0 | (0.0, 6.3) | 115 | 0 | 0.0 | (0.0, 6.5) |
| | 1-month postdose 2 | 16 | 81 | 10 | 12.3 | (6.8, 21.4) | 20 | 17 | 85.0 | (62.4, 95.1) | 117 | 111 | 94.9 | (89.1, 97.7) | 107 | 103 | 96.3 | (90.5, 98.6) |
| | | 32 | 81 | 9 | 11.1 | (5.9, 20.0) | 20 | 17 | 85.0 | (62.4, 95.1) | 117 | 106 | 90.6 | (83.8, 94.7) | 107 | 95 | 88.8 | (81.3, 93.5) |
| | | 64 | 81 | 8 | 9.9 | (5.0, 18.5) | 20 | 16 | 80.0 | (57.2, 92.3) | 117 | 94 | 80.3 | (72.1, 86.6) | 107 | 76 | 71.0 | (61.8, 78.8) |
| | | 128 | 81 | 2 | 2.5 | (0.6, 9.3) | 20 | 9 | 45.0 | (25.3, 66.4) | 117 | 46 | 39.3 | (30.9, 48.4) | 107 | 49 | 45.8 | (36.6, 55.3) |
| | 1-month postdose 3 | 16 | 78 | 9 | 11.5 | (6.1, 20.7) | 21 | 20 | 95.2 | (72.9, 99.3) | 114 | 111 | 97.4 | (92.2, 99.1) | 112 | 107 | 95.5 | (89.7, 98.1) |
| | | 32 | 78 | 7 | 9.0 | (4.3, 17.6) | 21 | 18 | 85.7 | (63.9, 95.3) | 114 | 107 | 93.9 | (87.7, 97.0) | 112 | 105 | 93.8 | (87.5, 97.0) |
| | | 64 | 78 | 3 | 3.8 | (1.2, 11.3) | 21 | 15 | 71.4 | (49.2, 86.6) | 114 | 104 | 91.2 | (84.5, 95.2) | 112 | 95 | 84.8 | (76.9, 90.4) |
| | | 128 | 78 | 2 | 2.6 | (0.6, 9.7) | 21 | 13 | 61.9 | (40.2, 79.7) | 114 | 85 | 74.6 | (65.8, 81.7) | 112 | 75 | 67.0 | (57.8, 75.0) |
| Subfamily B Strain 1 | Predose 1 | 16 | 84 | 3 | 3.6 | (1.2, 10.5) | 22 | 0 | 0.0 | (0.1, 27.3) | 124 | 2 | 1.6 | (0.4, 6.2) | 118 | 3 | 2.5 | (0.8, 7.6) |

TABLE 5-continued

Subjects Achieving Defined SBA Titer Levels in Stage 1 - mITT Population (Study 6108A1-2001-WW/B1971005)

| Strain | Sampling Time Point | SBA Titer | Control | | | | 60 µg | | | | 120 µg | | | | 200 µg | | | |
|---|---|---|---|---|---|---|---|---|---|---|---|---|---|---|---|---|---|---|
| | | | $N^a$ | $n^b$ | % | (95% $CI^c$) | $N^a$ | $n^b$ | % | (95% $CI^c$) | $N^a$ | $n^b$ | % | (95% $CI^c$) | $N^a$ | $n^b$ | % | (95% $CI^c$) |
| | | 32 | 84 | 1 | 1.2 | (0.2, 8.0) | 22 | 0 | 0.0 | (0.1, 27.3) | 124 | 1 | 0.8 | (0.1, 5.5) | 118 | 2 | 1.7 | (0.4, 6.5) |
| | | 64 | 84 | 0 | 0.0 | (0.0, 8.8) | 22 | 0 | 0.0 | (0.1, 27.3) | 124 | 1 | 0.8 | (0.1, 5.5) | 118 | 0 | 0.0 | (0.0, 6.4) |
| | | 128 | 84 | 0 | 0.0 | (0.0, 8.8) | 22 | 0 | 0.0 | (0.1, 27.3) | 124 | 1 | 0.8 | (0.1, 5.5) | 118 | 0 | 0.0 | (0.0, 6.4) |
| | 1-month postdose 2 | 16 | 84 | 1 | 1.2 | (0.2, 8.0) | 21 | 16 | 76.2 | (54.0, 89.7) | 122 | 84 | 68.9 | (60.1, 76.4) | 114 | 75 | 65.8 | (56.6, 73.9) |
| | | 32 | 84 | 0 | 0.0 | (0.0, 8.8) | 21 | 12 | 57.1 | (36.0, 76.0) | 122 | 56 | 45.9 | (37.3, 54.8) | 114 | 55 | 48.2 | (39.2, 57.4) |
| | | 64 | 84 | 0 | 0.0 | (0.0, 8.8) | 21 | 9 | 42.9 | (24.0, 64.0) | 122 | 31 | 25.4 | (18.5, 33.9) | 114 | 25 | 21.9 | (15.3, 30.4) |
| | | 128 | 84 | 0 | 0.0 | (0.0, 8.8) | 21 | 3 | 14.3 | (4.7, 36.1) | 122 | 9 | 7.4 | (3.9, 13.6) | 114 | 10 | 8.8 | (4.8, 15.5) |
| | 1-month postdose 3 | 16 | 79 | 3 | 3.8 | (1.2, 11.1) | 21 | 18 | 85.7 | (63.9, 95.3) | 113 | 102 | 90.3 | (83.3, 94.5) | 105 | 90 | 85.7 | (77.6, 91.2) |
| | | 32 | 79 | 1 | 1.3 | (0.2, 8.4) | 21 | 17 | 81.0 | (58.8, 92.7) | 113 | 89 | 78.8 | (70.3, 85.3) | 105 | 83 | 79.0 | (70.2, 85.8) |
| | | 64 | 79 | 0 | 0.0 | (0.0, 9.3) | 21 | 12 | 57.1 | (36.0, 76.0) | 113 | 59 | 52.2 | (43.0, 61.2) | 105 | 63 | 60.0 | (50.4, 68.9) |
| | | 128 | 79 | 0 | 0.0 | (0.0, 9.3) | 21 | 9 | 42.9 | (24.0, 64.0) | 113 | 22 | 19.5 | (13.2, 27.8) | 105 | 20 | 19.0 | (12.6, 27.7) |
| Subfamily B Strain 2 | Predose 1 | 16 | 83 | 2 | 2.4 | (0.6, 9.1) | 22 | 0 | 0.0 | (0.1, 27.3) | 118 | 3 | 2.5 | (0.8, 7.6) | 117 | 3 | 2.6 | (0.8, 7.6) |
| | | 32 | 83 | 2 | 2.4 | (0.6, 9.1) | 22 | 0 | 0.0 | (0.1, 27.3) | 118 | 3 | 2.5 | (0.8, 7.6) | 117 | 3 | 2.6 | (0.8, 7.6) |
| | | 64 | 83 | 1 | 1.2 | (0.2, 8.1) | 22 | 0 | 0.0 | (0.1, 27.3) | 118 | 0 | 0.0 | (0.0, 6.4) | 117 | 1 | 0.9 | (0.1, 5.8) |
| | | 128 | 83 | 0 | 0.0 | (0.0, 8.9) | 22 | 0 | 0.0 | (0.1, 27.3) | 118 | 0 | 0.0 | (0.0, 6.4) | 117 | 0 | 0.0 | (0.0, 6.4) |
| | 1-month postdose 2 | 16 | 84 | 2 | 2.4 | (0.6, 9.0) | 19 | 4 | 21.1 | (8.1, 44.6) | 102 | 33 | 32.4 | (24.0, 42.0) | 96 | 29 | 30.2 | (21.9, 40.1) |
| | | 32 | 84 | 2 | 2.4 | (0.6, 9.0) | 19 | 4 | 21.1 | (8.1, 44.6) | 102 | 31 | 30.4 | (22.3, 40.0) | 96 | 27 | 28.1 | (20.0, 37.9) |
| | | 64 | 84 | 1 | 1.2 | (0.2, 8.0) | 19 | 1 | 5.3 | (0.7, 29.4) | 102 | 23 | 22.5 | (15.5, 31.7) | 96 | 19 | 19.8 | (13.0, 29.0) |
| | | 128 | 84 | 0 | 0.0 | (0.0, 8.8) | 19 | 0 | 0.0 | (0.2, 30.4) | 102 | 11 | 10.8 | (6.1, 18.4) | 96 | 8 | 8.3 | (4.2, 15.8) |
| | 1-month postdose 3 | 16 | 68 | 4 | 5.9 | (2.2, 14.6) | 15 | 8 | 53.3 | (29.3, 75.9) | 86 | 65 | 75.6 | (65.4, 83.5) | 81 | 55 | 67.9 | (57.0, 77.1) |
| | | 32 | 68 | 3 | 4.4 | (1.4, 12.8) | 15 | 8 | 53.3 | (29.3, 75.9) | 86 | 65 | 75.6 | (65.4, 83.5) | 81 | 54 | 66.7 | (55.8, 76.0) |
| | | 64 | 68 | 1 | 1.5 | (0.2, 9.7) | 15 | 7 | 46.7 | (24.1, 70.7) | 86 | 52 | 60.5 | (49.8, 70.2) | 81 | 47 | 58.0 | (47.1, 68.2) |
| | | 128 | 68 | 0 | 0.0 | (0.0, 10.6) | 15 | 4 | 26.7 | (10.4, 53.3) | 86 | 24 | 27.9 | (19.5, 38.3) | 81 | 20 | 24.7 | (16.5, 35.2) |
| Subfamily B Strain 3 | Predose 1 | 8 | 81 | 2 | 2.5 | (0.6, 9.3) | 22 | 0 | 0.0 | (0.1, 27.3) | 120 | 4 | 3.3 | (1.3, 8.5) | 116 | 3 | 2.6 | (0.8, 7.7) |
| | | 16 | 81 | 1 | 1.2 | (0.2, 8.2) | 22 | 0 | 0.0 | (0.1, 27.3) | 120 | 2 | 1.7 | (0.4, 6.4) | 116 | 3 | 2.6 | (0.8, 7.7) |
| | | 32 | 81 | 0 | 0.0 | (0.0, 9.1) | 22 | 0 | 0.0 | (0.1, 27.3) | 120 | 0 | 0.0 | (0.0, 6.3) | 116 | 2 | 1.7 | (0.4, 6.6) |
| | | 64 | 81 | 0 | 0.0 | (0.0, 9.1) | 22 | 0 | 0.0 | (0.1, 27.3) | 120 | 0 | 0.0 | (0.0, 6.3) | 116 | 1 | 0.9 | (0.1, 5.9) |
| | | 128 | 81 | 0 | 0.0 | (0.0, 9.1) | 22 | 0 | 0.0 | (0.1, 27.3) | 120 | 0 | 0.0 | (0.0, 6.3) | 116 | 1 | 0.9 | (0.1, 5.9) |
| | 1-month postdose 2 | 8 | 81 | 1 | 1.2 | (0.2, 8.2) | 21 | 13 | 61.9 | (40.2, 79.7) | 115 | 79 | 68.7 | (59.7, 76.5) | 106 | 75 | 70.8 | (61.4, 78.6) |
| | | 16 | 81 | 0 | 0.0 | (0.0, 9.1) | 21 | 13 | 61.9 | (40.2, 79.7) | 115 | 70 | 60.9 | (51.7, 69.3) | 106 | 68 | 64.2 | (54.6, 72.7) |
| | | 32 | 81 | 0 | 0.0 | (0.0, 9.1) | 21 | 10 | 47.6 | (27.9, 68.2) | 115 | 50 | 43.5 | (34.7, 52.7) | 106 | 45 | 42.5 | (33.4, 52.0) |
| | | 64 | 81 | 0 | 0.0 | (0.0, 9.1) | 21 | 5 | 23.8 | (10.3, 46.0) | 115 | 26 | 22.6 | (15.9, 31.1) | 106 | 27 | 25.5 | (18.1, 34.6) |
| | | 128 | 81 | 0 | 0.0 | (0.0, 9.1) | 21 | 0 | 0.0 | (0.1, 28.2) | 115 | 7 | 6.1 | (2.9, 12.2) | 106 | 12 | 11.3 | (6.5, 18.9) |
| | 1-month postdose 3 | 8 | 83 | 4 | 4.8 | (1.8, 12.1) | 21 | 16 | 76.2 | (54.0, 89.7) | 115 | 102 | 88.7 | (81.5, 93.3) | 111 | 96 | 86.5 | (78.8, 91.7) |

TABLE 5-continued

Subjects Achieving Defined SBA Titer Levels in Stage 1 - mITT Population (Study 6108A1-2001-WW/B1971005)

| | | | Vaccine Group (as Randomized) | | | | | | | | | | | | | | |
|---|---|---|---|---|---|---|---|---|---|---|---|---|---|---|---|---|---|
| | | | Control | | | | 60 µg | | | | rLP2086 Vaccine 120 µg | | | | 200 µg | | | |
| Strain | Sampling Time Point | SBA Titer | $N^a$ | $n^b$ | % | (95% $CI^c$) | $N^a$ | $n^b$ | % | (95% $CI^c$) | $N^a$ | $n^b$ | % | (95% $CI^c$) | $N^a$ | $n^b$ | % | (95% $CI^c$) |
| | | 16 | 83 | 1 | 1.2 | (0.2, 8.1) | 21 | 16 | 76.2 | (54.0, 89.7) | 115 | 99 | 86.1 | (78.5, 91.3) | 111 | 95 | 85.6 | (77.8, 91.0) |
| | | 32 | 83 | 0 | 0.0 | (0.0, 8.9) | 21 | 16 | 76.2 | (54.0, 89.7) | 115 | 93 | 80.9 | (72.6, 87.1) | 111 | 89 | 80.2 | (71.7, 86.6) |
| | | 64 | 83 | 0 | 0.0 | (0.0, 8.9) | 21 | 10 | 47.6 | (27.9, 68.2) | 115 | 62 | 53.9 | (44.8, 62.8) | 111 | 68 | 61.3 | (51.9, 69.9) |
| | | 128 | 83 | 0 | 0.0 | (0.0, 8.9) | 21 | 2 | 9.5 | (2.4, 31.1) | 115 | 26 | 22.6 | (15.9, 31.1) | 111 | 22 | 19.8 | (13.4, 28.3) |

Abbreviations: CI = confidence interval;
SBA = serum bactericidal assay;
LLOQ = lower limit of quantitation.
Note:
LLOQ for A/1 = 9, A/2 = 18, A/3 = 12, B/1 = 10, B/2 = 9, B/3 = 7.

The immunogenicity data show that the vaccine can generate antibodies with significant SBA activity against subfamily A and subfamily B strains of MnB. For Subfamily A Strain 2. after dose 2, SBA response rates ranged from 88.9% to 90.9% and after dose 3 the SBA response rates ranged from 90.0% to 97.4%. For Subfamily A Strain 1 variant, after both dose 2 and dose 3, 100.0% of the subjects had SBA responses to this variant at both the 60-m and 120-m dose levels. At the 200-m dose level, 96.5% and 99.0% of the subjects had SBA responses after dose 2 and dose 3, respectively. For Subfamily A Strain 1 variant, the SBA response rates ranged from 85.0% to 96.3% after dose 2 and from 95.2% to 97.4% after dose 3.

For Subfamily B Strain 1 variant, after dose 2 the SBA response rates ranged from 76.2% to 81.0%, and after dose 3 the SBA response rates ranged from 89.5% to 92.0%. For Subfamily B Strain 2 variant after dose 2, the percentage of subjects with SBA response rates ranged from 21.1% to 33.3%. However, after the third dose, 53.3%, 75.6%, and 67.9% of the subjects had SBA responses at the 60-m, 120-m, and 200-m dose levels, respectively. For Subfamily B Strain 3 variant, the SBA response rates ranged from 61.9% to 70.8% after dose 2 and from 76.2% to 88.7% after dose 3.

Overall, a high proportion of subjects responded with an SBA titer ≥LLOQ irrespective of the subfamily A or subfamily B strain tested. The hSBA data showed robust immune responses at doses of 60 µg to 200 µg without a clear dose-response relationship. The frequency of response, irrespective of the analysis examined, was highest numerically in the 120-µg group. The 200-µg group did not have improved immune responses over the 120-µg dose level.

What is claimed is:

1. An immunogenic composition consisting essentially of 120 µg/mL of a purified lipidated *Neisseria meningitidis* serogroup B LP2086 (fHBP) Subfamily B polypeptide; Polysorbate 80, wherein the molar ratio of the Polysorbate 80 to the polypeptide is 2.8:1; 0.5 mg/mL aluminum as aluminum phosphate; 10 mM histidine at a pH of 6.0; and 150 mM sodium chloride.

2. An immunogenic composition consisting essentially of 120 µg/mL of a purified lipidated *Neisseria meningitidis* serogroup B LP2086 (fHBP) Subfamily B polypeptide; 120 µg/mL of a purified lipidated *Neisseria meningitidis* serogroup B LP2086 (fHBP) Subfamily A polypeptide; Polysorbate 80, wherein the molar ratio of the Polysorbate 80 to the polypeptide is 2.8:1; 0.5 mg/mL aluminum as aluminum phosphate; 10 mM histidine at a pH of 6.0; and 150 mM sodium chloride.

3. An immunogenic composition consisting essentially of 120 µg/mL of a purified lipidated *Neisseria meningitidis* serogroup B LP2086 (fHBP) Subfamily B polypeptide; Polysorbate 80, wherein the molar ratio of the Polysorbate 80 to the polypeptide is 2.8:1; 0.5 mg/mL aluminum as aluminum phosphate; 5 mM succinate at a pH 6.0; and 150 mM sodium chloride.

4. An immunogenic composition consisting essentially of 120 µg/mL of a purified lipidated *Neisseria meningitidis* serogroup B LP2086 (fHBP) subfamily B polypeptide; 120 µg/mL of a purified lipidated *Neisseria meningitidis* serogroup B LP2086 (fHBP) Subfamily A polypeptide; Polysorbate 80, wherein the molar ratio of the Polysorbate 80 to the polypeptide is 2.8:1; 0.5 mg/mL aluminum as aluminum phosphate; 5 mM succinate at a pH of 6.0; and 150 mM sodium chloride.

* * * * *